US007253274B2

(12) United States Patent
Dean et al.

(10) Patent No.: US 7,253,274 B2
(45) Date of Patent: Aug. 7, 2007

(54) METHODS AND MEANS FOR MODIFICATION OF PLANT CHARACTERISTICS USING THE VERNALIZATION GENE VRN2

(75) Inventors: Caroline Dean, Norwich (GB); Anthony Gendall, Norwich (GB)

(73) Assignee: Pioneer Hi-Bred International, Johnston, IA (US)

( * ) Notice: Subject to any disclaimer, the term of this patent is extended or adjusted under 35 U.S.C. 154(b) by 178 days.

(21) Appl. No.: 10/942,711

(22) Filed: Sep. 16, 2004

(65) Prior Publication Data

US 2005/0132446 A1 Jun. 16, 2005

Related U.S. Application Data

(63) Continuation of application No. 09/890,220, filed as application No. PCT/GB00/00248 on Jan. 28, 2000, now abandoned.

(30) Foreign Application Priority Data

Jan. 28, 1999 (GB) ................................ 9901927.5

(51) Int. Cl.
*C12N 15/29* (2006.01)
(52) U.S. Cl. ..................................... 536/23.6; 536/23.1
(58) Field of Classification Search ............... 536/23.1, 536/23.6
See application file for complete search history.

(56) References Cited

U.S. PATENT DOCUMENTS 5,688,768 A 11/1997 Coughlin et al.
2004/0205848 A1* 10/2004 Dubcovsky et al. ........ 800/295

FOREIGN PATENT DOCUMENTS

EP 0967278 A 12/1999
WO WO 96/38560 A 12/1996

OTHER PUBLICATIONS

Zhang et al (2002, The Plant Journal 31(5):663-673).*
Bowie et al, Science 247:1306-1310, 1990.*
McConnell et al, Nature 411 (6838):709-713, 2001.*
Fourgoux-Nicol et al (1999, Plant Molecular Biology 40:857-872).*
Bowie, J.U., et al., "Deciphering the Message in Protein Sequences: Tolerance to Amino Acid Substitutions", Science, vol. 247: p. 1306-1310 (1990).
McConnell, J.R., et al., "Role of Phabulosa and Phavoluta in determining radial patterning in shoots", Nature, vol. 411: p. 709-713, (2001).
Fourgoux-Nicol, A., et al., "Isolation of rapeseed genes expressed early and specifically during development of the male gametophyte", Plant Molecular Biology, vol. 40:857-872, (1999).

Bowman, J.L., et al., "Crabs Claw, a gene that regulates carpel and nectary development in Arabidopsis, encodes a novel protein with zinc finger and helix-loop-helix domains", Development, vol. 126: 2387-2396, (1999).
Siegfried, K.R., et al., "Members of the YABBY gene family specifiy abaxial cell fate in Arabidopsis", Development, vol. 126: p. 4117-4128, (1999).
Schmidt, R., et al., "Physical Map and Organization of *Arabidopsis thaliana* Chromosome 4", Science vol. 270: p. 480-483, (1995).
Kano-Murakami, Y., et al., "A rice homeotic gene, OSH1, causes unusual phenotypes in transgenic tobacco", FEBS vol. 334: p. 365-368, (1993).
Chandler, J., et al., "Arabidopsis mutants showing an altered response to vernalization", The Plant Journal, vol. 10: p. 637-644, (1996).
Wilson, A., et al., "Analysis of the molecular basis of vernalization in *Arabidopsis thaliana*", Seminars in Cell and Developmental Biology, vol. 7: p. 439-440, (1996).
Levy, Y., et al., "The transition of flowering", Plant Cell, US American Society of Plant Physiologists, vol. 10: p. 1973-1989, (1998).
Bevan, M., et al., "EU Arabidopsis sequencing project—unpublished", EMBL Sequence Data Library, accession No. Z97342, (1997).
Bancroft, I., et al., "The development of systems for the isolation of genes from *Arabidopsis thaliana* by chromosome walking in YAK libraries: Towards the isolation of the floral induction gene GCA. UP8.62", J. of Experimental Botany, vol. 42 (suppl.): p. 48 (1991).
Robson, P.R.H., et al., "Genetic engineering of harvest index in tobacco through overexpression of a phytochrome gene", Nature Biotechnology, vol. 14: p. 995-998, (1996).
Parker, J.E., et al., "The Arabidopsis downy mildew resistance gene RPP5 shares similarity to the toll and interleukin-1 receptors with N and L6", EMBL Sequence Data Library, accession No. AF180942, (1999).
Sheldon, C., et al., "The FLF MADS box gene: a repressor of flowering in Arabidopsis regulated by vernalization and methylation", Plant Cell, US American Society of Plant Physiologists, vol. 11: p. 445-458 (1999).
Bevan, et al., "Analysis of 1.9 Mb of contiguous sequence from chromosome 4 of *Arabidopsis thaliana*", Nature, vol. 391: p. 485-488, (1998).
Parker, et al., "The Arabidopsis Downy Mildew Resistance Gene RPP5 Shares Similarity to the Toll and Interleukin-1 Receptors with N and L6", Plant Cell, vol. 9: p. 1-17, (1998).

(Continued)

*Primary Examiner*—Stuart F. Baum
(74) *Attorney, Agent, or Firm*—Dann, Dorfman, Herrell & Skillman; Kathleen D. Rigaut

(57) ABSTRACT

An isolated nucleic acid obtainable from the VRN2 locus of a plant, which nucleic acid encodes a polypeptide which is capable of affecting one or more physical characteristics of a plant into which the nucleic acid is introduced, the physical characteristics being selected from vernalization response, flowering time, leaf size, and/or shape or shade avoidance response; alleles, fragment and derivatives thereof; polypeptides encoded by such nucleic acids; antibodies to such peptides.

4 Claims, 12 Drawing Sheets

OTHER PUBLICATIONS

Schmidt, et al., "Detailed description of 4 YAC contigs representing 17 Mb of chromosome 4 of *Arabidopsis thaliana* ecotype Columbia", Plant J., vol. 9: 755-765, (1996).

Ecker, J.R., et al., "Genes blossom from a weed", Nature, vol. 391: p. 438-9, (1998).

Wu, S.C., Expressed sequence tags of the rice blast fungus grown on rice cell walls; EMBL Accession No. AA415086; Oct. 27, 1997.

EMBL-EBI Allignment Display SA265716_0001.DNA; Seq. ID Nos. 1,4,7; (19 pages).

* cited by examiner

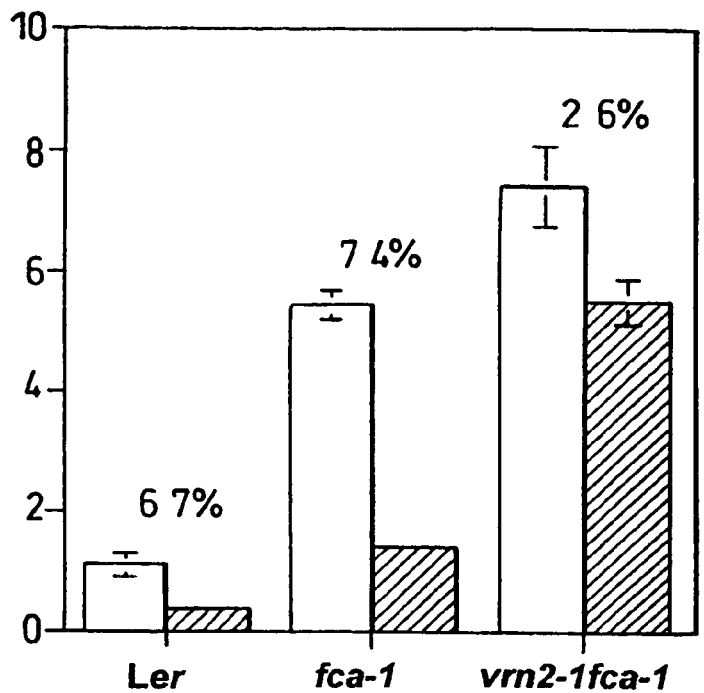
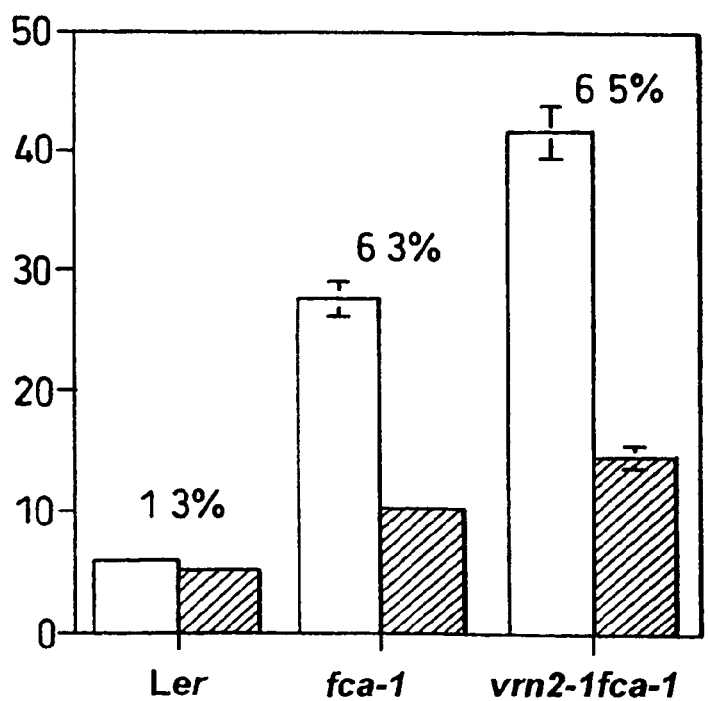
*Fig. 2*

```
                                                    ▼      CAAGC          5
TTCTTCAATTTTGCTTGCTCTCTCTTACACAGCCAATCGGTGTTTTCGCAGCTTTCAGGCCTCAATCCAAGACAT    80
TCTATATAAGCATATTGCAGAAGAGGCGGTTCTAATTGTTGCATTGAGTTTATCGCTATGACGTAGGGAAATTCT   155
AATTTAGGGGAGGCCTCAGAGTTTGCACTAACTTCATAATCGGCTCTTGACGTTGTTGAGTGTAATTGAACAAGA   230

ATGTGTAGGCAGAATTGTCGCGCGAAATCCTCACCGGAGGAAGTGATTTCAACTGATGAGAATCTCTTGATATAT   305
 M  C  R  Q  N  C  R  A  K  S  S  P  E  E  V  I  S  T  D  E  N  L  L  I  Y     25
                                ▼
TGTAAACCTGTTCGACTATATAACATCTTTCACCTTCGCTCTCTAGGCAACCCATCGTTTCTTCCAAGATGCTTG   380
 C  K  P  V  R  L  Y  N  I  F  H  L  R  S  L  G  N  P  S  F  L  P  R  C  L     50

AACTACAAAATTGGAGCAAAGCGCAAAAGAAAGTCAAGATCTACTGGGATGGTAGTTTTCAACTATAAGGATTGT   455
 N  Y  K  I  G  A |K  R  K  R  K| S  R  S  T  G  M  V  V  F  N  Y  K  D  C     75
                            ▼
AATAACACATTACAGAAAACTGAAGTTAGGGAGGATTGTTCTTGTCCATTTTGCTCTATGCTATGTGGTAGCTTC   530
 N  N  T  L  Q  K  T  E  V  R  E  D  C  S  C  P  F  C  S  M  L  C  G  S  F    100
                                            =  =  =  =  =  =  =  =  =  =  =
 ▼
AAGGGGCTGCAATTTCATTTGAATTCATCTCATGATTTATTTGAATTTGAGTTCAAGCTTTTCGAAGAATACCAG   605
 K  G  L  Q  F  H  L  N  S  S  H  D  L  F  E  F  K  L  F  E  E  Y  Q           125
 =  =  =  =  =  =  =  =  =  =

ACAGTTAATGTTTCTGTAAAACTTAATTCCTTCATATTTGAGGAAGAAGGAAGTGATGACGATAAATTTGAGCCC   680
 T  V  N  V  S  V  K  L  N  S  F  I  F  E  E  E  G  S  D  D  D  K  F  E  P    150

▼
TTCTCTCTCTGCTCGAAACCTCGTAAGCGGAGACAAAGAGGTGGCAGAAATAACACCAGGAGACTTAAAGTATGC   755
 F  S  L  C  S  K  P |R  K| R  R  Q  R  G  G  R  N  N  T |R  R  L  K  V| C    175

▼
TTTTTACCGTTGGATTCACCCAGTTTAACTAATGGCACAGAAAATGGAATCACCCTACTTAATGATGGAAACCGT   830
 F  L  P  L  D  S  P  S  L  T  N  G  T  E  N  G  I  T  L  L  N  D  G  N  R    200

GGTTTAGGATATCCCGAGGCAACAGAGCTTGCTGGACAATTTGAGATGACCAGCAACATTCCACCAGCCATAGCC   905
 G  L  G  Y  P  E  A  T  E  L  A  G  Q  F  E  M  T  S  N  I  P  P  A  I  A    225

CACTCTTCTCTGGACGCTGGTGCTAAAGTTATATTGACAAGCGAAGCTGTGGTCCCTGCTACTAAGACAAGAAAG   980
 H  S  S  L  D  A  G  A  K  V  I  L  T  S  E  A  V  V  P  A  T  K  T  R  K    250
                    ▼
TTATCTGCTGAGCGATCAGAGGCTAGAAGCCACCTACTTCTTCAGAAACGCCAATTCTATCATTCTCACAGAGTC  1055
 L  S  A  E  R  S  E  A  R  S  H  L  L  L  Q  K  R  Q  F  Y  H  S  H  R  V    275
             ▼
CAGCCAATGGCGCTTGAGCAAGTAATGTCTGACCGGGATAGCGAGGATGAAGTCGATGACGATGTTGCAGATTTT  1130
 Q  P  M  A  L  E  Q  V  M  S  D  R  D  S  E  D  E  V  D  D  D  V  A  D  F    300
           ▼                                                    ↓ vm2-1
GAAGATCGCCAGATGCTTGATGACTTTGTGGATGTGAATAAAGATGAAAAGCAATTCATGCATCTTTGGAACTCG  1205
 E  D  R  Q  M  L  D  D  F  V  D  V  N  K  D  E  K  Q  F  M  H  L (W) N  S    325
              ▼
TTTGTAAGAAAACAAAGGGTTATAGCAGATGGTCATATCTCTTGGGCATGTGAAGCATTTTCAAGATTTTACGAG  1280
 F  V  R  K  Q  R  V  I  A  D  G  H  I  S  W  A  C  E  A  F  S  R  F  Y  E    350
                                ▼
AAAGAGTTGCACCGTTACTCATCACTCTTCTGGTGTTGGAGATTGTTTTTGATTAAACTATGGAACCATGGACTT  1355
 K  E  L  H  R  Y  S  S  L  F  W  C  R  L  F  L  I  K  L  W  N  H  G  L       375

GTCGACTCAGCCACCATCAACAACTGCAATACCATCCTCGAGAATTGCCGTAATAGCTCAGACACCACCACCACC  1430
 V  D  S  A  T  I  N  N  C  N  T  I  L  E  N  C  R  N  S  S  D  T  T  T  T    400

AACAACAACAACAGTGTGGATCGTCCCAGTGACTCAAACACCAACAACAATAACATTGTGGATCATCCCAATGAC  1505
 N  N  N  N  S  V  D  R  P  S  D  S  N  T  N  N  N  I  V  D  H  P  N  D       425

ATAAACAACAAGAACAATGTTGACAACAAGGACAATAACAGCAGAGACAAAGTAATTAAATAGGAAAATCTCCGG  1580
  I  N  N  K  N  N  V  D  N  K  D  N  N  S  R  D  K  V  I  K                  445

CTTTTATGATACCGATTTATCGGATTGTAACTTATTCTTCTTTCTTAAAAAATTGTTTAGGAGCAAACAAATTTT  1655
TTATATGTTAGTGTATTCAACTGATTACATTTTTAGTTAAAAAAAAAAATGGATTCTGCTTATAACT          1722
```

```
                              W323
fca-1    GAAAAGCAATTCATGCATCTT TGG AACTCGTTTGTAAGAA
vrn2-1                        TGA
                              STOP GAAAAGCAATTCATGCATCTTTGAAACTCGTTTGTAAGAA
                              CTTNNNNAAG
                              XmnI site
```

Diagnostic Primer: VRN2-AZ Antisense   3' TGAGAAGACATTCTTTTGTTTCCATTGATGAAGAG 5'
(contains a A and G mismatches at positions 5,7)          (CTT)NNNNAAG
                                                          XmnI half-site

Upstream Primer: VRN2-AY   5' TGCGTTCATTAAGTAGGCAACAGAAAATGG 3'

Product:    170 bp PCR product for both *fca-1* and *vrn2-1*

PCR Products:

```
fca-1    GAAAAGCAATTCATGCATCTTTGGAACTCTTCTGTAAGAA
vrn2-1   GAAAAGCAATTCATGCATCTTTGGATCTTTGAAACTCTCTGTAAGAA
```

XmnI digest =>   *fca-1*    no XmnI site          170 bp
                 *vrn2-1*   single XmnI site      137 bp, 33 bp fragments

[Figure: Multiple sequence alignment continuation showing protein sequences for VRN2 Ler, AI163743 Prot, Rice C72616, At Hyp 2245035, and KIA00160 with position numbers ranging from 140 to 600.]

Figure 8a continued

```
VRN2 Ler        A V P A T K T R K L S A E R S E A R S    260
AI163743 Prot   A M L Q F A K T R K L S D D M R N        40
Rice C72616     - V L Q F G K T R K L S - V E R A D P    93
At Hyp 2245035  A K V P A - - - - - - - - K R S A I S    21
KIA00160        K A S M S E F L E S E D G E V E Q R T    620

VRN2 Ler        H L - - L L Q K R Q F Y H S H R Q P M A  279
AI163743 Prot   R T - - L L H K R Q F F H S H R R P M A  59
Rice C72616     R Q - - L L Q H R Q F Y H S H R A Q P M A 112
At Hyp 2245035  H Y L - P L H K R Q F Y H S D T C L P S  41
KIA00160        S G H N R L Y - - - - - - - - - P L R    639

VRN2 Ler        L E Q V M S D R D S E D E V D - - - D V  297
AI163743 Prot   A E Q V M S D R D S E E D D D D D V      77
Rice C72616     L G A V F D D R D S D D V D D - - D A    130
At Hyp 2245035  L E Q V M D R D S E N D - - - K - - - L  61
KIA00160        P Q E M - - E V D S E D E K D - - P E W  655

VRN2 Ler        A D F E D R Q M L D D F V D V N K D - - E 316
AI163743 Prot   A D F E D R R M L D D F V D V K D - - E   96
Rice C72616     A D F E P R Q M L D D F V D N E T - - E   149
At Hyp 2245035  A H L E E S Q M L - Q E F S D V N E G - E 81
KIA00160        L R E K T - Q L N G S M D E N E G - - -   674

VRN2 Ler        K Q F M H L W N S F V R K Q R V I A D G  336
AI163743 Prot   K L M M H L W N S F V R                   108
Rice C72616     - - L M H M - - - - - - - - - - -        154
At Hyp 2245035  E R F L K L W N S F V K Q Q R I V A D A  101
KIA00160        K E V M K L H V M K H G F I A D N        694

VRN2 Ler        H I S W A C E A F S R F Y E K E L H R Y  356
AI163743 Prot                                             108
Rice C72616                                               154
At Hyp 2245035  H I P W A C E A F S R L H L Q E L R S N  121
KIA00160        Q M N H A C M L F V E N Y G Q K I K K    714
```

VRN2 Ler
AI163743 Prot
Rice C72616
At Hyp 2245035
KIA00160

Figure 8a continued

| | | | | | | | | | | | | | |
|---|---|---|---|---|---|---|---|---|---|---|---|---|---|
VRN2 Ler | S | S | L | F | W | C | W | R | L | F | I | K | L | W | N | H | G | L | V | 376
AI163743 Prot | | | | | | | | | | | | | | | | | | | | 108
Rice C72616 | | | | | | | | | | | | | | | | | | | | 154
At Hyp 2245035 | L | S | L | D | L | C | W | R | Q | F | M | L | K | Q | W | D | D | Y | G | L | 141
KIA00160 | N | L | C | R | N | F | M | L | H | L | V | S | M | H | D | D | F | L | I | 733

VRN2 Ler | D | S | A | T | I | N | C | N | T | I | L | E | N | C | R | N | S | S | D | 396
AI163743 Prot | | | | | | | | | | | | | | | | | | | 108
Rice C72616 | | | | | | | | | | | | | | | | | | | 154
At Hyp 2245035 | D | R | V | T | M | N | K | C | N | T | L | Y | H | N | L | S | T | T | N | 161
KIA00160 | S | I | M | S | I | D | K | A | V | T | K | L | R | E | M | Q | Q | K | L | E | 753

VRN2 Ler | T | T | T | N | N | S | V | D | R | P | S | D | S | N | T | N | 416
AI163743 Prot | | | | | | | | | | | | | | | | 108
Rice C72616 | | | | | | | | | | | | | | | | 154
At Hyp 2245035 | D | D | I | N | N | T | R | T | T | D | N | M | E | Q | T | D | D | A | 181
KIA00160 | K | G | E | S | A | S | P | A | N | E | E | I | T | E | Q | N | G | T | A | 773

VRN2 Ler | N | N | I | V | D | H | P | N | D | I | N | N | K | N | N | V | D | N | K | D | 436
AI163743 Prot | | | | | | | | | | | | | | | | | | | | 108
Rice C72616 | | | | | | | | | | | | | | | | | | | | 154
At Hyp 2245035 | I | N | R | D | K | S | E | I | N | S | K | E | K | A | L | E | T | D | S | V | S | G | 186
KIA00160 | N | G | F | | | | | | | | | | | | | | | | | 793

VRN2 Ler | N | N | S | R | D | K | V | I | K | 445
AI163743 Prot | | | | | | | | | | 108
Rice C72616 | | | | | | | | | | 154
At Hyp 2245035 | | | | | | | | | | 186
KIA00160 | V | S | K | Q | S | K | K | Q | K | L | 803

Figure 8b

METHODS AND MEANS FOR MODIFICATION OF PLANT CHARACTERISTICS USING THE VERNALIZATION GENE VRN2

This application is a continuation application of U.S. patent application Ser. No. 09/890,220 (now abandoned), filed Dec. 18, 2001 which is a §371 Application of PCT/GB00/00248 filed Jan. 28, 2000. The foregoing application is incorporated by reference herein.

In different embodiments, the present invention provides for manipulation of flowering time and/or other characteristics of plants, e.g. by up or down regulating VRN2 gene expression. The present invention also provides for modification of the extent of alteration of a relevant plant characteristic through the use of gene alleles, mutants and variants.

Plants must integrate a wide variety of environmental signals in order to maximize their reproductive success. Part of this integration must involve perception of the seasons, both to ensure the plant flowers during the correct season (for which it is adapted) and to synchronise its flowering with other members of its own species, to increase the chances of cross-fertilization. *Arabidopsis thaliana* serves as a model plant, for it exhibits responses to a wide variety of environmental stimuli that are observed in many species. Flowering in naturally occurring strains (ecotypes) of *Arabidopsis* can be promoted either by long days (increased photoperiod) or by vernalization, a long cold treatment that mimics the cold of winter. While many aspects of the photoperiodic response are now understood, the vernalization pathway has received relatively less attention. The inventors have used a late flowering, vernalization responsive mutant of *Arabidopsis*, the fca mutant, as a background in which to isolate mutants that exhibit a reduced vernalization response, the VRN mutants.

Vernalization is the low temperature promotion of flowering. It can also be thought of as the cold aspect of the winter season, which also includes reduced daylight hours. Many species of plants that grow in temperate or cooler climes have an obligate requirement for vernalization in order to flower. Such plants typically germinate in autumn, and over-winter as vegetative plants, and flower in milder conditions of spring. Vernalization thus acts as a cue, to allow plants to sense the seasons, and to time their flowering to maximise their chance of reproductive success.

Species for which flowering is important to crop production are numerous, essentially all crops which are grown from seed, with important examples being the cereals, rice and maize, probably the most agronomically important in warmer climatic zones, and wheat, barley, oats and rye in more temperate climates. Important seed products are oil seed rape, sugar beet, maize, sunflower, soybean and sorghum. Many crops which are harvested for their roots are, of course, grown annually from seed and the production of seed of any kind is very dependent upon the ability of the plant to flower, to be pollinated and to set seed. In horticulture, control of the timing of flowering is important. Horticultural plants whose flowering may be controlled include lettuce, endive and vegetable brassicas including cabbage, broccoli and cauliflower, and carnations and geraniums.

*Arabidopsis thaliana* is a facultative long day plant, flowering early under long days and late under short days. Because it has a small, well-characterized genome, is relatively easily transformed and regenerated and has a rapid growing cycle, *Arabidopsis* is an ideal model plant in which to study flowering and its control.

In addition to cloning the VRN2 gene, the inventors have unexpectedly found indication that VRN2 is a transcription factor, which in itself opens several exciting avenues for application of the present invention. Without being bound by theory or in anyway limiting the scope of the present invention, VRN2 may be required for a normal vernalization response because it acts as a regulator of genes that ultimately lead to the transition from vegetative to reproductive growth. In such a model, cold, or a downstream molecule involved in cold perception, may regulate the activity or expression of the VRN2 protein, which in turn may regulate the expression of a large number of genes that ultimately lead to flowering. Furthermore, the shade avoidance phenotype exhibited by the vrn2-1 mutant, as demonstrated experimentally below, provides indication that VRN2 also plays a role in regulating leaf shape, particularly in response to increased far-red light. Together, these two processes affected by a deficiency or reduction of VRN2 activity provide for a number of approaches of agronomic interest.

First, forced expression of VRN2 (for example under the control of a strong and constitutive promoter, such as the CaMV 35 S promoter) in a wild-type background may be used alter the vernalization requirement of a plant prior to flowering. As a large number of commercial cultivars of several species, including (diploid) wheat, barley, and sugar beet, have a requirement for vernalization to flower, modification of this requirement, by reducing the duration of vernalization required, or changing the optimum temperature, or abrogating the requirement altogether, is of agronomic usefulness. For instance, a winter crop that can be sown and left in the ground for a shorter period than usual (i.e. a reduced vernalization time) may benefit from reduced risk of damage associated with severe winter weather conditions, as the crops are exposed to winter conditions for a shorter time.

Second, down-regulation of VRN2 expression, for instance by means of an antisense VRN2 cDNA, may be used to recapitulate the reduction in shade avoidance phenotype observed in vrn2-1 mutants. This may be used in situations where crowding of the crop is a problem. Based on experimental evidence provided herein on the phenotype of vrn2-1 mutants, such plants are expected to exhibit less of a response to such conditions, and to produce leaves that are essentially normal i.e. as if they had not been grown in dense or crowded conditions. The normal shade avoidance phenotype is a reduction in leaf size, which reduces shade in overcrowded conditions; vrn2-1 mutants, defective in VRN2 production, show less reduction in leaf size under conditions which would normally lead to the shade avoidance phenotype. This effect can therefore be reproduced for example by using antisense VRN2 cDNA to downregulate VRN2 expression, preventing or reducing the leaf avoidance response even in overcrowded conditions.

Third, the individual isolated domains of the VRN2 protein may be used in their own right. DNA binding of the zinc finger of VRN2 may be used to direct or control gene expression in a precise manner. The VRN2 zinc finger may recognize specific DNA sequences that represent elements in the promoters of its normal target genes. By creating fusion proteins, comprising the DNA binding (zinc finger) domain of VRN2, and an activation or repression domain from a heterologous protein, the expression of VRN2 target genes may be controlled. This allows for a precise control of the expression of those genes that are normally targets of VRN2. Given that such genes, alone or in combination, ultimately control the transition to flowering (usually following vernalization), their directed expression in other conditions may also be used to elicit changes in flowering and/or one or more other plant characteristics. The expression of (normally far-red responsive) target genes also be controlled using VRN2 fusion proteins containing the zinc finger of VRN2. Furthermore, the use of the zinc finger domain of VRN2 in conventional SELEX or one-hybrid experiments may be used to reveal the target genes or DNA sequences normally bound by VRN2.

The acidic activation domain of VRN2 may be used to regulate the activity of a fusion protein, including a DNA-binding protein of known specificity, and the activation domain of VRN2. This allows for regulation of target genes of other DNA binding proteins involved in flowering, or of target genes in completely unrelated processes.

The inventors have cloned, characterised and manipulated the VRN2 gene of *Arabidopsis thaliana*, both Columbia and Landsberg erecta types, and identified alternatively spliced and mutant forms, also homologues in other species.

In the light of the inventors' experimental work, a first aspect of the present invention provides a nucleic acid isolate encoding a polypeptide including a VRN2 amino acid sequence shown herein (e.g. SEQ ID NO: 2; SEQ ID NO: 5), which may include a coding sequence shown herein (e.g. SEQ ID NO: 1; SEQ ID NO: 4).

Allelic forms and alternatively spliced forms of the gene have been identified. Such polypeptides and encoding nucleic acid (e.g. as in SEQ ID NO: 8, encoded by SEQ ID NO: 7) are each further provided as an aspect of the invention, as are polypeptides and nucleic acid including the mutations identified herein.

Nucleic acid according to the present invention may have the sequence of the VRN2 gene of *Arabidopsis thaliana* as indicated in SEQ ID NO: 1, SEQ ID NO: 3 (*Landsberg erecta* genomic sequence), SEQ ID NO: 4 or SEQ ID NO: 6 (*Columbia* genomic sequence), or be a mutant, variant, derivative or allele or a homologue of the sequence provided. Preferred mutants, variants, derivatives and alleles are those which encode a protein which retains a functional characteristic of the protein encoded by the wild-type gene, especially the ability to alter vernalization response, flowering time, leaf shape and/or shade avoidance response.

A mutant, variant, derivative, allele or homologue in accordance with the present invention may have the ability to affect a physical characteristic of a plant, especially vernalization response, flowering time, leaf shape and/or shade avoidance response, as discussed.

Polynucleotides which are not 100% identical to the sequences shown herein but fall within the scope of the invention can be obtained in a number of ways.

Other VRN2 variants (for example allelic forms) of the gene described herein may be obtained for example by probing cDNA or genomic DNA libraries made from *Arabidopsis thaliana* plants or cells.

In addition, other plant, monocot or dicot, homologues of the gene may be obtained. Such sequences may be obtained by making or obtaining cDNA libraries made from dividing cells or tissues or genomic DNA libraries from other plant species, and probing such libraries with probes comprising all or part of a nucleic acid of the invention under conditions of medium to high stringency (for example for hybridization on a solid support (filter) overnight incubation at 42° C. in a solution containing 50% formamide, 5×SSC (750 mM NaCl, 75 mM sodium citrate), 50 mM sodium phosphate (pH7.6), 5× Denhardt's solution, 10% dextran sulphate and 20 μg/ml salmon sperm DNA, followed by washing in 0.03M sodium chloride and 0.03M sodium citrate (i.e. 0.2×SSC) at from about 50° C. to about 60° C.).

Thus the present invention provides an isolated nucleic acid which hybridizes to the nucleotide sequence shown in a figure herein under the abovementioned hybridization and washing conditions. Such a nucleic acid is suitable for use as a probe for detecting the VRN2 gene, for example in Southern blots.

Suitable probe and primer sequences are disclosed herein.

Alternatively, polynucleotides of the invention may be obtained by site directed mutagenesis of the sequences of shown in the figures or allelic variants thereof. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides. Further changes may be desirable to represent particular coding changes which are required to provide, for example, conservative substitutions.

In the context of cloning, it may be necessary for one or more gene fragments to be ligated to generate a full-length coding sequence. Also, where a full-length encoding nucleic acid molecule has not been obtained, a smaller molecule representing part of the full molecule, may be used to obtain full-length clones. Inserts may be prepared from partial cDNA clones and used to screen cDNA libraries. The full-length clones isolated may be subcloned into expression vectors and activity assayed by transfection into suitable host cells, e.g. with a reporter plasmid.

The present invention also extends to nucleic acid comprising transcriptional control sequences for the VRN2 gene. Such control sequences will be found 5' to the open reading frame of the gene and are obtainable by probing a genomic DNA library with a nucleic acid of the invention, selecting a clone which hybridizes under conditions of medium to high stringency, and sequencing the clone 5' to the open reading frame of the gene. Where only a small amount of sequence is present in the 5' region, this sequence may be used to reprobe the library to genome walk further upstream. Analysis of the upstream region will reveal control regions for gene expression including control regions common to many genes (i.e TATA and CAAT boxes) and other control regions, usually located from 1 to 10,000, such as 1 to 1000 or 50 to 500 nucleotides upstream of the start of transcription.

To confirm that such regions are the control regions of the gene, they may be linked to a reported gene (such as β-galactosidase) and tested in any suitable in vitro or in vivo system. For example the construct of the control region (e.g. comprising 50 to 500 nucleotides upstream of the start of transcription) and the reporter gene may be used to produce a transgenic plant and the pattern of expression, both spatially and developmentally, may be compared with that of the VRN2 gene. Where substantially similar patterns of expression are found, this shows that the construct comprises substantially all of the control region of the wild type gene.

SEQ ID NO: 3 and SEQ ID NO: 6 show the nucleotide sequence of the VRN2 genomic region including promoter, respectively for *Landsberg erecta* and *Columbia* ecotypes of *Arabidopsis thaliana*, also 3' regulatory elements.

The control region may be mutated to identify specific subregions responsible for transcriptional control. This may be achieved by a number of techniques well known in the art as such, including DNase protection footprint assays, in which the control region is brought into contact with an extract from a cell in which the VRN2 gene is actively expressed, and the regions of the control region which bind factors in that extract is determined.

Isolated nucleic acid comprising such control regions obtainable by such a method form a further aspect of the present invention.

The present invention further extends to genomic DNA exon sequences found between the introns encoding a VRN2 gene in plant. Such exon sequences may be obtained in a manner analogous to that described above for the transcriptional control sequences, with the appropriate genome walking being conducted between the intron sequences. The locations of the exons may be determined by comparing genomic and cDNA sequences of the gene, observing where the sequences line up and diverge, and looking for consensus splice sequences which define intron/exon boundaries.

As noted above, changes to a sequence, to produce a mutant, variant or derivative, may be by one or more of addition, insertion, deletion or substitution of one or more nucleotides in the nucleic acid, leading to the addition, insertion, deletion or substitution of one or more amino acids in the encoded polypeptide. Of course, changes to the nucleic acid which make no difference to the encoded amino acid sequence ("degeneratively equivalent") are included.

Preferred nucleic acid sequences according to the present invention are shown herein, for instance see SEQ ID NO: 1 and SEQ ID NO: 4, of which the respective predicted encoded amino acid sequences of polypeptides according to the present invention are shown in SEQ ID NO: 2 and SEQ ID NO: 5.

A mutant, allele, variant or derivative amino acid sequence in accordance with the present invention may include within a sequence shown herein a single amino acid change with respect to the sequence shown with the relevant SEQ ID NO: or in the relevant figure, or 2, 3, 4, 5, 6, 7, 8, or 9 changes, about 10, 15, 20, 30, 40 or 50 changes, or greater than about 50, 60, 70, 80 or 90 changes. In addition to one or more changes within the amino acid sequence shown in the relevant figure, a mutant, allele, variant or derivative amino acid sequence may include additional amino acids at the C-terminus and/or N-terminus.

A sequence related to a sequence specifically disclosed herein shares homology with that sequence. Homology may be at the nucleotide sequence and/or amino acid sequence level. Preferably, the nucleic acid and/or amino acid sequence shares homology with the coding sequence or the sequence encoded by a nucleotide sequence shown herein, for instance SEQ ID NO: 2 or SEQ ID NO: 5, preferably at least about 50%, or 60%, or 70%, or 80% homology, most preferably at least about 90%, 95%, 96%, 97%, 98% or 99% homology.

As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) *J. Mol. Biol.* 215: 403-10, which is in standard use in the art, or, and this may be preferred, either of the standard programs BestFit and GAP, which are part of the Wisconsin Package, Version 8, September 1994, (Genetics Computer Group, 575 Science Drive, Madison, Wis., USA, Wisconsin 53711). BestFit makes an optimal alignment of the best segment of similarity between two sequences. Optimal alignments are found by inserting gaps to maximize the number of matches using the local homology algorithm of Smith and Waterman (Advances in Applied Mathematics (1981) 2, pp. 482-489). GAP uses the Needleman and Wunsch algorithm to align two complete sequences that maximizes the number of matches and minimizes the number of gaps. Generally, the default parameters are used, with a gap creation penalty=12 and gap extension penalty=4.

Homology is generally over the full-length of the relevant sequence shown herein, that is unless stated otherwise, or it may be over a contiguous sequence of about or greater than about 20, 25, 30, 33, 40, 50, 67, 133, 167, 200, 233, 267, 300, 333, 400, 450, 500, 550, 600 or more amino acids or codons, compared with the relevant amino acid sequence or nucleotide sequence as the case may be.

In highly preferred embodiments, all percentage homologies referred to herein refer to percentage sequence identity.

In this context, percent (%) amino acid sequence identity with respect to a particular reference sequence is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity.

The % identity values used herein may be determined by WU-BLAST-2 which was obtained from [Altschul et al., *Methods in Enzymology,* 266: 460-480 (1996); blast.wustl/edu/blast/README.html]. WU-BLAST-2 uses several search parameters, most of which are set to default values. The adjustable parameters are set with the following values: overlap span=1, overlap fraction=0.125, word threshold (T)=11. The HSPS and HSPS2 parameters are dynamic values and are established by the program itself depending upon the composition of the particular sequence and composition of the particular database against which the sequence of interest is being searched; however, the values may be adjusted to increase sensitivity.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent (%) nucleic acid sequence identity with respect to a reference nucleic acid sequence is defined as the percentage of nucleotide residues in a candidate sequence that are identical with the nucleotide residues in the reference sequence. The identity values may be determined by the BLASTN module of WU-BLAST-2 set to the default parameters, with overlap span and overlap fraction set to 1 and 0.125, respectively.

Nucleic acid according to the present invention may consist essentially of or consist of the relevant coding sequence. Nucleic acid according to the present invention may include a promoter or other regulatory sequence as discussed further elsewhere herein, and such regulatory sequence may be heterologous to the coding sequence, that is to say not naturally operably linked therewith. Nucleic acid according to the present invention may be cDNA or lacking one or more introns which occur naturally, or may be in any non-naturally occurring form. A coding sequence in accordance with the present invention may be included with a larger nucleic acid molecule of less than about 10,000 nucleotides, less than about 5,000 nucleotides or less than about 2,000 nucleotides.

Also provided by an aspect of the present invention is nucleic acid including or consisting essentially of a sequence of nucleotides complementary to a nucleotide sequence hybridisable with any encoding sequence provided herein. Another way of looking at this would be for nucleic acid according to this aspect to be hybridisable with a nucleotide sequence complementary to any encoding sequence provided herein. Of course, DNA is generally double-stranded and blotting techniques such as Southern hybridisation are often performed following separation of the strands without a distinction being drawn between which of the strands is hybridising. Preferably the hybridisable nucleic acid or its complement encode a product able to influence a physical characteristic of a plant, particularly vernalization response, flowering time, leaf shape and/or shade avoidance response, e.g. in *Arabidopsis thaliana*. Preferred conditions for hybridisation are familiar to those skilled in the art, but are generally stringent enough for there to be positive hybridisation between the sequences of interest to the exclusion of other sequences.

The nucleic acid, which may contain for example DNA encoding a polypeptide including the amino acid sequence of VRN2 or other polypeptide disclosed herein, as genomic or cDNA, may be in the form of a recombinant and preferably replicable vector, for example a plasmid, cosmid, phage or *Agrobacterium* binary vector. The nucleic acid may be under the control of an appropriate promoter or other regulatory elements for expression in a host cell such as a microbial, e.g. bacterial, or plant cell. In the case of genomic DNA, this may contain its own promoter or other regulatory elements and in the case of cDNA this may be under the control of an appropriate promoter or other regulatory elements for expression in the host cell.

A vector including nucleic acid according to the present invention need not include a promoter or other regulatory sequence, particularly if the vector is to be used to introduce the nucleic acid into cells for recombination into the genome.

Those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Many known techniques and protocols for manipulation of nucleic acid, for example in preparation-of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference. Specific procedures and vectors previously used with wide success upon plants are described by Bevan (Nucl. Acids Res. 12, 8711-8721 (1984)) and Guerineau and Mullineaux (1993) (Plant transformation and expression vectors. In: Plant Molecular Biology Labfax (Croy RRD ed) Oxford, BIOS Scientific Publishers, pp 121-148).

Selectable genetic markers may be used consisting of chimaeric genes that confer selectable phenotypes such as resistance to antibiotics such as kanamycin, hygromycin, phosphinotricin, chlorsulfuron, methotrexate, gentamycin, spectinomycin, imidazolinones and glyphosate.

Nucleic acid molecules and vectors according to the present invention may be provided isolated and/or purified from their natural environment, in substantially pure or homogeneous form, or free or substantially free of nucleic acid or genes of the species of interest or origin other than the sequence encoding a polypeptide with the required function. Nucleic acid according to the present invention may include cDNA, RNA, genomic DNA and may be wholly or partially synthetic. The term "isolate" encompasses all these possibilities. Where a DNA sequence is specified, e.g. with reference to a figure, unless context requires otherwise the RNA equivalent, with U substituted for T where it occurs, is encompassed.

When introducing a chosen gene construct into a cell, certain considerations must be taken into account, well known to those skilled in the art. The nucleic acid to be inserted should be assembled within a construct which contains effective regulatory elements which will drive transcription. There must be available a method of transporting the construct into the cell. Once the construct is within the cell membrane, integration into the endogenous chromosomal material either will or will not occur. Finally, as far as plants are concerned the target cell type must be such that cells can be regenerated into whole plants.

Plants transformed with the DNA segment containing the sequence may be produced by standard techniques which are already known for the genetic manipulation of plants. DNA can be transformed into plant cells using any suitable technology, such as a disarmed Ti-plasmid vector carried by *Agrobacterium* exploiting its natural gene transfer ability (EP-A-270355, EP-A-0116718, NAR 12(22) 8711-87215 1984), particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv.* 9: 1-11.

*Agrobacterium* transformation is widely used by those skilled in the art to transform dicotyledonous species. There are various approaches used for the routine production of stable, fertile transgenic plants in almost all economically relevant monocot plants (Toriyama, et al. (1988) *Bio/Technology* 6, 1072-1074; Zhang, et al. (1988) *Plant Cell Rep.* 7, 379-384; Zhang, et al. (1988) *Theor Appl Genet* 76, 835-840; Shimamoto, et al. (1989) *Nature* 338, 274-276; Datta, et al. (1990) *Bio/Technology* 8, 736-740; Christou, et al. (1991) *Bio/Technology* 9, 957-962; Peng, et al. (1991) International Rice Research Institute, Manila, Philippines 563-574; Cao, et al. (1992) *Plant Cell Rep.* 11, 585-591; Li, et al. (1993) *Plant Cell Rep.* 12, 250-255; Rathore, et al. (1993) *Plant Molecular Biology* 21, 871-884; Fromm, et al. (1990) *Bio/Technology* 8, 833-839; Gordon-Kamm, et al. (1990) *Plant Cell* 2, 603-618; D'Halluin, et al. (1992) *Plant Cell* 4, 1495-1505; Walters, et al. (1992) *Plant Molecular Biology* 18, 189-200; Koziel, et al. (1993) *Biotechnology* 11, 194-200; Vasil, I. K. (1994) *Plant Molecular Biology* 25, 925-937; Weeks, et al. (1993) *Plant Physiology* 102, 1077-1084; Somers, et al. (1992) *Bio/Technology* 10, 1589-1594; WO92/14828). In particular, *Agrobacterium* mediated transformation is now emerging also as an highly efficient alternative transformation method in monocots (Hiei et al. (1994) *The Plant Journal* 6, 271-282).

The generation of fertile transgenic plants has been achieved in the cereals rice, maize, wheat, oat, and barley (reviewed in Shimamoto, K. (1994) *Current Opinion in Biotechnology* 5, 158-162.; Vasil, et al. (1992) *Bio/Technology* 10, 667-674; Vain et al., 1995, *Biotechnology Advances* 13 (4): 653-671; Vasil, 1996, *Nature Biotechnology* 14 page 702).

Microprojectile bombardment, electroporation and direct DNA uptake are preferred where *Agrobacterium* is inefficient or ineffective. Alternatively, a combination of different techniques may be employed to enhance the efficiency of the transformation process, eg bombardment with *Agrobacterium* coated microparticles (EP-A-486234) or microprojectile bombardment to induce wounding followed by co-cultivation with *Agrobacterium* (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

A VRN2 gene and modified versions thereof (alleles, mutants, variants and derivatives thereof), and other nucleic acid provided herein, including species homologues, may be used to modify vernalization response, flowering time, leaf shape and/or shade avoidance response in a transgenic plant. Nucleic acid such as a vector as described herein may be used for the production of a transgenic plant. Such a plant may possess an altered phenotype, particular in terms of vernalization response, flowering time, leaf shape and/or shade avoidance response compared with wild-type (that is to say a plant that is wild-type for VRN2 or the relevant homologue thereof).

The invention further encompasses a host cell transformed with nucleic acid or a vector according to the present invention, especially a plant or a microbial cell. Thus, a host cell, such as a plant cell, including heterologous nucleic acid according to the present invention is provided. Within the cell, the nucleic acid may be incorporated within the chromosome. There may be more than one heterologous nucleotide sequence per haploid genome.

Also according to the invention there is provided a plant cell having incorporated into its genome nucleic acid, particularly heterologous nucleic acid, as provided by the present invention, under operative control of a regulatory sequence for control of expression. The coding sequence may be operably linked to one or more regulatory sequences which may be heterologous or foreign to the gene, such as not naturally associated with the gene for its expression. The nucleic acid according to the invention may be placed under the control of an externally inducible gene promoter to place expression under the control of the user.

A suitable inducible promoter is the GST-II-27 gene promoter which has been shown to be induced by certain chemical compounds which can be applied to growing plants. The promoter is functional in both monocotyledons and dicotyledons. It can therefore be used to control gene expression in a variety of genetically modified plants, including field crops such as canola, sunflower, tobacco, sugarbeet, cotton; cereals such as wheat, barley, rice, maize, sorghum; fruit such as tomatoes, mangoes, peaches, apples, pears, strawberries, bananas, and melons; and vegetables such as carrot, lettuce, cabbage and onion. The GST-II-27 promoter is also suitable for use in a variety of tissues, including roots, leaves, stems and reproductive tissues.

A further aspect of the present invention provides a method of making such a plant cell involving introduction of nucleic acid or a suitable vector including the sequence of nucleotides into a plant cell and causing or allowing recombination between the vector and the plant cell genome to introduce the sequence of nucleotides into the genome. The invention extends to plant cells containing nucleic acid according to the invention as a result of introduction of the nucleic acid into an ancestor cell.

The term "heterologous" may be used to indicate that the gene/sequence of nucleotides in question have been introduced into said cells of the plant or an ancestor thereof, using genetic engineering, ie by human intervention. A transgenic plant cell, i.e. transgenic for the nucleic acid in question, may be provided. The transgene may be on an extra-genomic vector or incorporated, preferably stably, into the genome. A heterologous gene may replace an endogenous equivalent gene, ie one which normally performs the same or a similar function, or the inserted sequence may be additional to the endogenous gene or other sequence. An advantage of introduction of a heterologous gene is the ability to place expression of a sequence under the control of a promoter of choice, in order to be able to influence expression according to preference. Furthermore, mutants, variants and derivatives of the wild-type gene, e.g. with higher or lower activity than wild-type, may be used in place of the endogenous gene. Nucleic acid heterologous, or exogenous or foreign, to a plant cell may be non-naturally occuring in cells of that type, variety or species. Thus, nucleic acid may include a coding sequence of or derived from a particular type of plant cell or species or variety of plant, placed within the context of a plant cell of a different type or species or variety of plant. A further possibility is for a nucleic acid sequence to be placed within a cell in which it or a homologue is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression. A sequence within a plant or other host cell may be identifiably heterologous, exogenous or foreign.

Plants which include a plant cell according to the invention are also provided, along with any part or propagule thereof, seed, selfed or hybrid progeny and descendants. A plant according to the present invention may be one which does not breed true in one or more properties. Plant varieties may be excluded, particularly registrable plant varieties according to Plant Breeders' Rights. It is noted that a plant need not be considered a "plant variety" simply because it contains stably within its genome a transgene, introduced into a cell of the plant or an ancestor thereof.

In addition to a plant, the present invention provides any clone of such a plant, seed, selfed or hybrid progeny and descendants, and any part of any of these, such as cuttings, seed. The invention provides any plant propagule, that is any part which may be used in reproduction or propagation, sexual or asexual, including-cuttings, seed and so on. Also encompassed by the invention is a plant which is a sexually or asexually propagated off-spring, clone or descendant of such a plant, or any part or propagule of said plant, off-spring, clone or descendant.

The invention further provides a method of influencing or affecting a physical characteristic of a plant, particularly vernalization response, flowering time, leaf shape and/or shade-avoidance response, including causing or allowing expression of a heterologous nucleic acid sequence as discussed within cells of the plant.

The invention further provides a method of inducing expression from nucleic acid encoding a VRN2 polypeptide, or a mutant, variant, allele or derivative of the sequence, or a homologue, according to the disclosure herein, within cells of a plant (thereby producing the encoded polypeptide), following an earlier step of introduction of the nucleic acid into a cell of the plant or an ancestor thereof. Such a method may influence or affect a characteristic of the plant, such as vernalization response, flowering time, leaf shape and/or shade avoidance response. This may be used in combination with any other gene, such as transgenes involved in flowering (e.g. FCA) or other phenotypic trait or desirable property.

The present invention also encompasses the expression product of any of the nucleic acid sequences disclosed and methods of making the expression product by expression from encoding nucleic acid therefore under suitable conditions, which may be in suitable host cells. Following expression, the product may be isolated from the expression system and may be used as desired, for instance in formulation of a composition including at least one additional component.

The present invention also provides for the production and use of fragments of the full-length polypeptides disclosed herein, especially active portions thereof. An "active portion" of a polypeptide means a peptide which is less than said full length polypeptide, but which retains an essential biological activity. In particular, the active portion retains the ability to alter vernalization response, flowering time, leaf shape and/or shade avoidance response in a plant, such as Arabidopsis thaliana.

A "fragment" of a polypeptide means a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids. Fragments of the polypeptides may include one or more epitopes useful for raising antibodies to a portion of any of the amino acid sequences disclosed herein. Preferred epitopes are those to which antibodies are able to bind specifically, which may be taken to be binding a polypeptide or fragment thereof of the invention with an affinity which is at least about 1000× that of other polypeptides.

Among preferred VRN2 fragments according to the present invention are the zinc finger domain, DNA binding domain and other domains disclosed herein.

Purified protein according to the present invention, or a fragment, mutant, derivative or variant thereof, e.g. produced recombinantly by expression from encoding nucleic acid therefor, may be used to raise antibodies employing techniques which are standard in the art. Antibodies and polypeptides comprising antigen-binding fragments of antibodies may be used in identifying homologues from other species as discussed further below, also in identifying complexes containing VRN2 protein.

Methods of producing antibodies include immunising a mammal (e.g. human, mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest. For instance, Western blotting techniques or immunoprecipitation may be used (Armitage et al, 1992, Nature 357: 80-82). Antibodies may be polyclonal or monoclonal.

As an alternative or supplement to immunising a mammal, antibodies with appropriate binding specificity may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Antibodies raised to a polypeptide or peptide can be used in the identification and/or isolation of homologous polypeptides, and then the encoding genes. Thus, the present invention provides a method of identifying or isolating a polypeptide with the desired function (in accordance with embodiments disclosed herein), comprising screening candidate polypeptides with a polypeptide comprising the antigen-binding domain of an antibody (for example whole antibody or a suitable fragment thereof, e.g. scFv, Fab) which is able to bind a polypeptide or fragment, variant or derivative thereof according to the present invention or preferably has binding specificity for such a polypeptide. Specific binding members such as antibodies and polypeptides comprising antigen binding domains of antibodies that bind and are preferably specific for a polypeptide or mutant, variant or derivative thereof according to the invention represent further aspects of the present invention, particularly in isolated and/or purified form, as do their use and methods which employ them.

Candidate polypeptides for screening may for instance be the products of an expression library created using nucleic acid derived from an plant of interest, or may be the product of a purification process from a natural source. A polypeptide found to bind the antibody may be isolated and then may be subject to amino acid sequencing. Any suitable technique may be used to sequence the polypeptide either wholly or partially (for instance a fragment of the polypeptide may be sequenced). Amino acid sequence information may be used in obtaining nucleic acid encoding the polypeptide, for instance by designing one or more oligonucleotides (e.g. a degenerate pool of oligonucleotides) for use as probes or primers in hybridization to candidate nucleic acid, or by searching computer sequence databases, as discussed further below.

A further aspect of the present invention provides a method of identifying and cloning VRN2 homologues from plant species other than Arabidopsis thaliana which method employs a nucleotide sequence derived from that shown herein. As discussed above, sequences derived from these may themselves be used in identifying and in cloning other sequences. The nucleotide sequence information provided herein, or any part thereof, may be used in a data-base search to find homologous sequences, expression products of which can be tested for ability to influence a plant characteristic. These may have ability to alter vernalization response, flowering time, leaf shape and/or shade avoidance response in a plant. Alternatively, nucleic acid libraries may be screened using techniques well known to those skilled in the art and homologous sequences thereby identified then tested.

The present invention also extends to nucleic acid encoding a VRN2 homologue obtained using a nucleotide sequence derived from any of those shown herein.

In certain embodiments, nucleic acid according to the present invention encodes a polypeptide which has homology with all or part of VRN2 amino acid sequence shown herein, in the terms discussed already above (e.g. for length), which homology is greater over the length of the relevant part (i.e. fragment) than the homology shared between a respective part of the VRN2 amino acid sequence of *Arabidopsis thaliana*, and the other sequences shown in FIG. 8a or FIG. 8b, and may be greater than about 5% greater, more preferably greater than about 10% greater, more preferably greater than about 20% greater, and more preferably greater than about 30% greater. Thus, to exemplify with reference to one embodiment, nucleic acid encoding an amino acid mutant, variant or derivative of the amino-acid sequence shown in SEQ ID NO: 2 may be provided wherein the encoded amino acid sequence includes a contiguous sequence of about 100 amino acids which has greater homology with a contiguous sequence of 100 amino acids within the amino acid sequence of SEQ ID NO: 2 than any contiguous sequence of 100 amino acids within another sequence shown in FIG. 8a or 8b, preferably greater than about 5% greater homology, and so on.

Similarly, nucleic acid according to certain embodiments of the present invention may have homology with all or part of a nucleotide sequence shown herein, in the terms discussed already above (e.g. for length), which homology is greater over the length of the relevant part (i.e. fragment) than the homology shared with a respective part of the natural coding nucleotide sequence for the other amino acid sequences shown in FIG. 8a or 8b and referenced herein, and may be greater than about 5% greater, more preferably greater than about 10% greater, more preferably greater than about 20% greater, and more preferably greater than about 30% greater.

The provision of sequence information for the VRN2 gene of *Arabidopsis thaliana* enables the obtention of homologous sequences from other plant species. In particular, homologues may be easily isolated from related, commercially important species that have a vernalization requirement, or show some response to vernalization. These would include all members of the Brassicaceae, and other dicots including tobacco, sugarbeet, peas and celery. Monocots included in this category are the cereals rice, wheat and barley.

Thus, included within the scope of the present invention are nucleic acid molecules which encode amino acid sequences which are homologues of VRN2 of *Arabidopsis thaliana*. Homology may be at the nucleotide sequence and/or amino acid sequence level, as has already been discussed above. A homologue from a species other than *Arabidopsis thaliana* encodes a product which causes a phenotype similar to that caused by the VRN2 gene, generally including ability to alter vernalization response, flowering time, leaf shape and/or shade avoidance response in a plant, such as in *Arabidopsis thaliana*. In addition, mutants, derivatives or alleles of these genes may have altered, e.g. increased or decreased, activity or ability compared with wild-type.

VRN2 gene homologues may also be identified from economically important monocotyledonous crop plants including the cereals rice, wheat and barley. Although genes encoding the same protein in monocotyledonous and dicotyledonous plants show relatively little homology at the nucleotide level, amino acid sequences are conserved. Therefore it is possible to use public sequence databases to identify *Arabidopsis*, rice or maize cDNA clone sequences that were obtained in random sequencing programmes and share homology to the gene of interest, as has been done for other genes isolated from *Arabidopsis* (e.g CO; WO 96/14414). Of course, mutants, derivatives and alleles of these sequences are included within the scope of the present invention in the same terms as discussed above for the *Arabidopsis thaliana* VRN2 gene.

According to a further aspect, the present invention provides a method of identifying or a method of cloning a VRN2 homologue, e.g. from a species other than *Arabidopsis thaliana* the method employing a nucleotide sequence derived from any of those shown herein. For instance, such a method may employ an oligonucleotide or oligonucleotides which comprises or consists of a sequence or sequences conserved between or encoding a sequence or sequences conserved between the sequences shown in FIG. 8a or 8b, or a sequence or sequences conserved between the sequences of SEQ ID NO: 2 and SEQ ID NO: 5, or encoding sequences SEQ ID NO: 1 and SEQ ID NO: 4, to search for homologues. Thus, a method of obtaining nucleic acid is provided, comprising hybridisation of an oligonucleotide or a nucleic acid molecule comprising such an oligonucleotide to target/candidate nucleic acid. Target or candidate nucleic acid may, for example, comprise a genomic or cDNA library obtainable from an organism known to contain or suspected of containing such nucleic acid, either monocotyledonous or dicotyledonous. Successful hybridisation may be identified and target/candidate nucleic acid isolated for further investigation and/or use.

Hybridisation may involve probing nucleic acid and identifying positive hybridisation under suitably stringent conditions (in accordance with known techniques) and/or use of oligonucleotides as primers in a method of nucleic acid amplification, such as PCR. For probing, preferred conditions are those which are stringent enough for there to be a simple pattern with a small number of hybridisations identified as positive which can be investigated further. It is well known in the art to increase stringency of hybridisation gradually until only a few positive clones remain.

For instance, screening may initially be carried out under conditions, which comprise a temperature of about 37° C. or more, a formamide concentration of less than about 50%, and a moderate to low salt (e.g. Standard Saline Citrate ('SSC')=0.15 M sodium chloride; 0.15 M sodium citrate; pH 7) concentration.

Alternatively, a temperature of about 50° C. or more and a high salt (e.g. 'SSPE'=0.180 M sodium chloride; 9 mM disodium hydrogen phosphate; 9 mM sodium dihydrogen phosphate; 1 mM sodium EDTA; pH 7.4). Preferably the screening is carried out at about 37° C., a formamide concentration of about 20%, and a salt concentration of about 5×SSC, or a temperature of about 50° C. and a salt concentration of about 2×SSPE. These conditions will allow the identification of sequences which have a substantial degree of homology (similarity, identity) with the probe sequence, without requiring the perfect homology for the identification of a stable hybrid.

Suitable conditions include, e.g. for detection of sequences that are about 80-90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M Na$_2$HPO$_4$, pH 7.2, 6.5% SDS, 10% dextran sulfate and a final wash at 60° C. in 0.1×SSC, 0.1% SDS.

An alternative is a solution of 5×SSPE (final 0.9 M NaCl, 0.05M sodium phosphate, 0.005M ethylenediamnetetraacetic acid (EDTA) pH 7.7), 5× Denhardt's solution, 0.5% SDS (sodium dodecyl sulphate), at 65° C. overnight, (for high stringency, highly similar sequences) or 50° C. (for low stringency, less similar sequences). Washes in 0.2×SSC/ 0.1% SDS at 65° C. for high stringency, alternatively at 50-60° C. in 1×SSC/0.1% SDS for low stringency.

The present invention extends to nucleic acid selectively hybridisable under high stringency with nucleic acid identified herein.

As an alternative to probing, though still employing nucleic acid hybridisation, oligonucleotides designed to amplify DNA sequences may be used in PCR reactions or other methods involving amplification of nucleic acid, using routine procedures. See for instance "PCR protocols; A Guide to Methods and Applications", Eds. Innis et al, 1990, Academic Press, New York.

Preferred amino acid sequences suitable for use in the design of probes or PCR primers for some purposes are sequences conserved (completely, substantially or partly) between the VRN2 sequence and at least one other of the sequences shown in FIG. 8a or 8b.

Preferred primers for amplification of conserved regions of VRN2 for use as probes to obtain genomic or cDNA clones may include the following:

Primers VRN2-AI and VRN2-AJ which, in RT-PCR, amplify a 1583 bp fragment that contains the complete VRN2 open reading frame, and portions of both the 5' and 3' untranslated sequences;

Primers VRN2-AP and VRN2-AJ which, in RT-PCR, amplify a 781 bp fragment that includes the conserved acidic region;

Primers VRN2-AO and VRN2-AS which, in RT-PCR, amplify a 493 bp fragment that includes the zinc-finger motif, and the second nuclear localization signal (NLS); and Primers VRN2-AI and VRN2-AJ from genomic DNA, which amplify a 3605 bp product that includes most of the VRN2 gene, except the promoter and 3' regions (i.e. encompasses the same regions as-the VRN2-AI/AJ pair above, but with the introns, useful for hybridisation to genomic DNA, less so for cDNA).

On the basis of amino acid sequence information oligonucleotide probes or primers may be designed, taking into account the degeneracy of the genetic code, and, where appropriate, codon usage of the organism from which the candidate nucleic acid is derived.

Preferably an oligonucleotide in accordance with certain embodiments of the invention, e.g. for use in nucleic acid amplification, is up to about 50 nucleotides, or about 40 nucleotides or about 30 or fewer nucleotides in length (e.g. 18, 21 or 24).

Assessment of whether or not such a PCR product corresponds to a homologue gene may be conducted in various ways. A PCR band from such a reaction might contain a complex mix of products. Individual products may be cloned and each one individually screened. It may be analysed by transformation to assess function on introduction into a plant of interest.

As noted, nucleic acid according to the present invention is obtainable using oligonucleotides, designed on the basis of sequence information provided herein, as probes or primers. Nucleic acid isolated and/or purified from one or more cells of a plant (see above), or a nucleic acid library derived from nucleic acid isolated and/or purified from the plant (e.g. a cDNA library derived from mRNA isolated from the plant), may be probed under conditions for selective hybridisation and/or subjected to a specific nucleic acid amplification reaction such as the polymerase chain reaction (PCR). The nucleic acid probed or used as template in the amplification reaction may be genomic DNA, cDNA or RNA. If necessary, one or more gene fragments may be ligated to generate a full-length coding sequence.

PCR primers derived from the VRN2 sequences disclosed herein may readily be tested for their specificity for amplifying nucleic acid according to the present invention, using both genomic DNA and RT-PCR templates. Cloning and subsequent sequencing of PCR products may be used to indicate amplification of the expected derived gene fragment. Full length cDNA clones can be obtained as described by 5' and 3' RACE technology if RT-PCR products are used as templates.

Various aspects of the present invention include the obtainable nucleic acid, methods of screening material, e.g. cell lysate, nucleic acid preparations, for the presence of nucleic acid of interest, methods of obtaining the nucleic acid, and suitable primers and primer combinations.

The sequence information provided herein also allows the design of diagnostic tests for determination of the presence of a specific gene or allele thereof in any given plant, cultivar, variety, population, landrace, part of a family or other selection in a breeding programme or other such genotype. A diagnostic test may be based on determination of the presence or absence of a particular allele by means of nucleic acid or polypeptide determination.

At the nucleic acid level, this may involve hybridisation of a suitable oligo- or poly-nucleotide, such as a fragment of the gene or a homologue thereof, including any homologue disclosed herein, or any particular allele, such as an allele which gives a desirable phenotype, such as any such allele disclosed herein. The hybridisation may involve PCR designed to amplify a product from a given allelic version of the gene, with subsequent detection of an amplified product by any of a number of possible methods including but not limited to gel electrophoresis, capillary electrophoresis, direct hybridisation of nucleotide sequence probes and so on. A diagnostic test may be based on PCR designed to amplify various alleles or any allele from the relevant locus, with a test to distinguish the different possible alleles by any of a number of possible methods, including DNA fragment size, restriction site variation (e.g. CAPS—cleaved amplified polymorphic sites) and so on. A diagnostic test may also be based on a great number of possible variants of nucleic acid analysis that will be apparent to those skilled in the art, such as use of a synthetic sequence as a hybridisation probe.

Broadly, the methods divide into those screening for the presence of nucleic acid sequences and those that rely on detecting the presence or absence of a polypeptide. The methods may make use of biological samples from one or more plants or cells that are suspected to contain the nucleic acid sequences or polypeptide.

Exemplary approaches for detecting nucleic acid or polypeptides include analysing a sample from the plant or plant cell by:

(a) comparing the sequence of nucleic acid in the sample with all or part of a nucleotide sequence shown herein, to determine whether the sample contains a mutation;

(b) determining the presence in the sample of a polypeptide including a VRN2 amino acid sequence shown herein, or a fragment thereof and, if present, determining whether the polypeptide is full length, and/or is mutated, and/or is expressed at the normal level;

(c) performing DNA fingerprinting to compare the restriction pattern produced when a restriction enzyme cuts nucleic acid in the sample with the restriction pattern obtained from a nucleotide sequence shown herein, or from a known mutant, allele or variant thereof;

(d) contacting the sample with a specific binding member capable of binding to nucleic acid including the nucleotide sequence as set out herein, or a fragment thereof, or a mutant, allele or variant thereof, the specific binding member including nucleic acid hybridisable with a VRN2 sequence herein, or a polypeptide including a binding domain with specificity for nucleic acid including a VRN2 sequence or polypeptide encoded by it, or a mutated form thereof, and determining binding of the specific binding member;

(e) performing PCR involving one or more primers based on a nucleotide sequence shown herein to screen the sample for nucleic acid including the nucleotide sequence of SEQ ID NO: 1 or SEQ ID NO: 4 or a mutant, allele or variant thereof.

When screening for a VRN2 allele nucleic acid, the nucleic acid in the sample will initially be amplified, e.g. using PCR, to increase the amount of the analyte as compared to other sequences present in the sample. This allows the target sequences to be detected with a high degree of sensitivity if they are present in the sample. This initial step may be avoided by using highly sensitive array techniques that are becoming increasingly important in the art.

A variant form of the gene may contain one or more insertions, deletions, substitutions and/or additions of one or more nucleotides compared with the wild-type sequence which may or may not disrupt or alter the gene function. Differences at the nucleic acid level are not necessarily reflected by a difference in the amino acid sequence of the encoded polypeptide. However, a mutation or other difference in a gene may result in a frame-shift or stop codon, which could seriously affect the nature of the polypeptide produced (if any), or a point mutation or gross mutational change to the encoded polypeptide, including insertion, deletion, substitution and/or addition of one or more amino acids or regions in the polypeptide. A mutation in a promoter sequence or other regulatory region may prevent or reduce, expression from the gene or affect the processing or stability of the mRNA transcript.

Tests may be carried out on preparations containing genomic DNA, cDNA and/or mRNA. Testing cDNA or mRNA has the advantage of the complexity of the nucleic acid being reduced by the absence of intron sequences, but the possible disadvantage of extra time and effort being required in making the preparations. RNA is more difficult to manipulate than DNA because of the wide-spread occurrence of RN'ases.

Nucleic acid in a test sample may be sequenced and the sequence compared with a sequence shown herein to determine whether or not a difference is present. If so, the difference can be compared with known alleles to determine whether the test nucleic acid contains one or more of the variations indicated, or the difference can be investigated for association with a desired phenotype.

The amplified nucleic acid may then be sequenced as above, and/or tested in any other way to determine the presence or absence of a particular feature. Nucleic acid for testing may be prepared from nucleic acid removed from cells or in a library using a variety of other techniques such as restriction enzyme digest and-electrophoresis.

Nucleic acid may be screened using a variant- or allele-specific probe. Such a probe corresponds in sequence to a region of the gene, or its complement, containing a sequence alteration known to be associated with alteration of ability to affect vernalization response, flowering time, leaf shape and/or shade avoidance response. Under suitably stringent conditions, specific hybridisation of such a probe to test nucleic acid is indicative of the presence of the sequence alteration in the test nucleic acid. For efficient screening purposes, more than one probe may be used on the same test sample.

Allele- or variant-specific oligonucleotides may similarly be used in PCR to specifically amplify particular sequences if present in a test sample. Assessment of whether a PCR band contains a gene variant may be carried out in a number of ways familiar to those skilled in the art. The PCR product may for instance be treated in a way that enables one to display the mutation or polymorphism on a denaturing polyacrylamide DNA sequencing gel, with specific bands that are linked to the gene variants being selected.

An alternative or supplement to looking for the presence of variant sequences in a test sample is to look for the presence of the normal sequence, e.g. using a suitably specific oligonucleotide probe or primer.

Approaches which rely on hybridisation between a probe and test nucleic acid and subsequent detection of a mismatch may be employed. Under appropriate conditions (temperature, pH etc.), an oligonucleotide probe will hybridise with a sequence which is not entirely complementary. The degree of base-pairing between the two molecules will be sufficient for them to anneal despite a mis-match. Various approaches are well known in the art for detecting the presence of a mis-match between two annealing nucleic acid molecules.

For instance, RNase A cleaves at the site of a mis-match. Cleavage can be detected by electrophoresing test nucleic acid to which the relevant probe or probe has annealed and looking for smaller molecules (i.e. molecules with higher electrophoretic mobility) than the full length probe/test hybrid. Other approaches rely on the use of enzymes such as resolvases or endonucleases.

Thus, an oligonucleotide probe that has the sequence of a region of the normal gene (either sense or anti-sense strand) in which mutations associated with particular phenotypes are known to occur may be annealed to test nucleic acid and the presence or absence of a mis-match determined. Detection of the presence of a mis-match may indicate the presence in the test nucleic acid of a mutation. On the other hand, an oligonucleotide probe that has the sequence of a region of the gene including a mutation may be annealed to test nucleic acid and the presence or absence of a mis-match determined. The presence of a mis-match may indicate that the nucleic acid in the test sample has the normal sequence, or a different mutant or allele sequence. In either case, a battery of probes to different regions of the gene may be employed.

The presence of differences in sequence of nucleic acid molecules may be detected by means of restriction enzyme digestion, such as in a method of DNA fingerprinting where the restriction pattern produced when one or more restriction enzymes are used to cut a sample of nucleic acid is compared with the pattern obtained when a sample containing the normal gene or a variant or allele is digested with the same enzyme or enzymes.

The presence of absence of a lesion in a promoter or other regulatory sequence may also be assessed by determining the level of mRNA production by transcription or the level of polypeptide production by translation from the mRNA.

Nucleic acid isolated and/or purified from one or more cells of a plant or a nucleic acid library derived from nucleic acid isolated and/or purified from cells (e.g. a cDNA library derived from mRNA isolated from the cells), may be probed under conditions for selective hybridisation and/or subjected to a specific nucleic acid amplification reaction such as the polymerase chain reaction (PCR).

A method may include hybridisation of one or more (e.g. two) probes or primers to target nucleic acid. Where the nucleic acid is double-stranded DNA, hybridisation will generally be preceded by denaturation to produce single-stranded DNA. The hybridisation may be as part of a PCR procedure, or as part of a probing procedure not involving PCR. An example procedure would be a combination of PCR and low stringency hybridisation. A screening procedure, chosen from the many available to those skilled in the art, is used to identify successful hybridisation events and isolate hybridised nucleic acid.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RNAase cleavage and allele specific oligonucleotide probing.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells.

Preliminary experiments may be performed by hybridising under low stringency conditions various probes to Southern blots of DNA digested with restriction enzymes. Suitable conditions would be achieved when a large number of hybridising fragments were obtained while the background hybridisation was low. Using these conditions nucleic acid libraries, e.g. cDNA libraries representative of expressed sequences, may be searched.

As noted, those skilled in the art are well able to employ suitable conditions of the desired stringency for selective hybridisation, taking into account factors such as oligonucleotide length and base composition, temperature and so on.

In some preferred embodiments of diagnostic assays according to the present invention, oligonucleotides according to the present invention that are fragments of any of the sequences shown herein, or any allele associated with a desired phenotype are at least about 10 nucleotides in length, more preferably at least about 15 nucleotides in length, more preferably at least about 20 nucleotides in length, more preferably about 30 nucleotides in length. Such fragments themselves individually represent aspects of the present invention. Fragments and other oligonucleotides may be used as primers or probes as discussed but may also be generated (e.g. by PCR) in methods concerned with determining the presence in a test sample of a sequence indicative of a desired phenotype.

There are various methods for determining the presence or absence in a test sample of a particular polypeptide, such as a polypeptide including the amino acid sequence shown in SEQ ID NO: 2 or SEQ ID NO: 5, or an amino acid sequence mutant, variant or allele thereof.

A sample may be tested for the presence of a binding partner for a specific binding member such as an antibody (or mixture of antibodies), specific for one or more particular variants of a polypeptide shown herein.

In such cases, the sample may be tested by being contacted with a specific binding member such as an antibody under appropriate conditions for specific binding, before binding is determined, for instance using a reporter system as discussed. Where a panel of antibodies is used, different reporting labels may be employed for each antibody so that binding of each can be determined.

A specific binding member such as an antibody may be used to isolate and/or purify its binding partner polypeptide from a test sample, to allow for sequence and/or biochemical analysis of the polypeptide to determine whether it has the sequence and/or properties of the wild-type polypeptide or a particular mutant, variant or allele thereof. Amino acid sequence is routine in the art using automated sequencing machines.

The use of diagnostic tests for alleles allows the researcher or plant breeder to-establish, with full confidence and independent from time consuming biochemical tests, whether or not a desired allele is present in the plant of interest (or a cell thereof), whether the plant is a representative of a collection of other genetically identical plants (e.g. an inbred variety or cultivar) or one individual in a sample of related (e.g. breeders' selection) or unrelated plants.

In a breeding scheme based on selection and selfing of desirable individuals, nucleic acid or polypeptide diagnostics for the desirable allele or alleles in high throughput, low cost assays as provided by this invention, reliable selection for the can be made at early generations and on more material than would otherwise be possible. This gain in reliability of selection plus the time saving by being able to test material earlier and without costly phenotype screening is of considerable value in plant breeding.

Nucleic acid-based determination of the presence or absence of one or more desirable alleles may be combined with determination of the genotype of the flanking linked genomic DNA and other unlinked genomic DNA using established sets of markers such as RFLPs, microsatellites or SSRs, AFLPs, RAPDs etc. This enables the researcher or plant breeder to select for not only the presence of the desirable allele but also for individual plant or families of plants which have the most desirable combinations of linked and unlinked genetic background. Such recombinations of desirable material may occur only rarely within a given segregating breeding population or backcross progeny. Direct assay of the locus as afforded by the present invention allows the researcher to make a stepwise approach to fixing (making homozygous) the desired combination of flanking markers and alleles, by first identifying individuals fixed for one flanking marker and then identifying progeny fixed on the other side of the locus all the time knowing with confidence that the desirable allele is still present.

The present disclosure provides sufficient information for a person skilled in the art to obtain genomic DNA sequence for any given new or existing allele and devise a suitable nucleic acid- and/or polypeptide-based diagnostic assay. In designing a nucleic acid assay account is taken of the distinctive variation in sequence that characterises the particular variant allele.

Nucleic acid according to the invention may include a nucleotide sequence encoding a product involved in vernalization response, flowering time, leaf shape and/or shade avoidance response. Reducing or increasing the level of expression may be used to manipulate such a characteristic in a plant. This may involve use of anti-sense or sense regulation, discussed further below.

Nucleic acid according to the invention, such as a VRN2 gene or homologue, may be placed under the control of an externally inducible gene promoter to place expression under the control of the user. An advantage of introduction of a heterologous gene into a plant cell, particularly when the cell is comprised in a plant, is the ability to place expression of the gene under the control of a promoter of choice, in order to be able to influence gene expression, and therefore vernalization response, flowering time, leaf shape, shade avoidance response, and/or other characteristic, according to preference. Furthermore, mutants and derivatives of the wild-type gene, e.g. with higher or lower activity than wild-type, may be used in place of the endogenous gene.

In the present invention, over-expression may be achieved by introduction of the nucleotide sequence in a sense orientation. Thus, the present invention provides a method of influencing a physical characteristic of a plant, the method including causing or allowing expression of the product (polypeptide or nucleic acid transcript) encoded by heterologous nucleic acid according to the invention from that nucleic acid within cells of the plant.

Down-regulation of expression of a target gene may be achieved using anti-sense technology or "sense regulation" ("co-suppression").

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) *Nature* 334, 724-726; Zhang et al, (1992) *The Plant Cell* 4, 1575-1588, English et al., (1996) *The Plant Cell* 8, 179-188. Antisense technology is also reviewed in Bourque, (1995), *Plant Science* 105, 125-149, and Flavell, (1994) *PNAS USA* 91, 3490-3496.

An alternative is to use a copy of all or part of the target gene inserted in sense, that is the same, orientation as the target gene, to achieve reduction in expression of the target gene by co-suppression. See, for example, van der Krol et al., (1990) *The Plant Cell* 2, 291-299; Napoli et al., (1990) *The Plant Cell* 2, 279-289; Zhang et al., (1992) *The Plant Cell* 4, 1575-1588, and U.S. Pat. No. 5,231,020.

The complete sequence corresponding to the coding sequence (in reverse orientation for anti-sense) need not be used. For example fragments of sufficient length may be used. It is a routine matter for the person skilled in the art to screen fragments of various sizes and from various parts of the coding sequence to optimise the level of anti-sense inhibition. It may be advantageous to include the initiating methionine ATG codon, and perhaps one or more nucleotides upstream of the initiating codon. A further possibility is to target a conserved sequence of a gene, e.g. a sequence that is characteristic of one or more genes, such as a regulatory sequence.

The sequence employed may be about 500 nucleotides or less, possibly about 400 nucleotides, about 300 nucleotides, about 200 nucleotides, or about 100 nucleotides. It may be possible to use oligonucleotides of much shorter lengths, 14-23 nucleotides, although longer fragments, and generally even longer than about 500 nucleotides are preferable where possible, such as longer than about 600 nucleotides, than about 700 nucleotides, than about 800 nucleotides, than about 1000 nucleotides or more.

It may be preferable that there is complete sequence identity in the sequence used for down-regulation of expression of a target sequence, and the target sequence, though total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a mutant, derivative, variant or allele, by way of insertion, addition, deletion or substitution of one or more nucleotides, of such a sequence. The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%, 150 or 20% or more mismatch between the sequence used and the target gene.

Generally, the transcribed nucleic acid may represent a fragment of a gene, or the complement thereof, or may be a mutant, derivative, variant or allele thereof, in similar terms as discussed above in relation to alterations being made to a coding sequence and the homology of the altered sequence. The homology may be sufficient for the transcribed anti-sense RNA to hybridise with nucleic acid within cells of the plant, though irrespective of whether hybridisation takes place the desired effect is down-regulation of gene expression.

Thus, the present invention also provides a method of modifying, affecting, altering or modulating a characteristic of a plant, e.g. vernalization response, flowering time, leaf shape and/or shade avoidance response, the method including causing or allowing anti-sense transcription from heterologous nucleic acid according to the invention within cells of the plant.

The present invention further provides the use of the nucleotide sequence of VRN2, or a fragment, mutant, derivative, allele, variant or homologue thereof for down-regulation of gene expression, particularly down-regulation of expression of a VRN2 gene or homologue thereof, preferably in order to influence a physical characteristic of a plant, especially vernalization response, flowering time, leaf shape and/or shade avoidance response.

When additional copies of the target gene are inserted in sense, that is the same, orientation as the target gene, a range of phenotypes is produced which includes individuals where over-expression occurs and some where under-expression of protein from the target gene occurs. When the inserted gene is only part of the endogenous gene the number of under-expressing individuals in the transgenic population increases. The mechanism by which sense regulation occurs, particularly down-regulation, is not well-understood. However, this technique is also well-reported in scientific and patent literature and is used routinely for gene control. See, for example, van der Krol et al., (1990) *The Plant Cell* 2, 291-229; Napoli et al., (1990) The Plant Cell 2, 279-289; Zhang et al, 1992 *The Plant Cell* 4, 1575-1588.

Again, fragments, mutants and so on may be used in similar terms as described above for use in anti-sense regulation.

Thus, the present invention also provides a method of influencing a characteristic of a plant, e.g. vernalization response, flowering time, leaf shape and/or shade avoidance response, the method including causing or allowing expression from nucleic acid according to the invention within cells of the plant. This may be used to suppress activity of a product with ability to influence vernalization response, flowering time, leaf shape and/or shade avoidance response. Here the activity of the product is preferably suppressed as a result of under-expression within the plant cells.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

FIG. 2 illustrates the Red Far-Red Light plant phenotype:
FIG. 2A shows the area of the largest leaf of Ler, fca-1 and vrn2-1 fca-1 plants grown under white light (W) (open bars) or white light with supplementary FR light (W+FR) (shaded bars).
FIG. 2B shows the rosette leaf number at bolting of plants treated as in the experiment of which results are shown in FIG. 2A.

FIG. 6 shows the sequence of VRN2, including coding sequence and predicted amino acid sequence of the encoded protein. Putative NLSs are boxed, the putative acidic activation domain is underlined. The putative zinc-finger motif is doubly underlined. The positions of introns are indicated with arrows. The position of the vrn2-1 mutation is circled. The nucleic acid sequence is SEQ ID NO:1, and the amino acid sequence is SEQ ID NO: 2.

FIG. 7 illustrates dCAPS Marker for the vrn2-1 Mutation. A diagnostic derived CAPS (dCAPS) marker was designated for the vrn2-1 mutation. This utilizes a primer (VRN2-AZ) that includes half of the recognition site for the XmnI restriction enzyme, the other half is supplied, specifically, by the sequence of the vrn2-1 mutation. This results in a successful restriction digestion only when using PCR amplified genomic DNA from vrn2-1 mutants as a template. The SEQ ID NOS: for the sequences shown are as follows: fca-1=SEQ ID NO: 52; vrn2-1 =SEQ ID NO: 53; Xmn1 site=SEQ ID NO: 50; VRN2-AZ=SEQ ID NO: 77; VRN2-AY=SEQ ID NO: 76.

FIG. 8 shows alignment of the Arabidopsis VRN2 amino acid sequence with similar proteins.
FIG. 8A aligns the full-length VRN2 protein, SEQ ID NO: 2, with four other proteins shown by their SEQ ID NOS: as follows: AI163743 Prot=SEQ ID NO: 12; Rice C72616=SEQ ID NO: 10; At Hyp 2245035=SEQ ID NO: 14; KIA00160=SEQ ID NO: 54, using Clustal method with PAM250 residue weight table, performed on 17 Jan. 1999 at 19:19 GMT.
FIG. 8B aligns the zinc finger region, using Clustal method with PAM250 residue weight table, performed on 17 Jan. 1999 at 19:25 GMT. The alignment of SEQ ID NOS: 17-38 is shown.

ABBREVIATIONS

Figure 1:
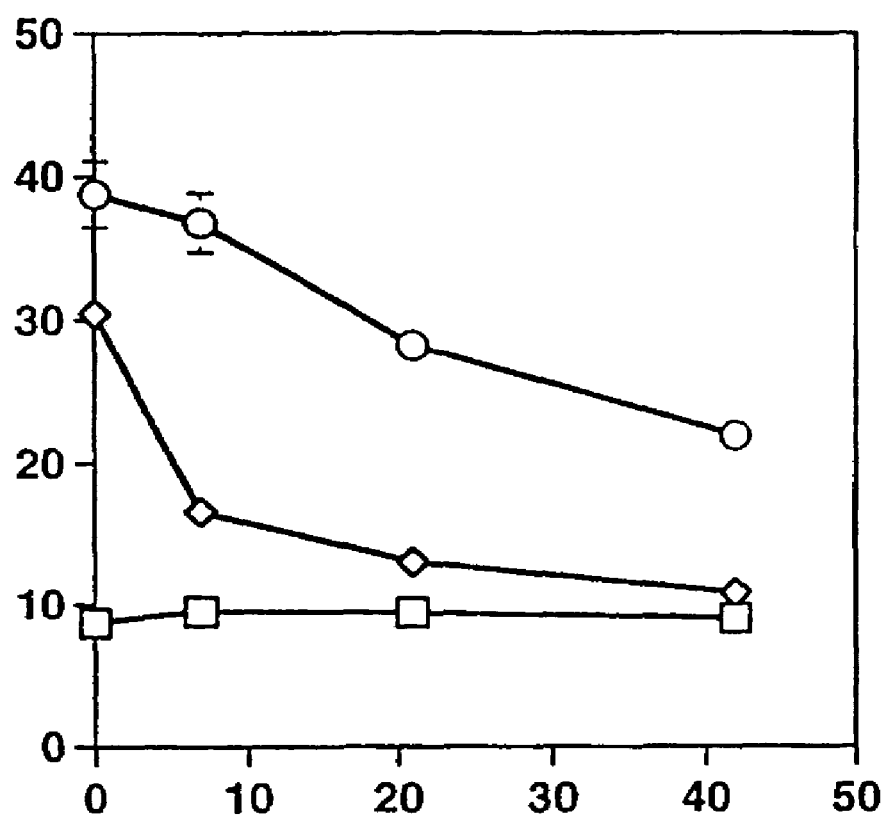
FIG. 1 shows total leaf number (Rosette plus Cauline) of Ler plants (squares), fca-1 plants (diamonds) and vrn2-1 fca-1 plants (circles) after various periods of vernalization (measured in days).

At *Arabidopsis thaliana*, Sc *Saccharomyces cerevisiae*, Sp *Schizosaccharomyces pombe*, Ce *Caenorhabditis elegans*, Dm *Drosophila melanogaster*, Hs *Homo sapiens*, Mm *Mus musculus*, Rn *Rattus norvegicus*, Xm *Xiphophorus maculatus*.

List of Sequences

SEQ ID NO:\\Sequence
1 *Landsberg erecta* VRN2 cDNA
2 *Landsberg erecta* VRN2 amino acid
3 *Landsberg erecta* VRN2 genomic
4 *Columbia* VRN2 cDNA
5 *Columbia* VRN2 amino acid
6 *Columbia* VRN2 genomic
7 5K (*Columbia*, abberant splice) cDNA
8 5K (*Columbia*, abberant splice) amino acid
9 C72616 EST (modified) cDNA
10 C72616 EST (modified) amino acid
11 AI163743 EST (modified) cDNA
12 AI163743 EST (modified) amino acid
13 At Hyp 2245035 (ATFCA7_4)(modified) cDNA
14 At Hyp 2245035 (ATFCA7_4) (modified) amino acid
15 KIAA0160 cDNA
16 KIAA0160 amino acid Additional Sequences Included in the FIGS:
17 *Landsberg erecta* VRN2 zinc finger amino acid
18 At Di19 S51478 zinc finger 1 amino acid
19 At Di19 S54178 zinc finger 2 amino acid
20 At SUP U38946 zinc finger amino acid
21 At Hyp 2191171 zinc finger amino acid
22 At Hyp 3377806 zinc finger amino acid
23 Sc Pep7 91500 zinc finger amino acid
24 Sc TFIIIA 730931 zinc finger amino acid
25 Sp Hyp 1351713 zinc finger amino acid
26 Ce Hyp 255942 zinc finger amino acid
27 Ce Hyp 2854197 zinc finger amino acid
28 Ce Hyp 304459 zinc finger amino acid
29 Dm BRCORE-NS-Z3 zinc finger amino acid
30 Dm GAGA 729556 zinc finger amino acid
31 Dm ken 3550814 zinc finger amino acid
32 Hs ATBF-1976347 zinc finger amino acid
33 Hs KIAA0160 zinc finger amino acid
34 Hs ZNF142 3123312 zinc finger amino acid
35 Mm FOG 2252814 zinc finger amino acid
36 Mm Spalt 1296845 zinc finger amino acid
37 Rn Roaz 2149792 zinc finger amino acid
38 Xm ZF1532083 zinc finger amino acid

EXAMPLE 1

Characterisation and Cloning of VRN of *Arabidopsis Thaliana* and Mutant Alleles Thereof Isolation of vrn2 Mutants Two vrn2 mutant alleles (vrn2-1 and vrn2-2) were isolated by mutagenising fca-1 seeds with EMS as described by Chandler et al. (Plant J (1996) 10: 637-644). WO96/38560 (PCT/GB96/01332) discloses the sequence of fca and mutant alleles and their cloning and characterisation. The vrn2-1 fca-1 line used here has been backcrossed to fca-1 four times. For mapping purposes, the vrn2-1 allele was used (at the 2nd backcross)

Phenotypic Characterization

Vernalization

The vernalization response of vrn2 mutant plants was investigated by examining their flowering time in response to increasing durations of vernalization treatment.

Standard vernalization conditions were used, i.e. low light intensity 5 µmol m$^{-2}$ s$^{-1}$, 8 hr photoperiod, 5±1 degree C., for varying periods (from between 1 and 42 days). Similar effects would be observed under continuous or no light, the temperature is more important.

In the absence of a vernalization treatment, vrn2-1 fca-1 mutant plants showed a small but consistent delay in flowering compared to the parental (wild-type) fca-1 controls (FIG. 1: vrn2-1 has a higher leaf number than fca-1, a reduced leaf number correlating with a transition from vegetative to reproductive (i.e. flowering) state). However, following vernalization, this difference was greatly magnified (FIG. 1). The response exhibited by vrn2-1 fca-1 plants was typically a 35% reduction in total leaf number after 6 weeks of vernalization, compared to 67% reduction or fca-1 controls. The delay in flowering, both with and without a vernalization treatment, as measured by increased leaf number, was also observed if the days to flower i.e. the day at which the first floral bud was visible was used.

Red/Far-Red Light Perception

The response to vernalization in *Arabidopsis* has been positively correlated with the response to different ratios of Red(R) to Far-red(FR) light; mutants and ecotypes that respond strongly tend to respond strongly to conditions of low R:FR (Bagnall, Ann Bot (1993) 71: 75-83; Martinez-Zapater et al., Plant Physiol (1990) 92: 770-776). This response typically manifests itself in two distinct ways—an acceleration of flowering time (leading to an effect that mimics the effect of a vernalization treatment) and a reduction in leaf area (or shade avoidance). This response is believed to have evolved to allow plants to adapt to the availability of light allowing individuals to seek light when in competition with their neighbors.

We examined the ability of vrn2-1 fca-1 mutants to respond to conditions that mimic such an environment.

Under these conditions, vrn2-1 fca-1 plants showed a marked reduction in the shade avoidance response, with the mean area of the largest leaf decreasing by only 26%, compared to 74% for the fca-1 control (FIG. 2A). However, the vrn2-1 mutation does not appear to affect all aspects of the response to FR light, as vrn2-1 fca-1 plants showed a similar acceleration of flowering in response to supplementary FR light as fca-1 controls (FIG. 2B)

These data provide indication that VRN2 plays a role in regulating the response to FR light, and may mediate changes specifically in leaf size (as flowering time is only slightly affected) under conditions of low R:FR ratios.

Genetic Mapping

Figure 3:
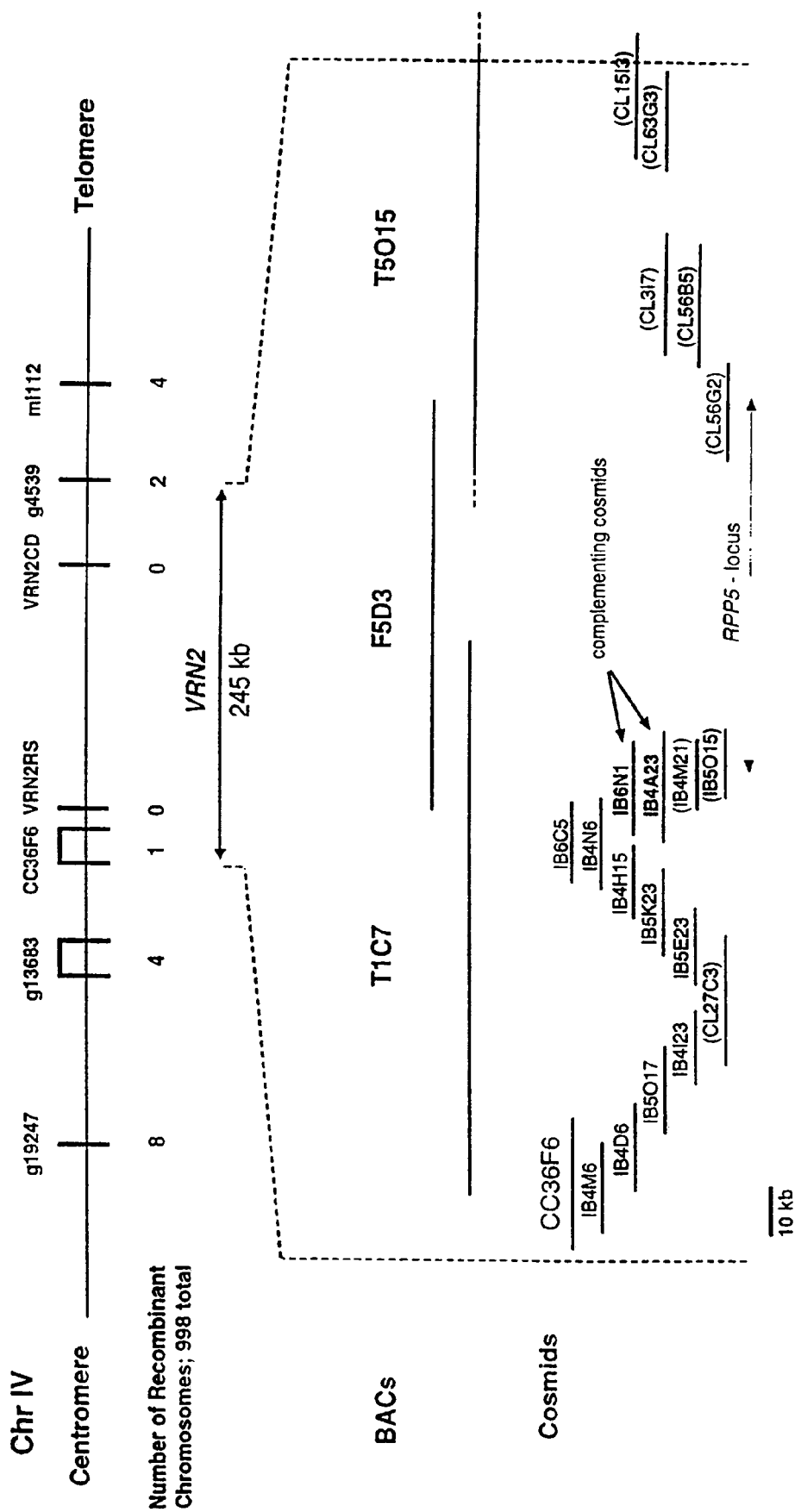
FIG. 3 illustrates results of genetic and physical mapping of VRN2 in Arabidopsis thaliana.

The VRN2 gene was mapped in an F2 population derived from the cross vrn2-1 fca-1 crossed to fca-10, following the procedure used to map the VRN1 gene (Chandler et al. supra.). The VRN2 gene was initially positioned using a population of 70 F2 individuals between the RFLP markers g13683 and mi112 (Schmidt et al., Plant J (1996) 9: 755-765) on the long arm of Chromosome IV (or D), using conventional techniques. The map position of VRN2 was further refined by screening an additional 429 F2 plants with a SSLP derived from the marker g19247 (Schmidt et al., (1996) Plant J 9: 755-765) and the CAPS-marker g4539 (Parker et al., Plant Cell (1998) 9: 1-17). A total of 12 individual F2 plants that were recombinant between g19247 and g4539 were further analyzed with RFLP markers g13683 and CC36F6 (Bancroft et al., Weeds World 4ii: (1997)) and the CAPS marker C18 (Parket et al., supra.), and with two additional CAPS markers (VRN2RS, VRN2CD) generated using the published Columbia sequence (Bevan et al., Nature (1998) 391: 485-488) (accession numbers Z97341 and Z97342) as a template. The VRN2 gene was localized to a 245 kb region defined at the centromeric (north) end by an RFLP detected with the cosmid CC36F6, and at the telomeric (south) end by the g4539 CAPS marker. This interval is defined by 3 recombinant individual F2 plants; 1 recombinant between VRN2 and CC36F6, and 2 recombinants between g4539 and VRN2 (FIG. 3).

Physical Mapping

The genetic interval defined by CC36F6 and g4539 is almost completely covered by the 3 BAC clones T1C7, I5D3 and T5O15. Cosmids derived from subclones of YAC EW16B10 in the binary vector 04541 (Bancroft et al., supra.) (abbreviated as IB) were positioned by end sequencing, and ordered relative to the published sequence of the Columbia ecotype in this region (Genbank accession numbers Z97341 and Z97342). We selected cosmids clones that extended from the complex RPP5 locus outwards to CC36F6 and g4539, reasoning that VRN2 was not within the RPPS locus, which is comprised of multiple repeats of RPP5-like genes in both Columbia and Landsberg ecotypes (Bevan et al., supra.).

Additional Landsberg cosmids in the 04541 binary vector covering the region not covered by the *Columbia* YAC subclone cosmids were identified by hybridization to the inserts from BACs TlC7 and T5O15, and aligned based on end sequencing, and compared to the published *Columbia* sequence (Bevan et al., supra.) and to the sequence of the *Landsberg* ecotype in this region. An almost complete cosmid contig was generated over this region.

Simultaneously with the isolation of cosmids, ordered cosmids, beginning with those at the centromeric end of the contig, were transformed into vrn2-1 fca-1 plants by *Agrobacterium tumefaciens*-mediated vacuum infiltration (Bechtold et al., C R Acad Sci Paris (1993) 316: 1194-1199). (FIG. 3). The presence of the cosmid in each transgenic line (T1 plants) was confirmed by a cosmid-specific diagnostic PCR, comprising an insert specific primer (corresponding to a portion of the *Columbia* genomic DNA) and a primer present in the cosmid vector.

Cosmid Complementation

Cosmids introduced into vrn2-1 fca-1 plants were tested for their ability to complement the vrn2 phenotype. T2 seeds, from individual T1 plants segregating kanamycin resistance at a 3:1 ratio, were sown on soil and vernalized for two (in some experiments three) weeks. Plants were then transferred to greenhouse conditions, and after ten days pricked out into individual compartments of divided trays. Total leaf number was determined, and cosmids were scored as complementing if the segregation ratio of early to late plants (when compared to fca-1 and vrn2-1 fca-1 controls) plants was approximately 3:1.

Two Columbia cosmids (4A23, 2 out of 2 T1s; 6N1, 1 out of 1 T1) clearly complemented the phenotype of vrn2-1 fca-1 mutants, with the earliest plants flowering at approximately the same time as vernalized fca-1 plants.

Sequence Analysis and ORF Prediction

Figure 4:
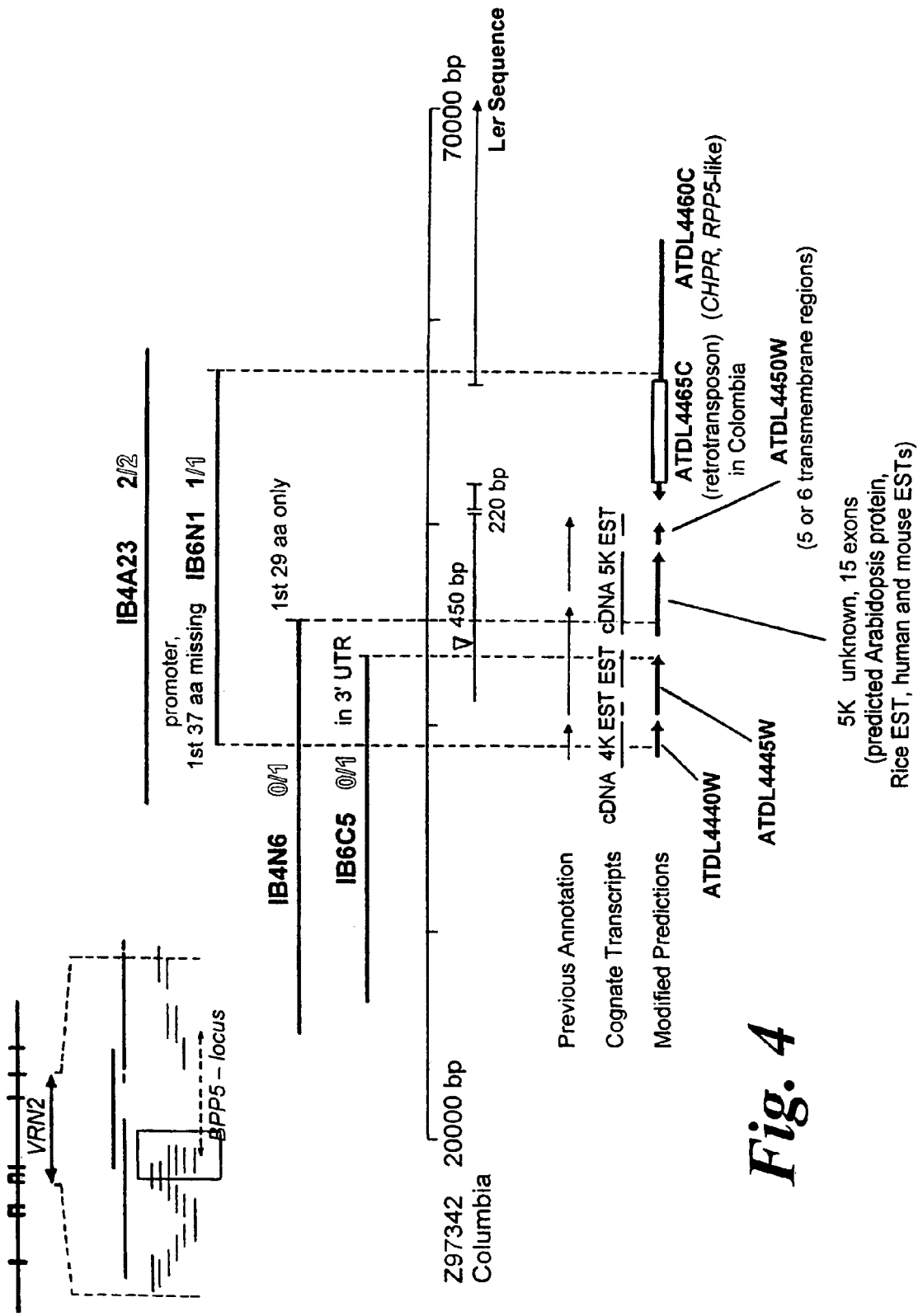
FIG. 4 illustrates cosmids and genes near VRN2 in the *Arabidopsis* genome.

The sequence in common to both IB4A23 and IB6N1 cosmids has previously been annotated as containing 2 complete predicted genes (ATDL4445W and ATDL4450W) and (presumably non-functional) portions of two other genes—the 3' end of ATDL4440W and the 3' end of the RPP5-like gene, CHPR (ATDL4460W) (Bevan et al., supra.) Genbank accession number Z97342. In addition, a cognate cDNA (5K) not included in the annotation is present in this region, and appears to span two of the predicted genes (ATDL4445W and ATDL4450W) (Bevan et al., supra.). However, as two cosmids in the region (1 independent T1 line from each of cosmids IB4N6 and IB6C5) did not complement the mutant phenotype (FIG. 4) this ruled out the predicted gene ATDL4445W. This left the unannotated cDNA 5K, and the predicted gene ATDL4450W as candidates for VRN2. However, the presence the cognate cDNA 5K from the *Columbia* ecotype that overlapped both ATDL4445W and ATDL4450W necessitated a re-examination of the prediction for the ATDL4450W gene.

In order to define the structure of these genes, we used the NetGene2 prediction program (Hebsgaard et al., Nucl Acids Res (1998) 24: 3439-3452), using "*Arabidopsis*" as the organism option (the only parameter that can be set manually). BLAST, PSI-BLAST, PSORT and PROSITE programs were used to identify potential function domains and similarities (Altschul et al., Nucleic Acids Res (1997) 25: 3389-3402; Bairoch et al., Nucl Acids Res (1997) 25: 217-221; Nakai et al., Genomics (1992) 14: 897-911). Default parameters of TBLASTN, PSI-BLAST and BLASTP were used (Expect=10, BLOSUM62 matrix, gap penalty=11, penalty per gap 1, lambda ratio 0.85). The NCBI/GenBank database was used. The PSORT algorithm (Nakai) was used, using the "plant" option as the source organism (the only parameter that can be manually changed). The Profile Scan program at PROSITE (Bairoch) was used to search for motifs in VRN2, with default parameters (there are no parameters a user can select, the results being "hit" or "no hit").

This analysis yielded predictions for two genes, 5K, a putative nuclear localized protein that is highly post-transcriptionally spliced (15 exons), represented by the Columbia cognate cDNA; and a modified prediction for 4450, with 6 putative membrane-spanning domains, represented at its 3' end by an *Arabidopsis* EST (accession number T22412).

Determination of the vrn2-1 Mutation and Identification of the VRN2 Gene

In an attempt to determine which gene (5K or 4450) is VRN2, PCR primers were designed to amplify products encompassing the entire predicted open reading frame of both genes.

Three independent RT-PCR reactions using total RNA prepared from fca-1,vrn2-1 fca-1 and vrn2-2 fca-114 day-old seedlings grown on GM plates in continuous light were performed for each predicted gene with a high fidelity enzyme mix (Boehringer Mannheim, HiFi System). These PCR products were sequenced using both the primers used for PCR, and a series of internal primers, using the BIGDYE kit (PE Applied Biosystems). The reactions were run on an ABI377 machine, and compiled using the SeqMan (DNAStar, Lasergene) program.

The sequences of the PCR confirmed our prediction for both genes, and indicated that we had amplified across the entire open reading frame of 5K and ATDL4450W as anticipated.

Figure 5:
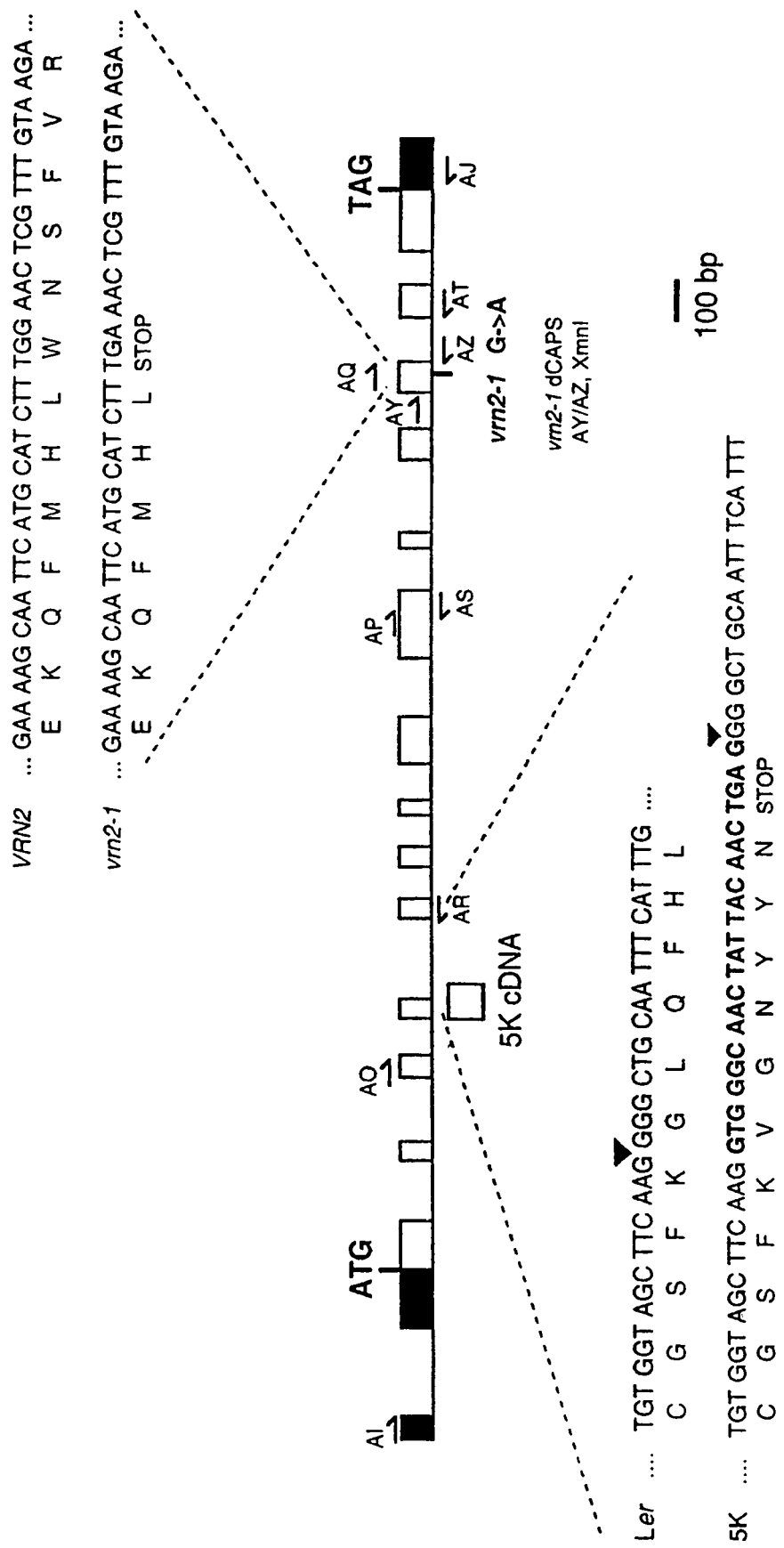
FIG. 5 illustrates the structure of the VRN2 gene of *Arabidopsis*, the 5K cDNA aberrant splicing, and the position and nature of the vrn2-1 mutation. Exons are shown as open boxes. Untranslated regions are shown as shaded boxes. Introns are shown as lines. SEQ ID NOS: for the sequences shown are as follows: VRN2 nucleic acid=SEQ ID NO: 39; VRN2 amino acid=SEQ ID NO: 40; vrn2-1 nucleic acid=SEQ ID NO: 41; vrn2 amino acid=SEQ ID NO: 42; LER nucleic acid sequence=SEQ ID NO: 43; LER amino acid sequence=SEQ ID NO: 44; 5K nucleic acid sequence=SEQ ID NO: 45; 5K amino acid sequence=SEQ ID NO: 46.

Several minor polymorphic differences were detected between the published *Columbia* sequence, and the *Landsberg erecta* sequence we amplified by PCR. These differences were consistent with the *Landsberg erecta* genomic sequence in this region. Furthermore, the *Columbia* cDNA for 5K appears to utilise a different splice donor site from that used in the *Landsberg* ecotype, and would produce a truncated, presumably non-functional protein (FIG. 5). However, we have also sequenced the *Columbia* 5K product derived independently by RT-PCR, and this appears to use the same splice site as *Landsberg*, and should encode a functional protein. A consistent difference between the vrn2 mutants and fca-1 was detected in the 5K PCR product, a G to A change at position 1201 of the predicted cDNA in vrn2-1 fca-1 (FIG. 5). We are currently investigating the nature of the mutation in the vrn2-2 allele. This type of mutation, a single base-pair change, is commonly observed following EMS mutagenesis. This mutation converts a TGG codon (Tryptophan) to stop codon (TGA), and would result in the production of a truncated protein of 322 amino acids in the vrn2-1 mutant, compared to 443 amino acids of wild type VRN2 (FIG. 6). The presence of this mutation indicated that 5K was likely to be VRN2. The presence of the vrn2-1 mutation in the genome of vrn2-1 fca-1 mutant plants was confirmed by a derived CAPS (dCAPS) (Michaels et al., Plant J (1998) 14: 381-385; Neff et al., Plant J (1998) 14: 387-392) marker specific for the vrn2-1 mutation (FIG. 7). This diagnostic test is specific for the vrn2-1 mutation, as it detects wild type VRN2 in both fca-1 and vrn2-2 fca-1 mutants.

Analysis of the VRN2 Gene

To gain an insight into the possible function of the VRN2 gene, and how the vrn2-1 mutation may affect the function of the VRN2 protein, we compared the amino acid sequence of VRN2 to several databases of protein and translated nucleic acid sequences using BLASTP and TBLASTN programs at NCBI, using the default parameters as noted above.

Several molecules with a significant degree of similarity were identified (Table 1 and Table 2).

Figure 8A:
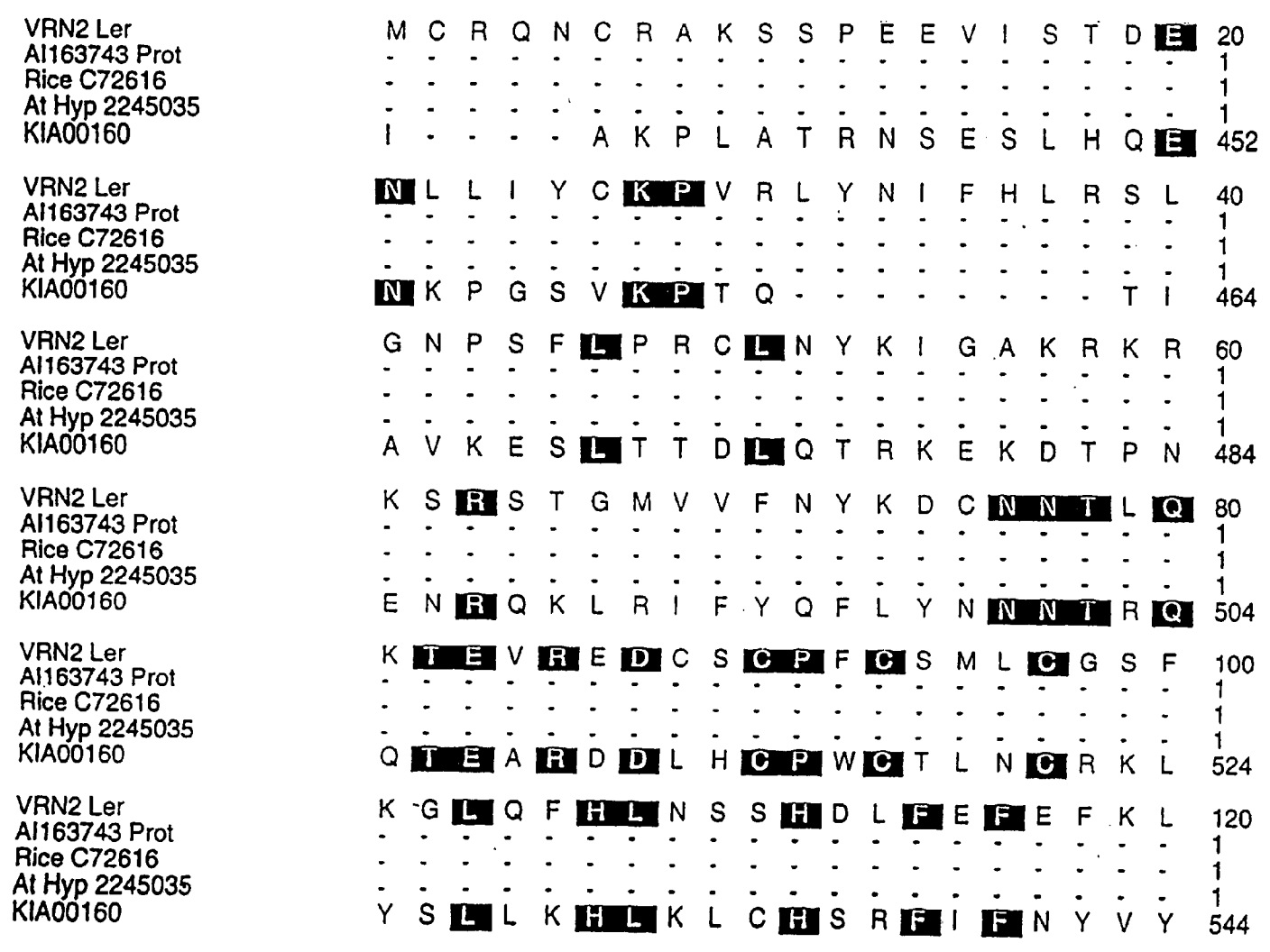

One such gene, represented by a human cDNA (KIAA0160) shares homology with VRN2 over a short region near the amino terminus of VRN2 (amino acids 63 to 132), and a longer, but less conserved region of homology towards the carboxy terminus (amino acids 263-366) (FIG. 8a). Closer examination of the amino terminal conserved region revealed that it matches the consensus of a zinc-finger motif. Such motifs can take a variety of forms, but all co-ordinate zinc atoms through two cysteine residues, and two cysteine or histidine residues. VRN2 falls into the latter class, having a C2H2 motif comprised of two cysteines separated by 2 amino acids, and two histidines separated by two amino acids (Mackay et al., TIBS (1998) 23: 1-4).

Figure 8B:
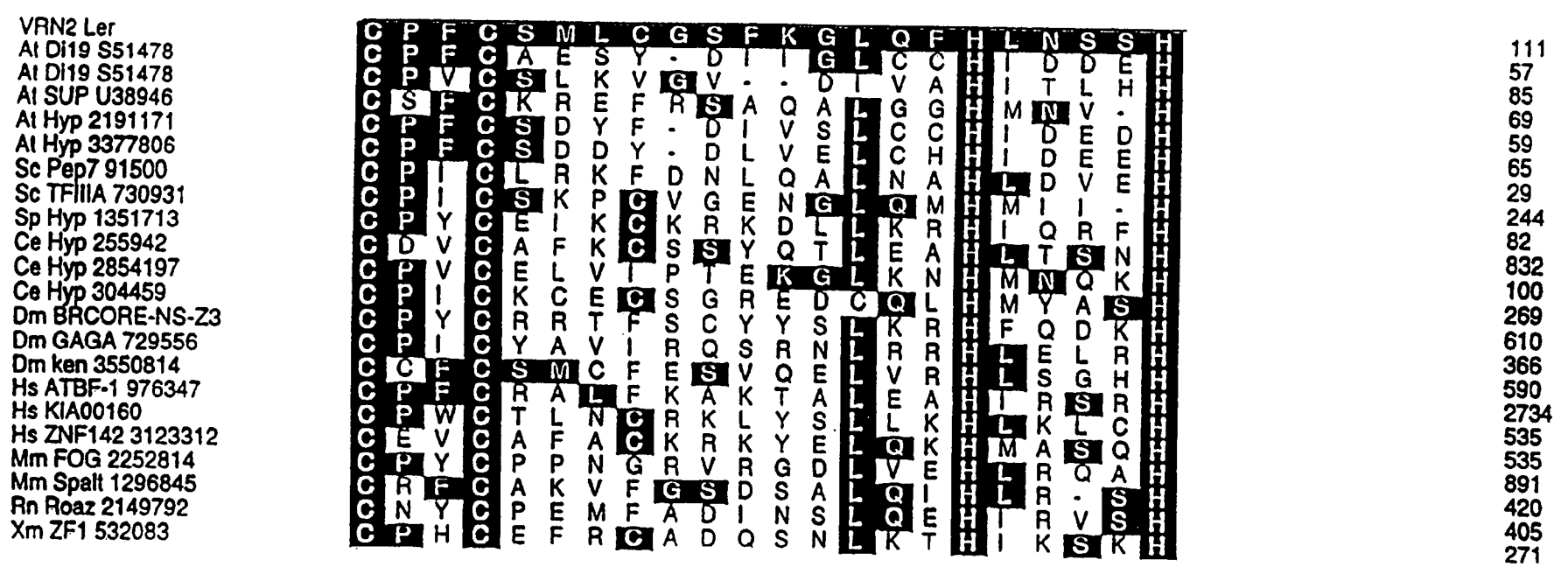

Zinc-finger motifs are known to be capable of mediating both protein-DNA and protein-protein interactions. The zinc finger motif of VRN2 does not closely resemble the large EPF family of *Arabidopsis* C2H2 zinc fingers from *Arabidopsis*, which have a highly conserved QALGG motif in the middle of the zinc finger (Kubo et al., Nucl Acids Res (1998) 26: 608-615) (FIG. 8b). In addition, VRN2 differs from the EPF proteins in that VRN2 has a single zinc finger motif, whereas most members of the EPF family (with the exception of SUP and AtZFP1) have between two and four zinc fingers (Kubo et al., supra.). This amino-terminal region (amino acids 63-132), and particularly the zinc-finger motif (amino acids 90-111) may thus represent a domain that mediates protein-protein or protein-DNA interactions.

The carboxy terminus of VRN2 (amino acids 263 to 366) is similar to several other candidate genes (Table 1 and Table 2). As mentioned above, there is limited homology to the human predicted protein KIAA0160. The molecule showing greatest homology to VRN2 is an EST sequence from poplar (*Populus tremula* L. x *Populus tremuloides* Michx (Accession Number AI163743) (Sterky et al., PNAS USA (1998) 95: 13330-13335) which has 52.8% identity over 127 amino acids (Table 1), as calculated with the BLASTP algorithm using default parameters (as noted above). VRN2 also shows significant similarity to a predicted *Arabidopsis* protein (ATFCA7_4, Accession Number 2245035) (Bevan et al., supra.), which is quite close to VRN2 on chromosome 4, only 30 kb away towards the centromere. A close examination of the sequence near this gene revealed that the prediction as annotated may be incorrect, as the use of a different splice site, resulting a different carboxy terminus to the protein, increases the degree of homology with VRN2. The similarity of these two *Arabidopsis* genes raises the possibility that VRN2 may be a member of a gene family in *Arabidopsis*, and their close position suggests that these genes may have arisen following a duplication. Arguing against this notion is the observation that these two genes, VRN2 and ATFCA7_4, are transcribed in opposite directions. A rice EST (C72616) also shares significant similarity with the carboxyl region of VRN2, suggesting that this region may form an evolutionarily conserved domain present in monocots and dicots.

This conserved carboxy region is predicted to be highly charged, as it is composed of a large number of acidic residues (D and E). This highly charged region is highly similar in the Poplar and rice ESTs (Table 2). Such acidic regions are found in a number of eukaryotic transcription factors, and often function as activation domains (Hahn, Cell (1993) 72: 481-483). It is therefore possible that VRN2 may function as a transcription factor, given it has both a DNA-binding motif (or protein binding) (amino acids 63-132) and a putative activation domain (amino acids 263-328). Furthermore, the amino portion of VRN2 contains two predicted nuclear localization signals (NLSs)(FIG. 6). The first is a simple 4 residue basic signal, while the second is a bi-partite signal, that fits the consensus (R/K) (R/K)N10(R/K)4 (Dingwall et al., TIBS (1991) 16: 478-481).

EXAMPLE 2

Production and Characterisation of *Arabidopsis* Transgenic for VRN2

VRN2 cDNA in the sense orientation is cloned into plant expression vectors SLJ4D4 and SLJ4K1 (Jones et al., (1992) Transg. Res. 1, pp 285-297) according to the teaching of Sambrook J et al (1989) Molecular Cloning: A Laboratory Manual, Cold Spring Harbor Laboratory Press, Cold Spring Harbor, N.Y. SLJ4D4 and SLJ4K1 place the VRN2 cDNA under the control of the Ca MV 35S promoter and include terminator sequences from octopine synthase (ocs) and nopaline synthase (nos) genes, respectively.

Antisense constructs are produced in the same manner except that the VRN2 cDNA is inserted into the expression vectors in the opposite orientation.

The VRN2 expression cassettes are then subcloned separately into the binary vector SLJ1714 (Jones et al., supra), and mobilised into *Agrobacterium* strains by tri-parental mating according to the teaching of Hoekema et al., (1983) Nature 303, pp 179-180. *Arabidopsis* are transformed with the *Agrobacterium* strains carrying VRN2 expression constructs (either sense or antisense) following the teaching of Bechtold et al., (1993) C R Acad. Sci. Paris 316, pp 1194-1199.

*Arabidopsis* plants are assayed for changes in their response to changes in the ratio of far red light, essentially as described by Halliday et al., (1997) Plant J. 12, pp 1079-1090.

Results

Differences in vernalisation requirement and response are observed in *Arabidopsis* plants transgenic for VRN2 (sense or antisense orientation) relative to *Arabidopsis* plants transformed with empty vectors and non-transformed *Arabidopsis* plants.

EXAMPLE 3

Production and Characterisation of Tobacco Transgenic for VRN2

VRN2 cDNA in the sense orientation is cloned into plant expression vectors SLJ4D4 and SLJ4K1 as described in Example 2.

Antisense constructs are produced in the same manner except that the VRN2 cDNA is inserted into the expression vectors in the opposite orientation.

VRN2 expression cassettes subcloned separately into the binary vector SLJ1714 (Jones et al supra), are mobilised into *Agrobacterium* strains by tri-parental mating as in Example 2, and tobacco plants are transformed using the *Agrobacterium* strains carrying VRN2 expression constructs (either sense or antisense) following the teaching of Horsch et al., (1985) Science 227, pp 1229-1231.

Tobacco plants are assayed for changes in their response to 5 changes in the ratio of far red light, essentially as described by Halliday et al., (1997) Plant J. 12, pp 1079-1090.

Results

Differences in vernalisation requirement and response are observed in Tobacco plants transgenic for VRN2 (sense or antisense orientation) relative to Tobacco plants transformed with empty vectors and non-transformed Tobacco plants.

EXAMPLE 4

Production and Characterisation of Brassica (Oil Seed Rape, Winter Type) Transgenic for VRN2

Sense and antisense constructs are used to generate *Agrobacterium* strains carrying VRN2 expression constructs (either sense or antisense) as described in Example 2 and Example 3, and are used to transform oil seed rape following the teaching of Moloney et al., (1989) Plant Cell Rep. 8, pp 25 238-242.

Results

Differences in vernalisation requirement and response are observed in oil seed rape plants transgenic for VRN2 (sense or antisense orientation) relative to oil seed rape plants transformed with empty vectors and non-transformed oil seed rape plants.

EXAMPLE 5

Production and Characterisation of Rice Transgenic for VRN2

VRN2 cDNA in the sense or antisense orientation is cloned into constructs and used to generate respective *Agrobacterium* strains. The *Agrobacterium* strains carrying VRN2 expression constructs (either sense or antisense) are used to transform rice following the teaching of Kohll A et al (1998) Proc. Natl. Acad. Sci. USA 95, pp 7203-7208.

Results

Differences in vernalisation requirement and response are observed in rice plants transgenic for VRN2 (sense or antisense orientation) relative to rice plants transformed with empty vectors and non-transformed rice plants.

EXAMPLE 6

Production and Characterisation of Wheat Transgenic for VRN2

*Agrobacterium* strains carrying VRN2 expression constructs (either sense or antisense) are generated as in preceding Examples and are used to transform wheat following the teaching of Becker D et al.,(1994) Plant J. 5, pp 299-307.

Results

Differences in vernalisation requirement and response are observed in wheat plants transgenic for VRN2 (sense or antisense orientation) relative to wheat plants transformed with empty vectors and non-transformed wheat plants.

Methods and Materials

Plant Growth

For vernalization treatments, seeds were sown on a damp layer of fine grit (Levington's M3) on wet soil in individual pots, and vernalized for increasing durations at 4° C., 8 hr light:16 hr dark, 5 µmol m$^{-2}$ sec$^{-1}$ light intensity. Seed sowing was staggered, with all plants removed from the vernalization conditions simultaneously. Following vernalization, plants were placed into a controlled environment chamber (Gallenkamp), 20° C., 16 hr light: 8 hr dark 90 µmol m$^{-2}$ sec$^{-1}$ light intensity. Plants receiving no vernalization treatment were stratified for 2 days under vernalization conditions, and grown for two days prior to transfer into the growth cabinet. Plants were grown for 10 days, and then pricked out into individual compartments of P40 trays. The flowering time, as measured by counting total leaf number (i.e. rosette and cauline leaves) was determined once the primary inflorescence had elongated sufficiently.

The phenotype of vrn2-1 fca-1 plants was examined under different ratios of red to far-red (R:FR) light. Plants were stratified for 2 days, then grown for 10 days under continuous light, and then transferred to separate growth chambers with white light (W), R:FR ratio of 5.8, with or without supplementary FR light (W+FR), R:FR ratio 0.08. The number of rosette leaves was determined to measure flowering time, and the area of the largest leaf was used as an indicator of the shade-avoidance response.

Mapping

VRN2 was positioned on the long arm of Chromosome 4 (or D) through linkage to the RFLP marker m506 (Chang et al., Proc Natl Acad Sci USA (1988) 85: 6856-6860), in progeny of a cross between vrn2-1 fca-1 (Ler background) and fca-10 (Ws background). Further RFLP markers in this region (Liu et al., Plant J (1996) 10:733-736) were used to refine the position of VRN2. We used standard RFLP techniques, using 32P-labeled cosmid probes, and a PhosphorImager detection system. A Ler:Ws RFLP was detected when using EcoRI digested genomic DNA, and either g13683 or CC36F6 as probes. The g19247 marker is a SSLP marker (using the primers g19247F and g19247R, see. below), with Ler producing a PCR-amplified band of approximately 750 bp, while Ws produces a band of 862 bp. Fine mapping of VRN2 was performed using a series of PCR-derived markers, based on the *Columbia* genomic sequence in this region (Bevan et al., supra.). The VRN2CD marker was amplified with two primers, VRN2-C and VRN2-D, and digested with DdeI. This produces a CAPS marker, with Ler producing bands of (approximately) 480 bp, 290 bp and 190 bp, while Ws produces bands of (approximately) 330 bp, 290 bp and 150 bp. The VRN2RS marker is a dominant marker for Ws (i.e. Ler:Ws heterozygotes cannot be distinguished from Ws), produced by amplifying genomic DNA with VRN2-R and VRN2-S (see below), and digesting the product with MboII. This produces a single predominant band (and several much smaller unresolved bands) in Ler of approximately 400 bp, while Ws produces two bands, 400 bp and 300 bp.

Cosmid Isolation

Cosmids covering the region not covered by the subclones of EW16B10 YAC were identified through hybridization to BAC inserts derived from BACs T5015 and T1C7. BAC DNA was purified and the insert isolated following digestion with NotI and separation by pulsed field gel electrophoresis (PFGE) as described in (Bancroft et al., supra.). Purified BAC inserts were labeled with a32P-dCTP by random primed labeling, and hybridized to arrayed grids of a Ler genomic cosmid library. Positively hybridizing cosmids were identified, and rescreened following restriction enzyme digestion, southern blotting and hybridized to the BAC insert probe used initially. Cosmids in the region of interest were selected, and genomic sequence was obtained from the ends of the insert using the BIGDYE cycle sequencing kit, and T3 and T7 primers, whose sequences flank the genomic DNA insert site. This sequence was aligned with that of the Columbia genomic sequence to accurately position the cosmids.

Complementation

Cosmids in the 04541 binary vector were mobilized into *Agrobacterium tumefaciens* (strain C58C1 RifR by tri-parental mating (Hoekema et al., Nature (1983) 303: 179-180). vrn2-1 fca-1 plants were transformed with these *Agrobacterium* strains by vacuum infiltration (Bechtold et al, supra.). Transgenic T1 plants were selected on GM with Kanamycin (50 mg/mL), and transferred to soil when they had reached the 3-4 leaf stage. The presence of each cosmid in the transgenic lines was confirmed using either a Ler/Col specific polymorphism (CAPS or SSLP marker) or more commonly, through the use of a specific diagnostic PCR reaction, using a primer present within the cosmid insert sequence and a primer present in the cosmid flanking the insert site. Transgenic plants were also tested for the presence of the fca-1 mutation, as the T0 plants should carry this mutation. Together, these two methods ensured that only vrn2-1 fca-1 plants carrying the desired cosmids were analyzed further. We aimed to produced 5 to 6 independent T1 transformants for each cosmid, but for some cosmids only a single line was produced. However, as complementation was observed before we had generated T1s for all of the cosmids, we are continuing to produce additional transgenic T1 plants carrying the cosmids near VRN2. T1 plants were grown in a controlled environment chamber (conditions as above), and allowed to self. T2 seed were collected, and analyzed for the segregation of Kanamycin resistance or sensitivity on GM plates containing Kanamycin (as above), scored 14-20 days after germination. Progeny from T1 plants that segregated a 3:1 ratio of resistant to sensitive plants were tested for their ability to complement the vrn2-1 mutant phenotype, by vernalizing for 3 weeks and recording the total leaf number.

Sequencing ORFs

Two potential open reading frames were sequenced following RT-PCR using RNA isolated from fca-1 and vrn2-1 fca-1 plants. cDNAs were reverse transcribed, primed by a dT12-18 primer, and specific primers were then used to PCR amplify regions corresponding to the ORFs for ATDL4450W and 5K (VRN2). The Boehringer Mannheim HiFi PCR system was used to increase the fidelity of amplification. The primers VRN2-AL and VRN2-AM were used to prime ATDL4450W, and VRN2-AI and VRN2-AJ for 5K. For 5K, the PCR reaction for the full length product (VRN2AI-VRN2AJ) was inefficient, so subsequent reactions were performed to amplify the cDNA in two overlapping fragment, using the primer combinations VRN2-AI with VRN2-AS; and VRN2-AO with VRN2-AJ. The PCR products were isolated and purified, and sequenced directly using the BIGDYE sequencing kit (PE Applied Biosystems). At least two independent PCR products were sequenced from each allele. We sequenced the ATDL4450W PCR products with the amplifying primers VRN2-AL VRN2-AM, and VRN2-AU through VRN2-AX. The 5K cDNA was sequenced with VRN2-AI, VRN2-AJ and VRN2-AO through VRN2-AT. Sequences were aligned into contigs using the DNAStar software package (LaserGene).

Sequence Comparisons

EST and cDNA sequences were first translated using the MapDraw program of DNAStar (LaserGene). This revealed several regions where the sequence appeared to be incorrect, as small changes to the described sequences drastically improved the similarity to VRN2. Modified nucleic and amino acid sequences were initially aligned using programs within the MegAlign Package of DNAStar (LaserGene), as follows:

Amino acid sequences were initially aligned using the Clustal V method (Higgins and Sharp (1989) CABIOS vol. 5, no.2, 151-153). Default parameters were used: Gap penalty 10, Gap length penalty 10, ktuple 2, and the PAM 250 residue weight table. Alignment was refined by eye and hand, making minor adjustments to position of gaps to improve alignment.

Nucleic acid (EST and cDNA) sequences were initially aligned with the Hein method (Hein (1990) Methods in Enzymology, vol. 183, 626-645), using default parameters: Gap penalty 11, Gap length penalty 3, ktuple 2, and the weighted residue weight table. Where the nucleotide alignment (when translated) did not correspond to the amino acid alignment, the positions of gaps were adjusted to correspond with the gaps in the amino acid alignments.

dCAPS Marker for the vrn2-1 Mutation

A derived CAPS (dCAPS) marker was designed that was specific for the vrn2-1 mutation. Following PCR amplification from genomic DNA with the primers VRN2-AY and VRN2-AZ, the 170 bp product was digested overnight with XmnI restriction enzyme, and the products resolved on a 4% agarose gel. Wild type plants (VRN2) produce a single band of 170 bp following digestion, while vrn2-1 mutants produce two bands, of 137 bp and 33 bp.

Primers Used to Identify VRN2

As indicated on FIG. 3 and FIG. 5. All primer sequences are indicated 5' to 3'.

| | |
|---|---|
| g19247F | ACT GTT CGT CTC CTT CAT CAT G |
| g19247R | TTG CTT GCC TGA AAA AAG TAT G |
| VRN2-C | TGT CGA TAT GCG ACC AGT ACC |
| VRN2-D | CAG GCT TAG ACC CAA TTG ACC |
| VRN2-R | AGG TAG GAT CCG ACA TCG TCT TCT TAT TTA CCG |
| VRN2-S | CTC TTG AAT TCA AAA CTA TTC CTA CTC TCA CAC |
| VRN2-AI | GCC AAT CGG TGT TTT CGC AGC TTT C |
| VRN2-AJ | AAG AAT AAG TTA CAA TCC GAT AAA TCG G |
| VRN2-AL | CAG TGG TTG AAG CTT AAG GAG G |
| VRN2-AM | GCA ATG AAT AAA TCA TAA TCT TGG |
| VRN2-AO | TCT ACT GGG ATG GTA GTT TTC |
| VRN2-AP | ATA TCC CGA GGC AAC AGA GCT TG |
| VRN2-AQ | CAT CTT TGG AAC TCG TTT G |
| VRN2-AR | CTC AGT TGT AAT AGT TGC CC |
| VRN2-AS | AAG AGT GGG CTA TGG CTG G |
| VRN2-AT | GCA ACT CTT TCT CGT AAA ATC TTG |
| VRN2-AU | GCC TCC ATA ACT GTC ATC ACA TC |
| VRN2-AV | TTT CAT TGG TCA TGG CAT GG |
| VRN2-AW | GAC TTC AGA GAT GGG TTT ATG C |
| VRN2-AX | TCC ATA TCT AGC TCC TTC GCC |
| VRN2-AY | TGC GTT CAT TAA GTA GGC AAC AGA AAA TGG |
| VRN2-AZ | GAG AAG TAG TTA CCT TTG TTT TCT TAC AGA AGA GT |

TABLE 1

Comparison of VRN2 Nucleotide and Amino Acid Sequence to Database Sequences

| Sequence | Nucleotides | | | Amino Acids | | | |
|---|---|---|---|---|---|---|---|
| | Identity (%) | Length | Range[a] | Identity (%) | Similarity (%)[b] | Length | Range[c] |
| VRN2 Col | 96.5 | 1722 | 1-1722 | 96.1 | 96.8 | 445 | 1-445 |
| C72616 Region I | 32.4 | 219 | 681-899 | 15.1 | 42.5 | 73 | 151-223 |
| C72616 Region II | 71.7 | 247 | 951-1197 | 72.7 | 85.7 | 82 | 241-322 |
| C72616 Complete | 47.7 | 517 | 681-1197 | 40.1 | 58.1 | 172 | 151-322 |
| AI163743 Region I | 41.0 | 61 | 839-899 | 27.3 | 68.1 | 22 | 202-223 |
| AI163743 Region II | 71.6 | 264 | 951-1214 | 66.7 | 77.1 | 88 | 241-328 |
| AI163743 Complete | 65.8 | 376 | 839-1214 | 52.8 | 66.6 | 127 | 202-328 |
| At Hyp 2245035 | 66.3 | 570 | 924-1493 | 63.7 | 79.5 | 190 | 232-421 |
| KIAA0160 Region I | 36.6 | 396 | 231-626 | 20.4 | 39.4 | 132 | 1-132 |
| KIAA0160 Region II | 35.5 | 904 | 819-1722 | 17.7 | 43.4 | 249 | 197-445 |
| KIAA0160 Complete | 41.1 | 1492 | 231-1722 | 16.0 | 36.0 | 445 | 1-445 |

[a]Numbered relative to VRN2 cDNA sequence
[b]Similarity defined as identity plus similarity on the basis of amino acids grouped into four classes - (D, E), (R, K, H), (S, T, N, Q, Y), and (L, I, V, M, A, G, W, F, P, C)
[c]Numbered relative to VRN2 amino acid sequence

TABLE 2

Putative Domains of the VRN2 Protein

| "Domain" | "Sub-domain" | Length | Position[a] | Identity (%) | Similarity (%)[b] | Molecule |
|---|---|---|---|---|---|---|
| DNA/Protein-Binding | | 70 | 63-132 | 30.0 | 51.4 | KIAA0160 |
| | Zinc Finger Motif | 22 | 90-111 | 50.0 | 68.1 | Mm Spalt 1296845 |
| | | 22 | 90-111 | 45.4 | 68.1 | Sc TFIIIA 730931 |
| | | 22 | 90-111 | 40.1 | 72.7 | Ce Hyp 2854197 |
| | | 22 | 90-111 | 36.4 | 50.0 | KIAA0160 |
| | Conserved Region | 41 | 76-116 | 43.9 | 61.0 | KIAA0160 |
| Activation | | 66 | 263-328 | 89.4 | 95.4 | AI163743 |
| | | 68 | 263-330 | 83.0 | 93.2 | C72616 |
| | | 104 | 263-366 | 58.6 | 76.0 | At Hyp 2245035 |
| | | 104 | 263-366 | 29.8 | 49.0 | KIAA0160 |
| | Conserved Acidic Region | 36 | 281-316 | 94.4 | 97.2 | AI163743 |
| | | 36 | 281-316 | 86.1 | 94.4 | C72616 |
| | | 36 | 281-316 | 58.3 | 72.2 | At Hyp 2254035 |
| | | 36 | 281-316 | 30.5 | 50.0 | KIAA0160 |

[a]Position relative to VRN2 Amino Acid sequence
[b]Similarity was calculated as defined in Table 1

```
CAAGCTTCTTCAATTTTGCTTGCTCTCTCTTACACAGCCAATCGGTGTTTTCGCAGCTTTCA    SEQ ID NO: 1

GGCCTCAATCCAAGACATTCTATATAAGCATATTGCAGAAGAGGCGGTTCTAATTGTTGCAT

TGAGTTTATCGCTATGACGTAGGGAAATTCTAATTTAGGGGAGGCCTCAGAGTTTGCACTAA

CTTCATAATCGGCTCTTGACGTTGTTGAGTGTAATTGAACAAGAATGTGTAGGCAGAATTGT

CGCGCGAAATCCTCACCGGAGGAAGTGATTTCAACTGATGAGAATCTCTTGATATATTGTAA

ACCTGTTCGACTATATAACATCTTTCACCTTCGCTCTCTAGGCAACCCATCGTTTCTTCCAA

GATGCTTGAACTACAAAATTGGAGCAAAGCGCAAAAGAAAGTCAAGATCTACTGGGATGGTA

GTTTTCAACTATAAGGATTGTAATAACACATTACAGAAAACTGAAGTTAGGGAGGATTGTTC

TTGTCCATTTTGCTCTATGCTATGTGGTAGCTTCAAGGGGCTGCAATTTCATTTGAATTCAT

CTCATGATTTATTTGAATTTGAGTTCAAGCTTTTCGAAGAATACCAGACAGTTAATGTTTCT

GTAAAACTTAATTCCTTCATATTTGAGGAAGAAGGAAGTGATGACGATAAATTTGAGCCCTT

CTCTCTCTGCTCGAAACCTCGTAAGCGGAGACAAAGAGGTGGCAGAAATAACACCAGGAGAC

TTAAAGTATGCTTTTTACCGTTGGATTCACCCAGTTTAACTAATGGCACAGAAAATGGAATC

ACCCTACTTAATGATGGAAACCGTGGTTTAGGATATCCCGAGGCAACAGAGCTTGCTGGACA
```

```
ATTTGAGATGACCAGCAACATTCCACCAGCCATAGCCCACTCTTCTCTGGACGCTGGTGCTA

AAGTTATATTGACAAGCGAAGCTGTGGTCCCTGCTACTAAGACAAGAAAGTTATCTGCTGAG

CGATCAGAGGCTAGAAGCCACCTACTTCTTCAGAAACGCCAATTCTATCATTCTCACAGAGT

CCAGCCAATGGCGCTTGAGCAAGTAATGTCTGACCGGGATAGCGAGGATGAAGTCGATGACG

ATGTTGCAGATTTTGAAGATCGCCAGATGCTTGATGACTTTGTGGATGTGAATAAAGATGAA

AAGCAATTCATGCATCTTTGGAACTCGTTTGTAAGAAAACAAAGGGTTATAGCAGATGGTCA

TATCTCTTGGGCATGTGAAGCATTTTCAAGATTTTACGAGAAAGAGTTGCACCGTTACTCAT

CACTCTTCTGGTGTTGGAGATTGTTTTTGATTAAACTATGGAACCATGGACTTGTCGACTCA

GCCACCATCAACAACTGCAATACCATCCTCGAGAATTGCCGTAATAGCTCAGACACCACCAC

CACCAACAACAACAACAGTGTGGATCGTCCCAGTGACTCAAACACCAACAACAATAACATTG

TGGATCATCCCAATGACATAAACAACAAGAACAATGTTGACAACAAGGACAATAACAGCAGA

GACAAAGTAATTAAATAGGAAAATCTCCGGCTTTTATGATACCGATTTATCGGATTGTAACT

TATTCTTCTTTCTTAAAAAATTGTTTAGGAGCAAACAAATTTTTTATATGTTAGTGTATTCA

ACTGATTACATTTTTAGTTAAAAAAAAAAAATGGATTCTGCTTATAACT

MCRQNCRAKSSPEEVISTDENLLIYCKPVRLYNIFHLRSLGNPSFLPRCLNYKIGAKRKRKS     SEQ ID NO: 2

RSTGMVVFNYKDCNNTLQKTEVREDCSCPFCSMLCGSFKGLQFHLNSSHDLFEFEFEKLFEEY

QTVNVSVKLNSFIFEEEGSDDDKFEPFSLCSKPRKRRQRGGRNNTRRLKVCFLPLDSPSLTN

GTENGITLLNDGNRGLGYPEATELAGQFEMTSNIPPAIAHSSLDAGAKVILTSEAVVPATKT

RKLSAERSEARSHLLLQKRQFYHSHRVQPMALEQVMSDRDSEDEVDDDVADFEDRQMLDDFV

DVNKDEKQFMHLWNSFVRKQRVIADGHISWACEAFSRFYEKELHRYSSLFWCWRLFLIKLWN

HGLVDSATINNCNTILENCRNSSDTTTTNNNNSVDRPSDSNTNNNNIVDHPNDINNKNNVDN

KDNNSRDKVIK

AAAGAGAATGCTTTGACTCTCTCATTGGTCAAACCTGACTGTATTTATATGCGTTATTGTGT     SEQ ID NO: 3

GGTAAAGTTTCGACCTTTGACTTTACAAGTTGGCGTTAAGAAGAGAGATGCGTAGATCAGCG

AGTGGTTCGAGAGTTTTGGATCATTTTCCCCCGACTTCACGGTCTCCACGTCGATCTCAGAG

CATTACATCATTGGAAGATGATGTGGAGGTGCTTTTGCCTAGGTACGATCCGAATTCTCAAG

CGGGGAAGAGAGAGAAGTCAAGATTCAGATTTGCAGAAAACGTCATCCATTTGATTCCTCTC

ATTCTTCTTCTCTGTATCGCAATCCTCTGGCTCTCCTCTTATTCAGGTAAGCCGAGAAATTG

ATTCAATCTCTATGAATCCATAATTGATATGTGAAACTTAATTAGGGATTTTACAAAGGCTC

ATATGGATATGATATGAGGATCGAGATGTCTCTGTAACATTAGAATCTTGTGTTGAATTATT

GTTTCAATTTGTTCATATTATACTAAACCGGTGATGGATTTGGAATTTGTCAGCAGCGTTAA

GGAGTTGAGTTCAAGAAGCAACATGTTGTCTTGTCTCCATGGGAACTCATCATATTCAGTTT

TGGGAAAGGAAACAATTTTTTTTACCGCCGGTGATTATGTGCCGCAAACCATACGTAACTTT

TGTAATTTTCGGTTCTGTAGACACATAAAAGGATCTCTCGTTTTCATGAAATGTATGTTTAA

TATTTCACTATACATCACACAACTCAAGTAGAAAACACTGATGGTTATCCATTAATCATCAT

TCTATTGGTCGAAAACAAGGATTAGTTTCAACTTATTGCTACCTTAGTGATTAGATGTTCCT

GTGAGTTTCAGCTAGCCAAGTCAACTAGAGTTAAACAATGGAATCAAATACATATTCAGTA

ATTTATTTTAAACTCTGACTATTTATGTAAACAAAAATGGAAATTAAAATTGAAGGTCATGA

AGATTCTATTCTTAGTATGAAAAGTATAGATCAATGATAAAAGTATATACCAGAACAGTGGT

GGATCTAGAAACATATTTAGTATATGGCACAATATATTTAACATATACAAATTTTAATCTAA
```

-continued

```
AAGTTGTATTCATTTATGAAAAGACWTCTGAATGAAGCAAATTTATTTGATGTGTTAATCAT
CCATTTATGTGTTAATCAGCCATTGATGTTAGTATAGTACTCTATGCTAACATAATTTTTTT
ATACTATAAATTAAAAAAATAGGTAAGAAAAGAAAAATAGATTAATATAAAAAGCATTTTAT
TAGCTGAAATAAATAAAATGAAAGAAGATAATAACTAATTGACTAAAAAATTAGTAGAGCAT
ATGGGCACAATACACTAAGTATTTCATCTTTACTATAAAATGTAACAAATTTCAAAATTAT
CAAACTGTATATAGGGCACGTGCCTAGGTACCAATAGACGTACGTCCGCCCTGAAATAAGTT
GGTGAATATGGTTTTAATTCCTCTAATACTCACTGTACTGCCATGGTAGAGGTGAAAAAAAC
AATTTTAGAAATATTATAATGGATTAAGCTGTCCAAGTTGGTCGTATTTTCTTTACATTTTA
TTAACTAATAAACATAAATAAGTTCAACTATTTATTGACTAGTAATAATACGTGTAAAATGT
CTATTGGTTTAAAATATGGGCCATAAGGCCCAGACTTGAAAAAAAAACTTGAAACCCAAAGT
TATATTTTTACTTGTTTCTTCTTTCTCAGTGAATATCTCCCAATCAAGCTTCTTCGATTTTG
CTCTCTCTTACACAGCCAATCGGTGTTTTCGCAGCTTTCAGGTTTGTCTCAATCTCAAATTA
AATCGGAGTCAAGTAATAACAATTGATAAACCTAATTGTTTCCATTGTATTGTAAGATTTGA
AATTTTGCTGTAGATCCGGAATCGAATTCTAGTTCTGGAATCGTTGATCTCGATGGAATTTT
TTTTTTAAGATTTCTTCTTACACATTTGGTTCAAAAGATCACATAGTTTTATTTTAATTTGA
TAAGTATGATGATTCTGCTAAGTGGCATTGGATAAAGTTTTCGTTTTTGCAATACGTCTAAA
CTTGTCTATGTCTTGAATGAACTCTCTGAGTTGCTTAAAAAGTCTTGTGCTTTCTTTATTAC
ACAGGCCTCAATCCAAGACATTCTATATAAGCATATTGCAGAAGAGGCGGTTCTAATTGTTG
CATTGAGTTTATCGCTATGACGTAGGGAAATTCTAATTTAGGGGAGGCCTCAGAGTTTGCAC
TAACTTCATAATCGGCTCTTGACGTTGTTGAGTGTAATTGAACAAGAATGTGTAGGCAGAAT
TGTCGCGCGAAATCCTCACCGGAGGAAGTGATTTCAACTGATGAGAATCTCTTGATATATTG
TAAACCTGTTCGACTATATAACATCTTTCACCTTCGCTCTCTAGGCAACGTATGATTTGCCT
TCCTCTCTCATCATATTAGCTCAGTAATCTTTCATCTCCTGTGTAGATCACCCACTAATAGT
TTGAGTTTGCTAAGCTGATTATGGTCTGATTCATGGCGAGTGTGTGCTTCTTTTGTCTCCTA
AATTTGAACTTGTTGTTTGTTGTTGCAGCCATCGTTTCTTCCAAGATGCTTGAACTACAAAA
TTGGAGCAAAGCGCAAAAGAAAGTATGTTTTCTTCTTGAATGTAGCTGCTACAGTGATATGT
TATTTATCTTACTTCTAATATGGAAGCTGATGACCTATTTTATCTTTGTTGAGTAGATATGG
ACATAATGAATGGTTTCTTCTTTGTTCATGCTATAAACTTACATTTTATAAAATTGTGTTTT
GGTTAGGTCAAGATCTACTGGGATGGTAGTTTTCAACTATAAGGATTGTAATAACACATTAC
AGAAAACTGAAGGTTAGTCTTTTTCTGTTCGTCGACAAAATTCGATGTCAATGTCTATGTTT
CTCTAGATGATTTGTTATTTACTATTTTTTTCTGTATTGTCATGCAGTTAGGGAGGATTGTT
CTTGTCCATTTTGCTCTATGCTATGTGGTAGCTTCAAGGTGGGCAACTATTACAACTGAGGT
TTCTTCCGGGGCCTTTCATATCTAACACTGTGAAATGCTACTGCTGTTTCATGCTGTATACT
TTCACTGTTTGGTTACATATTTTTGTGTTTGTTGTTTGTCTTCTCACTCTTTTCGAACTGCT
GAGTGTGTGCTTATCTGAGAAAACATGTCCCAGATGGAGCTTACAACCAATTGTCTTGTGTC
TATGCAGGGGCTGCAATTTCATTTGAATTCATCTCATGATTTATTTGAATTTGAGTTCAAGG
TATGTGGTTTTATGGAAATTCTTGATTTGCTATGCCTTTATTAATGAGGTTATAGTTAAAAA
AGGGTCTTTCCTATTGTAGCTTTCGGAAGAATACCAGACAGTTAATGTTTCTGTAAAACTTA
ATTCCTTCATATTTGAGGTCAGTTACTTTAAACTTGGTTAATTGGGAAATCCGATAGCTGGT
GAAAATTTTGTTTATATTCCATCCTTATTTGTACTAGGAAGAAGGAAGTGATGACGATAAAT
```

-continued

```
TTGAGCCCTTCTCTCTCTGGTAACCCTCAGAACCCCTTCGATTAAATACCTTAATAGCAGTA

ACTCCTTGCTTCTCTTGTCAGTACATCTCTGTAAATCCAACCATAATGTTTTGCAGCTCGAA

ACCTCGTAAGCGGAGACAAAGAGGTGGCAGAAATAACACCAGGAGACTTAAAGTATGCTTTT

TACCGTTGGATTCACCCAGTTTAACTAATGGCACAGAAAATGGAATCACCCTACTTAATGAT

GGTAAAATCATATCTTCTTCTGTGCGTTCCTTGTGGCTTAGAACTTCATATTACAGAAGAAG

ATACAATGGCCTGATTGTTTAGTTTTTGTACTTCTCCTCGCATTCTTCTTGCGAGGGTATTG

TTACCAGAACTGATGTACAAAATTAATGGCATGCTACAGGAAACCGTGGTTTAGGATATCCC

GAGGCAACAGARCTTGCTGGACAATTTGAGATGACCAGCAACATTCCACCAGCCATAGCCCA

CTCTTCTCTGGACGCTGGTGCTAAAGTTATATTGACAAGCGAAGCTGTGGTCCCTGCTACTA

AGACAAGAAAGTTATCTGCTGAGCGATCAGAGGCTAGAAGGTTTGTTCATCATGACACCCCG

TCATCATAATTACCATTCCTGTTGTTACAAATGTTCTTCCTATTATGGATAAGTGTTTATAG

TACTGCCATATTAACCGAGAAAATTTCTTCCAGCCACCTACTTCTTCAGAAACGCCAATTCT

ATCATTCTCACAGAGTCCAGGTGATCCAAGTTCCTTCACCTACTTCTTAGGCATTTTCTTTA

AATTGCTCATGATGATATCTTATCAAAGCATACTTGGTTTGTTCTCATCCAAATTTGTATTT

TGATCTGTATGTATCAACGCAAAATAGTTATGTCCATGTTGTCTCCGTTTTATTGCCACTAA

CCAAAAAATGCATGTTTCTGTGACAAGCCAATGGCGCTTGAGCAAGTAATGTCTGACCGGGA

TAGCGAGGATGAAGTCGATGACGATGTTGCAGATTTTGAAGATCGCCAGGTATTCCATGATT

TCTTTCTGCGTTCATTAAATAGACAACAGAAAATGGTATATGATGTAACTTGCTAATGGCTT

TTGAAACTTAAAAAAGCTGCAGATGCTTGATGACTTTGTGGATGTGAATAAAGATGAAAGC

AATTCATGCATCTTTGGAACTCGTTTGTAAGAAAACAAAGGTAACTACTTCTCTTACACATG

AACAGACACAAAAAGACCTTATGTCTTACATTCCATACCTGTCTAAATGATTTTGCTTATGG

AACTTTGAGCTCAATTATGATTGTTGATGTTTCAGGGTTATAGCAGATGGTCATATTTCTTG

GGCATGTGAAGCATTTTCAAGATTTTACGAGAAAGAGTTGCACCGTTACTCATCACTCTTCT

GGTAATATAAGTACACCAAACATATACAGACACATAACTACACTATCAATCTTGTTTCGTTT

TCTGAAAAAAAAATAAAAATTTCCAGGTGTTGGAGATTGTTTTTGATTAAACTATGGAACCA

TGGACTTGTCGACTCAGCCACCATCAACAACTGCAATACCATCCTCGAGAATTGCCGTAATA

GCTCAGACACCACCACCACCAACAACAACAACAGTGTGGATCGTCCCAGTGACTCAAACACC

AACAACAATAACATTGTGGRTCATCCCAATGACATAAACAACAAGAACAATGTTGACAACAA

GGACAATAACAGCAGAGACAAAGTAATTAAATAGGAAAATCTCCGGCTTTTATGATACCGAT

TTATCGGATTGTAACTTATTCTTCTTTCTTAAAAAATTGTTTAGGAGCAAACAAATTTTTA

TATGTTAGTGTATTCAACTGATTACATTTTTAGTTAAAAAAAAAAATGGATTCTGCTTATAA

CTAAAAACTGAAAAAAAAGAAAAGTTTCCTTAATTTTTCTTTTTGACTTGAGAAAAAGCTCC

TCTAGTAAATATGAGTTATATATTAATCAAGTACATAACATAAAAATAGTATATATTAAGTG

CAAATAGATTGAAAACAAATCAAGAAGAAATTAATTAAGACAGAGTGATTAAGCTTAAAACC

CCATTTGGACTTGTTCTTTCTCAATGAATCCCTCACAAGCAGCAAGCTTCTTCGATTTTGCT

TTGACACCACCAATCGGTGTTTTCGAATCTTTCAGGTTTGTCTCGATTTCAATCTAGATCGG

AGTCAAGTAATAAAATTGATTAACCTAAGTATTCCCGTTCTCTCGTAAGAGTTGGGATTTAG

CAGTAGATCGGAAATCGGAATTTACGTTTTTGTTAAAAGATTGATGGTTTAGGTAATGGAAC

ATAGTTCTGGATTCATTGCTTCTAGTTGATTCTCGAATTGTTTGATTTCGCAATGCACATTT

TTGTTTCAAAGGATCACAGAATTTGATTTAAAATTTGACAAAATTCCATCAATTTCTCATAT
```

-continued

TAGGGTTTATATTTCTTCTAGTAACTCGAACTTGTTGGAACTCTGTATACTCTGTGCTATGT

AGATAAAGTCTTAACATTTTGGTCAACTTTGTTTGATCTCTAAACTAGTTTGGGCTCTCTGT

TTTAAAGTTTTGTGCTTTCACTATTACACAGGTCTCATACAAGACTACAGTCTCAAGAAGCA

TAATATCGTCGACTCTGTTTTGAGTTTCTCAACAGTGGTTGAAGCTTAAGGAGGTTCTTATG

TGCGTTTTGATATC

CAAGCTTCTTCAATTTTGCTTGCTCTCTCTCTTACACGGCCAATCGGTGTTTTCGCAGCTTT   SEQ ID NO: 4

CAGGCCTCAATACAAGACATTCTATATAAGCATATTGCAGAAGAGGCGGTTCTAATTGTTGC

ATGGAGTTGAACAATATGACGTAGGGAAATTCTAATTTAGGGGAGGCCTCAGAGTTTGCACT

AACTTCATAATCAGCTCTGGACGTTGTTGATTGTATTTGAACAAGAATGTGTAGGCAGAATT

GTCGCGCGAAATCCTCACCGGAGGAAGTGATTTCAACTGATGAGAATCTCTTGATATATTGT

AAACCTGTTCGACTATATAACATCTTTCACCTTCGCTCTCTAGGCAACCCATCGTTTCTGCC

AAGATGCTTGAACTACAAAATTGGGGCAAAGCGCAAAAGAAAGTCAAGATCTACTGGGATGG

TAGTTTTCAACTATAAGGATTGTAATAATACATTACAAAGAACTGAAGTTAGGGAGGATTGT

TCTTGTCCATTTTGCTCTATGCTATGTGGTAGCTTCAAGGGGCTGCAATTTCATTTGAATTC

ATCTCATGATTTATTTGAATTTGAGTTCAAGCTTTTGGAAGAATACCAGACAGTTAATGTTT

CTGTAAAACTTAATTCCTTCATATTTGAGGAAGAAGGAAGTGATGATGATAAATTTGAGCCC

TTCTCTCTCTGCTCGAAACCTCGTAAGCGTAGACAAAGAGGTGGCAGAAATAACACCAGGAG

ACTTAAAGTATGCTTTTTACCGTTGGATTCACCCAGTTTAGCTAATGGCACAGAAAATGGAA

TTGCCCTGCTGAATGATGGAAACCGTGGTTTAGGATATCCCGAGGCAACAGAGCTTGCTGGA

CAATTTGAGATGACTAGCAACATTCCACCAGCCATAGCCCACTCTTCTCTGGACGCTGGTGC

TAAAGTTATATTAACAACCGAAGCTGTGGTCCCTGCTACTAAGACAAGAAAGTTATCTGCTG

AGCGATCAGAGGCTAGAAGCCACCTACTTCTTCAGAAACGCCAATTCTATCATTCTCACAGA

GTCCAGCCAATGGCGCTTGAGCAAGTAATGTCTGATCGGATAGCGAGGATGAAGTCGATGA

CGATGTTGCAGATTTTGAAGATCGCCAGATGCTTGATGACTTTGTGGATGTGAATAAAGATG

AAAAGCAATTCATGCATCTTTGGAACTCGTTTGTAAGAAAACAAAGGGTTATAGCAGATGGT

CATATCTCTTGGGCATGTGAAGTATTTTCAAGATTTTACGAGAAAGAGTTGCACTGTTACTC

ATCACTCTTCTGGTGTTGGAGATTGTTTTTGATTAAACTATGGAACCATGGACTTGTCGACT

CAGCCACCATCAACAACTGCAATACCATCCTCGAGAATTGCCGTAATACCTCAGTCACTAAC

AACAACAACAACAGTGTGGATCATCCCAGTGACTCAAACACCAACAACAATAACATTGTGGA

TCATCCGAATGACATAAAAAACAAGAACAATGTTGACAACAAGGACAATAACAGCAGAGACA

AGTAATTAAATAGGAAACACTCCGGTTTAGATGATACCGATCTATCGGATTGTAACTTATTC

TTCTTTCTTAAAAAAATTGTTTAGGAGCAAACAAAGATTTTATTTGTTAGTGTATTCAACTG

ATTACATTTTTAGTTAAAAAAATGGATTCTCCTTAATAACT

MCRQNCRAKSSPEEVISTDENLLIYCKPVRLYNIFHLRSLGNPSFLPRCLNYKIGAKRKRKS   SEQ ID NO: 5

RSTGMVVFNYKDCNNTLQRTEVREDCSCPFCSMLCGSFKGLQFHLNSSHDLFEFEFKLLEEY

QTVNVSVKLNSFIFEEEGSDDDKFEPFSLCSKPRKRRQRGGRNNTRRLKVCFLPLDSPSLAN

GTENGIALLNDGNRGLGYPEATELAGQFEMTSNIPPAIAHSSLDAGAKVILTTEAVVPATKT

RKLSAERSEARSHLLLQKRQFYHSHRVQPMALEQVMSDRDSEDEVDDDVADFEDRQMLDDFV

DVNKDEKQFMHLWNSFVRKQRVIADGHISWACEVFSRFYEKELHCYSSLFWCWRLFLIKLWN

HGLVDSATINNCNTILENCRNTSVTNNNNNSVDHPSDSNTNNNNIVDHPNDIKNKNNVDNKD

-continued

NNSRDK

AAAGAGAAGAGCTTTGACTCTCTCATTGGTCAAACCTGACTGTATTTATATGCGTTATTGTG   SEQ ID NO: 6
TGGTAAAGTTTCGACCTTTGACTTGACAAGTTGCCGTTAAGAAGAGAGATGCGTAGATCAGC
GAGTGGTTCTAGAGTTTTGGATCATTTTCCGGCGACTTCAAGGTCTCCGCCTCGATCTCAGA
GTGTTACAGCAATGGAAGATGATGTGGAGCTGCTTTTGCCTAGGTACGATCCGAATTCTCAA
GCGGGGAAGAGAGAGAAATCAAGATTCAGATTTTCAGAAAACGTCATCCATTTGATTCCTCT
CATTCTTCTTCTCTGTGTCGCAATCCTCTGGCTCTCCTCTTACTCAGGTAAGCCGAGAAATT
GTTTCAATCTCTATGAATCCATAATTGATCTGTGAAACTTAATTAGGGATTTTACAAAGACT
CATATGGATATGAGGATCGAGATGTCTCTGCAACGTTAGAATCTTGTGTTGAATTATGGTTT
CAATTTGTTCATATAATACTAAATCGGTGATGGATTTGGAATTTGTCAGCAGCGTTAAGGAG
TTGAGTTCCAAAAGCAACATGTTGTCTTGTCTCCATGGGAACTCATATTCAGTTTTGGGAAA
GGAAACAATTCTTTTACCGCCGGTGATTTTGTGCCGCAAACCATTCGTATTTGTAATTTTTG
GTTCTGTAGACACACAAAAGGATCTCTCGTTTTCATGAAATGTATGTTTAATATTTCAGTGA
TATACATCACACAACTCAAGTAGAAAACACTGATGGTTATCCATTAATCATTCTATTGGTCG
AAAAAAAGATTAGTTTCAACTTAATGCCACCTTAGGATTATATGTTCCTGTGAGTTTCAGCT
AGCCAACTCAACTAGAGTTAAACAATGGAATCAAAATACATATTCAGTAATTTATTTTAAAC
TCTGACTATTTATGTAAAACACAAATGGAAATCAAAATTGAAGGTCATGAAGATTCTATTCT
TAGTGTGAAAAGTATAGATCAATGATTCTTAATTTCTTCATCCTCCACGCATAGATCAATGG
TGAATATGGTTTTAAATCCTCTAATACTCACTGTACTGCCATGGTAGAGTTAAAAAAACAAT
TTTAGAAATATTAGTGGATTAAGGCATTAAGCTGTCCAAGTTGCTTGTATTTTCTTTTCATT
TTATTAATTAAAAAAAAAGTTCAACTATTTATTGACTAATAATAATACGTGTTAAATGGTTA
TCGGTTTAAAATATGGGCCATAGGCCCAGACTTGAAGAAAAACTTGAAACCCAAAGTTTTAT
TTTTACTTGTTTTCTTTCTCAGTGAATATCTCCCAATCAAGCTTCTTCAATTTTGCTTGCTC
TCTCTCTTACACGGCCAATCGGTGTTTTCGCAGCTTTCAGGTTTGTCTCAATCTCAAATTAA
ATCGGAGTCAAGTAATAACAATTGATAACCCTAATTGTTTCAATTATATTGTAAGATTTGAA
ATTTTGCAGTAGATCCGGAATCGTATTCTAGTTCTGGAATCGTTGATCTCGATGGAATTTTT
TTTAAGATTTCTTCATACACATTTGGTTCAAAAGATCACATAATTTTATTTTAATTTGATAA
GTATGATGATTCTGCTAAGTGGCATTGGATAAAGTTTTCATTTTTGCAATACGTCTAAACTT
GTCTATGTCTTGAATGAACTCTCTGAGTTGCTTAAAAAGTCTTGTGCTTTCTTTATTACACA
GGCCTCAATACAAGACATTCTATATAAGCATATTGCAGAAGAGGCGGTTCTAATTGTTGCAT
GGAGTTGAACAATATGACGTAGGGAAATTCTAATTTAGGGGAGGCCTCAGAGTTTGCACTAA
CTTCATAATCAGCTCTGGACGTTGTTGATTGTATTTGAACAAGAATGTGTAGGCAGAATTGT
CGCGCGAAATCCTCACCGGAGGAAGTGATTTCAACTGATGAGAATCTCTTGATATATTGTAA
ACCTGTTCGACTATATAACATCTTTCACCTTCGCTCTCTAGGCAACGTATGATTTGGCCTTC
CTCTCTCATCATTTTAGCTTAGTAATCTTTCATCTCCTGTGTAGATCACCCACTAATAGTTT
GAGTTTGCTAAGCTGATTATGGTCTGACTCATGGCGAGTGTGTGCTTCTTTTGTCTCCTAAT
GTTATTTGAACTTGTTGTTTGTTGTTGCAGCCATCGTTTCTGCCAAGATGCTTGAACTACAA
AATTGGGCAAAGCGCAAAAGAAAGTATGCGTTTCTTCTTGAATGTAGTTGCCACAGTGATA
TGTTATTTATCTTACTTCTAATATGGAAGCTGATGAACTATTTATCTTTGTTGAGTAGATAT
GGACATAATGAATGGTTTCTTCTTTGTTCATGCTATACACTTATATTTTACAAAATTGTGTT

-continued

```
TTGCTTAGGTCAAGATCTACTGGGATGGTAGTTTTCAACTATAAGGATTGTAATAATACATT

ACAAAGAACTGAAGGTTAGTCTTTTTCTGTTCTTCGACAAAATTCGATGTCAATGTCTATGT

TTCTCTAGATGATTTGTTATTTACTATTTTTTTCTGTATTGTCACGCAGTTAGGGAGGATTG

TTCTTGTCCATTTTGCTCTATGCTATGTGGTAGCTTCAAGGTGGGCAACTATTACAACTGAG

GTTTCTTCCGGGGCCTTTCATATCTAACACTGTGAAATGCTACTGCCGTTTAATGCTATATA

CTTTCACTGTTTGGTTACATATTTTTGTGTTTGTTGTTTGTCTTCTTGCTCTTTTTAAACTG

CTGAGTGTGTGCTTATCTGAGAAAACATGTTCCAGTTCGAGCTTACAATCCATTGTCTTGTG

TCTATGCAGGGGCTGCAATTTCATTTGAATTCATCTCATGATTTATTTGAATTTGAGTTCAA

GGTATGTGGTTTTATGGAATTTCTTGTTTTGCCTATGCCGTTAGTAATGAGGTTATAGTTAA

AAAAGGGTCTTTCCTATTGTAGCTTTTGGAAGAATACCAGACAGTTAATGTTTCTGTAAAAC

TTAATTCCTTCATATTTGAGGTCAGTTACTTTAAACTTGGTTAATTGGGAAATCCTATAGCT

GGTGAAAATTTGGTTTATATTCCATCCTTATTTGTACTAGGAAGAAGGAAGTGATGATGATA

AATTTGAGCCCTTCTCTCTCTGGTAACTCTCAGAACCCCTTGATTAAATACCTTAATAGCAG

TAACTCCTTGCTTTTCTTGTCAGTACTTCTCTATAAATCCAACCACAATGTTTTGCAGCTCG

AAACCTCGTAAGCGTAGACAAAGAGGTGGCAGAAATAACACCAGGAGACTTAAAGTATGCTT

TTTACCGTTGGATTCACCCAGTTTAGCTAATGGCACAGAAAATGGAATTGCCCTGCTGAATG

ATGGTAAAATCACATCTTCTTCTGTGGTATTCGTTGTGGCTTAGAACTTCATTTTACAGAAG

AAGATACAATGTCCTGATTGTTTAGTTTTTGTACTTCTCCTCGCATTCTTCTTGTGAGGGTA

ATGTTACCAGAACTGATGTACAAAATTAATGGCATGCTACAGGAAACCGTGGTTTAGGATAT

CCCGAGGCAACAGAGCTTGCTGGACAATTTGAGATGACTAGCAACATTCCACCAGCCATAGC

CCACTCTTCTCTGGACGCTGGTGCTAAAGTTATATTAACAACCGAAGCTGTGGTCCCTGCTA

CTAAGACAAGAAAGTTATCTGCTGAGCGATCAGAGGCTAGAAGGTTTGTTCATCATGACACC

CCGTCATCATAATTACCATACCTGTTGTTACAAATGTTCTTCCTATTATGGATAAGTGTTTA

CTGTACTGCCATATTAACCGAGAAAATTTCTTCCAGCCACCTACTTCTTCAGAAACGCCAAT

TCTATCATTCTCACAGAGTCCAGGTGATCCAAGTTCCTTCACCTACTTCTTAGGCATTTTCT

TTAAATTGCTCATGATGATATCTTATCAAAGCATACTTGGTTTGTTCTCATCTAAATTTGTA

TTTTGATTCTGTATGTATCAACGCAAAAAAATTATGTCCATGTTGTCTCCGTTTTATTGCCA

CTAACCAAAAACTGCATGTTTCTTGTGACAAGCCAATGGCGCTTGAGCAAGTAATGTCTGAT

CGGGATAGCGAGGATGAAGTCGATGACGATGTTGCAGATTTTGAAGATCGCCAGGTATTCCA

TGATTTCTTTCTGCGTTCATTAAGTAGGCAACAGAAAATGGTATACGATGTAACTTGCTAAT

GGCTTTTGAAACTTAAAAAAGCTGCAGATGCTTGATGACTTTGTGGATGTGAATAAAGATGA

AAAGCAATTCATGCATCTTTGGAACTCGTTTGTAAGAAAACAAAGGTAACTACTTCTCTTAC

ACTTGAACACACACAAAAAGACCTTATGTCTTACATTCCATACCTGTCTAAATGATTCTGCT

TATGGAACTTTGAGCTCAAATTATGATTGATGTTTGCAGGGTTATAGCAGATGGTCATATCT

CTTGGGCATGTGAAGTATTTTCAAGATTTTACGAGAAAGAGTTGCACTGTTACTCATCACTC

TTCTGGTAATATAAGTACACCAAACATATACAGACACATAACTACACTATCAATTTTGTTTC

GTTTTTCTGAAAGAAAAATAAAAAAATTCCAGGTGTTGGAGATTGTTTTTGATTAAACTATGG

AACCATGGACTTGTCGACTCAGCCACCATCAACAACTGCAATACCATCCTCGAGAATTGCCG

TAATACCTCAGTCACTAACAACAACAACAACAGTGTGGATCATCCCAGTGACTCAAACACCA

ACAACAATAACATTGTGGATCATCCGAATGACATAAAAAACAAGAACAATGTTGACAACAAG
```

-continued

```
GACAATAACAGCAGAGACAAGTAATTAAATAGGAAACACTCCGGTTTAGATGATACCGATCT

ATCGGATTGTAACTTATTCTTCTTTCTTAAAAAAATTGTTTAGGAGCAAACAAAGATTTTAT

TTGTTAGTGTATTCAACTGATTACATTTTTAGTTAAAAAAATGGATTCTCCTTAATAACTAA

AGACTGAAAAATAAGATAAGTTTCCTTAATTTTTCTTTTTGACTTGAGAAAAAGCTCCTCTA

GACCTCTAGTAAATAGGAGTTATATATTAATCAAGTACATAACATAAAAATATATATATTAA

GTGCAAATAGATTGAAAACAAATCAAGAAATTAATTAAGACACAGTGATTAAGCTTAAAACC

CCATTTTGACTTGTTCTTTCTCAATGAATCCCTCACAAGCAGCAAGCTTCTTCGATTTTGCT

TTGACACCACCAATCAGTGTTTTCGAATCTTTCAGGTTTGTCTCGATTTCAAACTAGATCGG

AGTCAAGTGATAAAATTGACTAACATAATTATTCCCGTTCTCTCGTAAGAGTTGGGATTTAG

CAGTAGATCGGAAATCGGAATTTACGTTTTTGTTAAAAGATTGATGGTTTAGGTAATAAAAC

ATAGTTCTGGATTCATTGCTTCTAGTTGATTCTCGAATTGTTTGATTTCGCAATGCACATTT

TTGGTTCAAAGGATCACATAATTTGCTTTAAAATTTGACAAAACATACCATCAAATTTCTCA

TATTTCTTCAAGTAACTCGAACTTGTTGGAAATCTATATACTCTGGGCTATGTAGATAAAGT

CTTAACATTTTGGTCAACATTGTTTGTTCTCTAAACTAGTTTGGGTTCTCTGTTTTAAAGTT

TGGTGCTTTCACTATTACACAGGTCTTATACAAGACTACAGTCTCTAGAAGCATAATATCGT

CGACTCTGTTTTGAGTTTCCCAACAGTGGTTGAAGCTTAAGGAGGTTCTTATGTGCCTTTTG

AAATC

CAAGCTTCTTCAATTTTGCTTGCTCTCTCTCTTACACGGCCAATCGGTGTTTTCGCAGCTTT    SEQ ID NO: 7

CAGGCCTCAATACAAGACATTCTATATAAGCATATTGCAGAAGAGGCGGTTCTAATTGTTGC

ATGGAGTTGAACAATATGACGTAGGGAAATTCTAATTTAGGGGAGGCCTCAGAGTTTGCACT

AACTTCATAATCAGCTCTGGACGTTGTTGATTGTATTTGAACAAGAATGTGTAGGCAGAATT

GTCGCGCGAAATCCTCACCGGAGGAAGTGATTTCAACTGATGAGAATCTCTTGATATATTGT

AAACCTGTTCGACTATATAACATCTTTCACCTTCGCTCTCTAGGCAACCCATCGTTTCTGCC

AAGATGCTTGAACTACAAAATTGGGGCAAAGCGCAAAAGAAAGTCAAGATCTACTGGGATGG

TAGTTTTCAACTATAAGGATTGTAATAATACATTACAAAGAACTGAAGTTAGGGAGGATTGT

TCTTGTCCATTTTGCTCTATGCTATGTGGTAGCTTCAAGGTGGGCAACTATTACAACTGAGG

GGCTGCAATTTCATTTGAATTCATCTCATGATTTATTTGAATTTGAGTTCAAGCTTTTGGAA

GAATACCAGACAGTTAATGTTTCTGTAAAACTTAATTCCTTCATATTTGAGGAAGAAGGAAG

TGATGATGATAAATTTGAGCCCTTCTCTCTCTGCTCGAAACCTCGTAAGCGTAGACAAAGAG

GTGGCAGAAATAACACCAGGAGACTTAAAGTATGCTTTTTACCGTTGGATTCACCCAGTTTA

GCTAATGGCACAGAAATGGAATTGCCCTGCTGAATGATGGAAACCGTGGTTTAGGATATCC

CGAGGCAACAGAGCTTGCTGGACAATTTGAGATGACTAGCAACATTCCACCAGCCATAGCCC

ACTCTTCTCTGGACGCTGGTGCTAAAGTTATATTAACAACCGAAGCTGTGGTCCCTGCTACT

AAGACAAGAAAGTTATCTGCTGAGCGATCAGAGGCTAGAAGCCACCTACTTCTTCAGAAACG

CCAATTCTATCATTCTCACAGAGTCCAGCCAATGGCGCTTGAGCAAGTAATGTCTGATCGGG

ATAGCGAGGATGAAGTCGATGACGATGTTGCAGATTTTGAAGATCGCCAGATGCTTGATGAC

TTTGTGGATGTGAATAAAGATGAAAAGCAATTCATGCATCTTTGGAACTCGTTTGTAAGAAA

ACAAAGGGTTATAGCAGATGGTCATATCTCTTGGGCATGTGAAGTATTTTCAAGATTTTACG

AGAAAGAGTTGCACTGTTACTCATCACTCTTCTGGTGTTGGAGATTGTTTTTGATTAAACTA

TGGAACCATGGACTTGTCGACTCAGCCACCATCAACAACTGCAATACCATCCTCGAGAATTG
```

-continued

```
CCGTAATACCTCAGTCACTAACAACAACAACAGTGTGGATCATCCCAGTGACTCAAACA

CCAACAACAATAACATTGTGGATCATCCGAATGACATAAAAAACAAGAACAATGTTGACAAC

AAGGACAATAACAGCAGAGACAAGTAATTAAATAGGAAACACTCCGGTTTAGATGATACCGA

TCTATCGGATTGTAACTTATTCTTCTTTCTTAAAAAAATTGTTTAGGAGCAAACAAAGATTT

TATTTGTTAGTGTATTCAACTGATTACATTTTTAGTTAAAAAAATGGATTCTCCTTAATAAC

T
```

| | |
|---|---|
| MCRQNCRAKSSPEEVISTDENLLIYCKPVRLYNIFHLRSLGNPSFLPRCLNYKIGAKRKRKS<br>RSTGMVVFNYKDCNNTLQRTEVREDCSCPFCSMLCGSFKVGNYYN | SEQ ID NO: 8 |

```
ACATTTTCGTACCGCTCAAGATTTAAGAAGCGTAAAAGGGTGGAAATCTCAAGTGATAAAAT    SEQ ID NO: 9

TAGGCATGTACATCCACATATTGTGGATTCAGGATCACCTGAAGATGCCCAGGCAGGATCTG

AAGACGATTACGTGCAGAGGGAAAATGGTAGTTCTGTAGCACACGCTTCTGTTGATCCTGCT

AATTCATTACACGGTAGCAATCTTTCAGCACCAACAGTGTTACAGTTTGGGAAGACAAGAAA

GCTGTCTGTTGAACGAGCTGATCCCAGAAATCGGCAGCTCCTACAAAAACGCCAGTTCTTTC

ATTCTCACAGGGCTCAACCAATGGCATTGGGAGCAGTTTTCTCAGATCGTGATAGTGAAGAT

GAGGTTGATGATGACATTGCTGATTTTGAAGATAGACAGATGCTTGATGATTTTGTTGATGT

TACCAAAGACGAACTTATTATGCATATGG
```

| | |
|---|---|
| TFSYRSRFKKRKRVEISSDKIRHVHPHIVDSGSPEDAQAGSEDDYVQRENGSSVAHASVDPA<br>NSLHGSNLSAPTVLQFGKTRKLSVERADPRNRQLLQKRQFFHSHRAQPMALGAVFSDRDSED<br>EVDDDIADFEDRQMLDDFVDVTKDELIMHM | SEQ ID NO: 10 |

```
ACATGCATATCCTGATGCTGAATGTGCTCAATTGGTACCTGGGAATAATCTTCCACCTCCTG    SEQ ID NO: 11

CCATGCTACAATTTGCAAAGACAAGAAAATTATCAATTGAACGGTCTGACATGAGAAACCGT

ACACTCCTTCACAAACGACAATTTTTTCACTCACATAGAGCTCAGCCAATGGCAGCTGAGCA

AGTTATGTCAGATCGGGATAGTGAGGATGAAGTTGACGATGATGTTGCAGATTTTGAAGACC

GAAGGATGCTTGATGATTTTGTAGACGTGACTAAAGATGAGAAGCAAATGATGCACTTGTGG

AACTCATTTGTGAGG
```

| | |
|---|---|
| HAYPDAECAQLVPGNNLAPPAMLQFAKTRKLSIERSDMRNRTLLHKRQFFHSHRAQPMAAEQ<br>VMSDRDSEDEVDDDVADFEDRRMLDDFVDVTKDEKQMMHLWNSFVR | SEQ ID NO: 12 |

```
ATGGATCCGATTAAGCTGACAACAGAAGCTAAGGTCCCTGCTAAGCGATCAAAGGCTACAAG    SEQ ID NO: 13

CCACTACTTGCCTCTTCATAAACGCCAGTTCTATCATTCCCGAACCGGTCAGCCATTGTCAC

TTGAGCAAGTTATGTCTGACCGAGATAGCGAAAATGACGTCGACAAAAATGATGATGCTGCA

CATCTCGAAGAAAGCCAGATGCTTAATGGTTCCATGGATGAGAATGAAATCGTAGCAGAGAG

ATTCATAAAACTTTGGAACTCCTTTGTTAAACAGCAAAGGATTGTTGCAGATGCTCATATTC

CTTGGGCATGTGAAGCATTCTCAAGATTACACCTGCAAGAGCTGCGCAGTAACTTATCACTC

GACTTGTGCTGGAGACAATTCATGATCAAACAATGGGATTATGGACTTCTTGACAGAGTCAC

CATGAACAAATGCAATACCATCATCTACCATAATATCTCAACTACCAACGATGACATAAACA

ATAACAACACAAGGACGACTGATAATATGGATGTTGTCGACGATGACATAAACAGAGACAAG
```

| | |
|---|---|
| MDPIKLTTEAKVPAKRSKATSHYLPLHKRQFYHSRTGQPLSEQVMSDRDSENDVDKNDDAA<br>HLEESQMLNGSMDENEIVAERFIKLWNSFVKQQRIVADAHIPWACEAFSRLHLQELRSNLSL<br>DLCWRQFMIKQWDYGLLDRVTMNKCNTIIYHNISTTNDDINNNNTRTTDNMDVVDDDINRDK | SEQ ID NO: 14 |

```
CTCTGAGGAGACACTTTTTTTTTCCTCCCTCCTTCCCTCCTCTCCTCCTCCCTTCCCTTCCC    SEQ ID NO: 15
```

-continued

```
CTCTCCTCCCCTCTCTCCTCCTTCCCCCCTCGGTCCGCCGGAGCCTGCTGGGGCGAGCGGTT
GGTATTGCAGGCGCTTGCTCTCCGGGGCCGCCCGGCGGGTAGCTGGCGGGGGAGGAGGCAG
GAACCGCGATGGCGCCTCAGAAGCACGGCGGTGGGGGAGGGGCGGCTCGGGCCCAGCGCG
GGGTCCGGGGGAGGCGGCTTCGGGGGTTCGGCGGCGGTGGCGGCGGCGACGGCTTCGGGCGG
CAAATCCGGCGGCGGGAGCTGTGGAGGGGTGGCAGTTACTCGGCCTCCTCCTCCTCCTCCG
CGGCGGCAGCGGCGGGGCTGCGGTGTTACCGGTGAAGAAGCCGAAAATGGAGCACGTCCAG
GCTGACCACGAGCTTTTCCTCCAGGCCTTTGAGAAGCCAACACAGATCTATAGATTTCTTCG
AACTCGGAATCTCATAGCACCAATATTTTTGCACAGAACTCTTACTTACATGTCTCATCGAA
ACTCCAGAACAAACATCAAAAGGAAAACATTTAAAGTTGATGATATGTTATCAAAAGTAGAG
AAAATGAAAGGAGAGCAAGAATCTCATAGCTTGTCAGCTCATTTGCAGCTTACGTTTACTGG
TTTCTTCCACAAAAATGATAAGCCATCACCAAACTCAGAAAATGAACAAAATTCTGTTACCC
TGGAAGTCCTGCTTGTGAAAGTTTGCCACAAAAAAAGAAAGGATGTAAGTTGTCCAATAAGG
CAAGTTCCCACAGGTAAAAAGCAGGTGCCTTTGATTCCTGACCTCAATCAAACAAAACCCGG
AAATTTCCCGTCCCTTGCAGTTTCCAGTAATGAATTTGAACCTAGTAACAGCCATATGGTGA
AGTCTTACTCGTTGCTATTTAGAGTGACTCGTCCAGGAAGAAGAGAGTTTAATGGAATGATT
AATGGAGAAACCAATGAAAATATTGATGTCAATGAAGAGCTTCCAGCCAGAAGAAAACGAAA
TCGTGAGGATGGGGAAAAGACATTTGTTGCACAAATGACAGTATTTGATAAAAACAGGCGCT
TACAGCTTTTAGATGGGGAATATGAAGTAGCCATGCAGGAAATGGAAGAATGTCCAATAAGC
AAGAAAAGAGCAACATGGGAGACTATTCTTGATGGGAAGAGGCTGCCTCCATTCGAAACATT
TTCTCAGGGACCTACGTTGCAGTTCACTCTTCGTTGGACAGGAGAGACCAATGATAAATCTA
CGGCTCCTATTGCCAAACCTCTTGCCACTAGAAATTCAGAGAGTCTCCATCAGGAAAACAAG
CCTGGTTCAGTTAAACCTACTCAAACTATTGCTGTTAAAGAATCATTGACTACAGATCTACA
AACAAGAAAAGAAAAGGATACTCCAAATGAAAACCGACAAAAATTAAGAATATTTTATCAGT
TTCTCTATAACAACAATACAAGGCAACAAACTGAAGCAAGAGATGACCTGCATTGCCCTTGG
TGTACTCTGAACTGCCGCAAACTTTATAGTTTACTCAAGCATCTTAAACTCTGCCATAGCAG
ATTTATCTTCAACTATGTTTATCATCCAAAAGGTGCTAGGATAGATGTTTCTATCAATGAGT
GTTATGATGGCTCCTATGCAGGAAATCCTCAGGATATTCATCGCCAACCTGGATTTGCTTTT
AGTCGCAACGGACCAGTTAAGAGAACACCTATCACACATATTCTTGTGTGCAGGCCAAAACG
AACAAAAGCAAGCATGTCTGAATTTCTTGAATCTGAAGATGGGGAAGTAGAACAGCAAAGAA
CATATAGTAGTGGCCACAATCGTCTGTATTTCCATAGTGATACCTGCTTACCTCTCCGTCCA
CAAGAAATGGAAGTAGATAGTGAAGATGAAAAGGATCCTGAATGGCTAAGAGAAAAAACCAT
TACACAAATTGAAGAGTTTTCTGATGTTAATGAAGGAGAGAAAGAAGTGATGAAACTCTGGA
ATCTCCATGTCATGAAGCATGGGTTTATTGCTGACAATCAAATGAATCATGCCTGTATGCTG
TTTGTAGAAAATTATGGACAGAAAATAATTAAGAAGAATTTATGTCGAAACTTCATGCTTCA
TCTAGTCAGCATGCATGACTTTAATCTTATTAGCATAATGTCAATAGATAAAGCTGTTACCA
AGCTCCGTGAAATGCAGCAAAAATTAGAAAAGGGGGAATCTGCTTCCCCTGCAAACGAAGAA
ATAACTGAAGAACAAAATGGGACAGCAAATGGATTTAGTGAAATTAACTCAAAAGAGAAAGC
TTTGGAAACAGATAGTGTCTCAGGGGTTTCAAAACAGAGCAAAAAACAAAAACTCTGAAAAG
CTCTAACCCCATGTTATGGACAAACACTGAAATTACATTTTAGGGAATTCATCCTCTAAGAA
TTATGTTTTTGTTTTTAATCATATGTTCCAAACAGGCACTGTTAGATGAAGTAAATGATTTC
```

```
                                          -continued
AACAAGGATATTTGTATCAGGGTTCTACTTCACTTCATTATGCAGCATTACATGTATATCAC

TTTTATTGATGTCATTAAAACATTCTGTACTTTAAGCATGAAAAGCAATATTTCAAAGTATT

TTTAAACTCAACAAATGTCATCAAATATGTTGAATTGATCTAGAAATTATTTCATATATAAA

TCAGAATTTTTTTGCATTTATGAACGGCTGTTTTTCTACTTTGTAATTGTGAGACATTTTCT

TGGGGAGGGAAAATTGGAATGGTTCCCTTTTTTAGAAATTGAAGTGGTCTTCATATGTCAAC

TACAGAAAAGGAAAAAAATAGAAATTGAAGGATTTTTATGAAATTATATTGCATTACTATTT

GCAGTCAAACTTTGATCCTTGTTTTTGAAATCATTTGTCAATTCGGAATGAAAAATTATAAT

GTAATTTTACATTACATAAGTTCCTTTTACAATTAAAAAATAGCACTTCTTCATCTTATGCC

TGTTTGAGAAGATATTAAATTTTCACATTGTTGACAGTGAAATGCTATGTTGGTTTATAAGA

TTACAGACCATTTGTTTTCATGTGGATAATTTTAGTGCATTGCTCACCCGGTATGTTTTTTT

TTTTTAACTTGAACATTTTGCTTGTTTTGTTTTTCTTTTTTAATTAGATAATCACACGGAAA

ATTAAGCTGTTCATATCTTTAAATTAGGATTGCAAACCAAGGAAAGAACGCATTTGAGATTT

TAAGATGTCACTTATAAGGGGAGAAGTGTTCTTAAAAAGTCAACCAGAAAACTGTTATGCCT

TTTATTTGTTTGCAAGGATGTCTTTGTAATGTGTTTCATGAATAGAATATCCAATAGAGATA

AGCTGACTTGAATCATTTTGAGCAATTTTGCCCTGTGTTATATGTGTTTCACGCACATATTT

GCAGTTGGATTTTCTCCAACAGAAAGTGGATTCACTACTGGCACATTAACAAGCACCAATAG

GTTTTTATTCCAACTCCGAGCACTGTGGTTGAGTAACATCACCTCAATTTTTTATTATCCTT

AAAGATATTGCATTTTCATATTCTTTATTTATAAAGGATCAATGCTGCTGTAAATACAGGTA

TTTTTAATTTTAAAATTTCATTCCACCACCATCAGATGCAGTTCCCTATTTTGTTTAATGAA

GGGATATATAAGCTTTCTAATGGTGTCTTCAGAAATTTATAAAATGTAAATACTGATTTGAC

TGGTCTTTAAGATGTGTTTAACTGTGAGGCTATTTAACGAATAGTGTGGATGTGATTTGTCA

TCCAGTATTAAGTTCTTAGTCATTGATTTTTGTGTTTAAAAAAAAATAGGAAAGAGGGAAAC

TGCAGCTTTCATTACAGATTCCTTGATTGGTAAGCTCTCCAAATGATGAGTTCTAGTAAACT

CTGATTTTTGCCTCTGGATAGTAGATCTCGAGCGTTTATCTCGGGCTTTAATTTGCTAAAGC

TGTGCACATATGTAAAAAAAAAAAAAAAAAAGATTATTTTAGGGGAGATGTAGGTGTAGAATT

ATTGCTTATGTCATTTCTTAAGCAGTTATGCTCTTAATGCTTAAAAGAAGGCTAGCATTGTT

TGCACAAAAAGTTGGTGATTCCCACCCCAAATAGTAATAAAATTACTTCTGTTGAGTAAACT

TTTTATGTCATCGTAAAAGCTGGAAAAATCCCTTTGTTTCTATTTATAAAAAAGTGCTTTT

CTATATGTACCCTTGATAACAGATTTTGAAGAAATCCTGTAAGATGATAAAGCATTTGAATG

GTACAGTAGATGTAAAAAAAATTCAGTTTAAAAGAACATTTGTTTTTACATTAAATGTTTAT

TTGAAATCAAATGATTTTGTACATAAAGTTCAATAATAT

LRRHFFFPPSFPPLLLPSLPLSSPLSSFPPRSAGACWGERLVLQALALRGRPAGSWRGEEAG      SEQ ID NO: 16

TAMAPQKHGGGGGGGSGPSAGSGGGGFGGSAAVAAATASGGKSGGGSCGGGGSYSASSSSSA

AAAAGAAVLPVKKPKMEHVQADHELFLQAFEKPTQIYRFLRTRNLIAPIFLHRTLTYMSHRN

SRTNIKRKTFKVDDMLSKVEKMKGEQESHSLSAHLQLTFTGFFHKNDKPSPNSENEQNSVTL

EVLLVKVCHKKRKDVSCPIRQVPTGKKQVPLIPDLNQTKPGNFPSLAVSSNEFEPSNSHMVK

SYSLLFRVTRPGRREFNGMINGETNENIDVNEELPARRKRNREDGEKTFVAQMTVFDKNRRL

QLLDGEYEVAMQEMEECPISKKRATWETILDGKRLPPFETFSQGPTLQFTLRWTGETNDKST

APIAKPLATRNSESLHQENKPGSVKPTQTIAVKESLTTDLQTRKEKDTPNENRQKLRIFYQF

LYNNNTRQQTEARDDLHCPWCTLNCRKLYSLLKHLKLCHSRFIFNYVYHPKGARIDVSINEC
```

-continued

YDGSYAGNPQDIHRQPGFAFSRNGPVKRTPITHILVCRPKRTKASMSEFLESEDGEVEQQRT

YSSGHNRLYFHSDTCLPLRPQEMEVDSEDEKDPEWLREKTITQIEEFSDVNEGEKEVMKLWN

LHVMKHGFIADNQMNHACMLFVENYGQKIIKKNLCRNFMLHLVSMHDFNLISIMSIDKAVTK

LREMQQKLEKGESASPANEEITEEQNGTANGFSEINSKEKALETDSVSGVSKQSKKQKL

---

The invention claimed is:

1. An isolated nucleic acid encoding a VRN2 polypeptide of SEQ ID NO: 2, said polypeptide regulating one or more physical characteristics of a plant into which the nucleic acid is introduced, the physical characteristics being selected from the group consisting of vernalization response, flowering time, leaf size and shape and shade avoidance response.

2. The nucleic acid according to claim 1 which reduces the vernalization requirement of the plant for flowering.

3. An isolated nucleic acid comprising SEQ ID NO. 1 or a sequence encoding a polypeptide having at least 95% identity to SEQ ID NO: 2, said nucleic acid encoding a polypeptide which complements the phenotype of a vrn2 mutant and also regulates a plant physical characteristic selected from the group consisting of at least one of vernalization response, flowering time, leaf size and shape or shade avoidance response when expressed in a plant cell.

4. The nucleic acid according to claim 3 wherein the VRN2 polynucleotide sequence is obtained from a plant species other than *Arabidopsis thaliana*.

* * * * *

SEQUENCE LISTING

<160> NUMBER OF SEQ ID NOS: 77

<210> SEQ ID NO 1
<211> LENGTH: 1722
<212> TYPE: DNA
<213> ORGANISM: Arabidopsis thaliana

<400> SEQUENCE: 1

```
caagcttctt caattttgct tgctctctct tacacagcca atcggtgttt tcgcagcttt      60
caggcctcaa tccaagacat tctatataag catattgcag aagaggcggt tctaattgtt     120
gcattgagtt tatcgctatg acgtagggaa attctaattt aggggaggcc tcagagtttg     180
cactaacttc ataatcggct cttgacgttg ttgagtgtaa ttgaacaaga atgtgtaggc     240
agaattgtcg cgcgaaatcc tcaccggagg aagtgatttc aactgatgag aatctcttga     300
tatattgtaa acctgttcga ctatataaca tctttcacct tcgctctcta ggcaacccat     360
cgtttcttcc aagatgcttg aactacaaaa ttggagcaaa gcgcaaaaga aagtcaagat     420
ctactgggat ggtagttttc aactataagg attgtaataa cacattacag aaaactgaag     480
ttagggagga ttgttcttgt ccatttttgct ctatgctatg tggtagcttc aagggcgctgc    540 aatttcattt gaattcatct catgatttat ttgaatttga gttcaagctt ttcgaagaat     600
accagacagt taatgtttct gtaaaactta attccttcat atttgaggaa gaggaagtg      660 atgacgataa atttgagccc ttctctctct gctcgaaacc tcgtaagcgg agacaaagag     720
gtggcagaaa taacaccagg agacttaaag tatgcttttt accgttggat tcacccagtt     780
taactaatgg cacagaaaat ggaatcaccc tacttaatga tggaaaccgt ggtttaggat     840
atcccgaggc aacagagctt gctggacaat ttgagatgac cagcaacatt ccaccagcca     900
tagcccactc ttctctggac gctggtgcta agttatatt gacaagcgaa gctgtggtcc      960
ctgctactaa gacaagaaag ttatctgctg agcgatcaga ggctagaagc cacctacttc    1020
ttcagaaacg ccaattctat cattctcaca gagtccagcc aatggcgctt gagcaagtaa    1080
tgtctgaccg ggatagcgag gatgaagtcg atgacgatgt tgcagatttt gaagatcgcc    1140
agatgcttga tgactttgtg gatgtgaata agatgaaaa gcaattcatg catctttgga    1200
actcgtttgt aagaaaacaa agggttatag cagatggtca tatctcttgg gcatgtgaag    1260
cattttcaag attttacgag aaagagttgc accgttactc atcactcttc tggtgttgga    1320
gattgttttt gattaaacta tggaaccatg gacttgtcga ctcagccacc atcaacaact    1380
gcaataccat cctcgagaat tgccgtaata gctcagacac caccaccacc aacaacaaca    1440
acagtgtgga tcgtcccagt gactcaaaca ccaacaacaa taacattgtg gatcatccca    1500
atgacataaa caacaagaac aatgttgaca acaaggacaa taacagcaga gacaaagtaa    1560
ttaaatagga aaatctccgg ctttttatgat accgatttat cggattgtaa cttattcttc    1620
tttcttaaaa aattgtttag gagcaaacaa attttttata tgttagtgta ttcaactgat    1680
```

```
tacattttta gttaaaaaaa aaaatggatt ctgcttataa ct                    1722
```

<210> SEQ ID NO 2
<211> LENGTH: 445
<212> TYPE: PRT
<213> ORGANISM: Arabidopsis thaliana

<400> SEQUENCE: 2

```
Met Cys Arg Gln Asn Cys Arg Ala Lys Ser Ser Pro Glu Glu Val Ile
 1               5                  10                  15

Ser Thr Asp Glu Asn Leu Leu Ile Tyr Cys Lys Pro Val Arg Leu Tyr
            20                  25                  30

Asn Ile Phe His Leu Arg Ser Leu Gly Asn Pro Ser Phe Leu Pro Arg
        35                  40                  45

Cys Leu Asn Tyr Lys Ile Gly Ala Lys Arg Lys Ser Arg Ser
    50                  55                  60

Thr Gly Met Val Val Phe Asn Tyr Lys Asp Cys Asn Thr Leu Gln
65                  70                  75                  80

Lys Thr Glu Val Arg Glu Asp Cys Ser Cys Pro Phe Cys Ser Met Leu
                85                  90                  95

Cys Gly Ser Phe Lys Gly Leu Gln Phe His Leu Asn Ser Ser His Asp
            100                 105                 110

Leu Phe Glu Phe Glu Phe Lys Leu Phe Glu Glu Tyr Gln Thr Val Asn
        115                 120                 125

Val Ser Val Lys Leu Asn Ser Phe Ile Phe Glu Glu Glu Gly Ser Asp
    130                 135                 140

Asp Asp Lys Phe Glu Pro Phe Ser Leu Cys Ser Lys Pro Arg Lys Arg
145                 150                 155                 160

Arg Gln Arg Gly Gly Arg Asn Asn Thr Arg Arg Leu Lys Val Cys Phe
                165                 170                 175

Leu Pro Leu Asp Ser Pro Ser Leu Thr Asn Gly Thr Glu Asn Gly Ile
            180                 185                 190

Thr Leu Leu Asn Asp Gly Asn Arg Gly Leu Gly Tyr Pro Glu Ala Thr
        195                 200                 205

Glu Leu Ala Gly Gln Phe Glu Met Thr Ser Asn Ile Pro Pro Ala Ile
    210                 215                 220

Ala His Ser Ser Leu Asp Ala Gly Ala Lys Val Ile Leu Thr Ser Glu
225                 230                 235                 240

Ala Val Val Pro Ala Thr Lys Thr Arg Lys Leu Ser Ala Glu Arg Ser
                245                 250                 255

Glu Ala Arg Ser His Leu Leu Leu Gln Lys Arg Gln Phe Tyr His Ser
            260                 265                 270

His Arg Val Gln Pro Met Ala Leu Glu Gln Val Met Ser Asp Arg Asp
        275                 280                 285

Ser Glu Asp Glu Val Asp Asp Val Ala Asp Phe Glu Asp Arg Gln
    290                 295                 300

Met Leu Asp Asp Phe Val Asp Val Asn Lys Asp Glu Lys Gln Phe Met
305                 310                 315                 320

His Leu Trp Asn Ser Phe Val Arg Lys Gln Arg Val Ile Ala Asp Gly
                325                 330                 335

His Ile Ser Trp Ala Cys Glu Ala Phe Ser Arg Phe Tyr Glu Lys Glu
            340                 345                 350

Leu His Arg Tyr Ser Ser Leu Phe Trp Cys Trp Arg Leu Phe Leu Ile
        355                 360                 365
```

```
Lys Leu Trp Asn His Gly Leu Val Asp Ser Ala Thr Ile Asn Asn Cys
        370                 375                 380

Asn Thr Ile Leu Glu Asn Cys Arg Asn Ser Ser Asp Thr Thr Thr Thr
385                 390                 395                 400

Asn Asn Asn Asn Ser Val Asp Arg Pro Ser Asp Ser Asn Thr Asn Asn
                405                 410                 415

Asn Asn Ile Val Asp His Pro Asn Asp Ile Asn Asn Lys Asn Asn Val
            420                 425                 430

Asp Asn Lys Asp Asn Asn Ser Arg Asp Lys Val Ile Lys
        435                 440                 445

<210> SEQ ID NO 3
<211> LENGTH: 6338
<212> TYPE: DNA
<213> ORGANISM: Arabidopsis thaliana

<400> SEQUENCE: 3
```

| | | | | | |
|---|---|---|---|---|---|
| aaagagaatg | ctttgactct | ctcattggtc | aaacctgact | gtatttatat | gcgttattgt | 60 |
| gtggtaaagt | ttcgaccttt | gactttacaa | gttggcgtta | agaagagaga | tgcgtagatc | 120 |
| agcgagtggt | tcgagagttt | tggatcattt | tcccccgact | tcacggtctc | cacgtcgatc | 180 |
| tcagagcatt | acatcattgg | aagatgatgt | ggaggtgctt | ttgcctaggt | acgatccgaa | 240 |
| ttctcaagcg | gggaagagag | agaagtcaag | attcagattt | gcagaaaacg | tcatccattt | 300 |
| gattcctctc | attcttcttc | tctgtatcgc | aatcctctgg | ctctcctctt | attcaggtaa | 360 |
| gccgagaaat | tgattcaatc | tctatgaatc | cataattgat | atgtgaaact | taattaggga | 420 |
| ttttacaaag | gctcatatgg | atatgatatg | aggatcgaga | tgtctctgta | acattagaat | 480 |
| cttgtgttga | attattgttt | caatttgttc | atattatact | aaaccggtga | tggatttgga | 540 |
| atttgtcagc | agcgttaagg | agttgagttc | aagaagcaac | atgttgtctt | gtctccatgg | 600 |
| gaactcatca | tattcagttt | tgggaaagga | acaattttt | tttaccgccg | gtgattatgt | 660 |
| gccgcaaacc | atacgtaact | tttgtaattt | tcggttctgt | agacacataa | aaggatctct | 720 |
| cgttttcatg | aaatgtatgt | ttaatatttc | actatacatc | acacaactca | agtagaaaac | 780 |
| actgatggtt | atccattaat | catcattcta | ttggtcgaaa | acaaggatta | gtttcaactt | 840 |
| attgctacct | tagtgattag | atgttcctgt | gagtttcagc | tagccaagtc | aactagagtt | 900 |
| aaacaatgga | atcaaaatac | atattcagta | atttatttta | aactctgact | atttatgtaa | 960 |
| acaaaaatgg | aaattaaaat | tgaaggtcat | gaagattcta | ttcttagtat | gaaaagtata | 1020 |
| gatcaatgat | aaaagtatat | accagaacag | tggtggatct | agaaacatat | ttagtatatg | 1080 |
| gcacaatata | tttaacatat | acaaattta | atctaaaagt | tgtattcatt | tatgaaaaga | 1140 |
| cwtctgaatg | aagcaaattt | atttgatgtg | ttaatcatcc | atttatgtgt | taatcagcca | 1200 |
| ttgatgttag | tatagtactc | tatgctaaca | taatttttt | atactataaa | ttaaaaaaat | 1260 |
| aggtaagaaa | agaaaaatag | attaatataa | aaagcatttt | attagctgaa | ataaataaaa | 1320 |
| tgaaagaaga | taataactaa | ttgactaaaa | aattagtaga | gcatatgggg | cacaatacac | 1380 |
| taagtatttc | atctttacta | taaaatgtaa | caaatttcaa | aattatcaaa | ctgtatatag | 1440 |
| ggcacgtgcc | taggtaccaa | tagacgtacg | tccgccctga | aataagttgg | tgaatatggt | 1500 |
| tttaattcct | ctaatactca | ctgtactgcc | atggtagagg | tgaaaaaaac | aattttagaa | 1560 |
| atattataat | ggattaagct | gtccaagttg | gtcgtatttt | ctttacattt | tattaactaa | 1620 |
| taaacataaa | taagttcaac | tatttattga | ctagtaataa | tacgtgtaaa | atgtctattg | 1680 |

```
gtttaaaata tgggccataa ggcccagact tgaaaaaaaa acttgaaacc caaagttata    1740
tttttacttg tttcttcttt ctcagtgaat atctcccaat caagcttctt cgattttgct    1800
ctctcttaca cagccaatcg gtgttttcgc agctttcagg tttgtctcaa tctcaaatta    1860
aatcggagtc aagtaataac aattgataaa cctaattgtt tccattgtat tgtaagattt    1920
gaaattttgc tgtagatccg gaatcgaatt ctagttctgg aatcgttgat ctcgatggaa    1980
tttttttttt aagatttctt cttacacatt tggttcaaaa gatcacatag ttttatttta    2040
atttgataag tatgatgatt ctgctaagtg gcattggata agttttcgt ttttgcaata    2100
cgtctaaact tgtctatgtc ttgaatgaac tctctgagtt gcttaaaaag tcttgtgctt    2160
tctttattac acaggcctca atccaagaca ttctatataa gcatattgca gaagaggcgg    2220
ttctaattgt tgcattgagt ttatcgctat gacgtaggga aattctaatt taggggaggc    2280
ctcagagttt gcactaactt cataatcggc tcttgacgtt gttgagtgta attgaacaag    2340
aatgtgtagg cagaattgtc gcgcgaaatc ctcaccggag gaagtgattt caactgatga    2400
gaatctcttg atatattgta aacctgttcg actatataac atctttcacc ttcgctctct    2460
aggcaacgta tgatttgcct tcctctctca tcatattagc tcagtaatct ttcatctcct    2520
gtgtagatca cccactaata gtttgagttt gctaagctga ttatggtctg attcatggcg    2580
agtgtgtgct tctttttgtct cctaaatttg aacttgttgt ttgttgttgc agccatcgtt    2640
tcttccaaga tgcttgaact acaaaattgg agcaaagcgc aaaagaaagt atgttttctt    2700
cttgaatgta gctgctacag tgatatgtta tttatcttac ttctaatatg gaagctgatg    2760
acctatttta tctttgttga gtagatatgg acataatgaa tggtttcttc tttgttcatg    2820
ctataaactt acatttttata aaattgtgtt ttggttaggt caagatctac tgggatggta    2880
gttttcaact ataaggattg taataacaca ttacagaaaa ctgaaggtta gtctttttct    2940
gttcgtcgac aaaattcgat gtcaatgtct atgtttctct agatgatttg ttatttacta    3000
ttttttttctg tattgtcatg cagttaggga ggattgttct tgtccatttt gctctatgct    3060
atgtggtagc ttcaaggtgg gcaactatta caactgaggt ttcttccggg gcctttcata    3120
tctaacactg tgaaatgcta ctgctgtttc atgctgtata ctttcactgt ttggttacat    3180
attttttgtgt ttgttgtttg tcttctcact cttttcgaac tgctgagtgt gtgcttatct    3240
gagaaaacat gtcccagatg gagcttacaa ccaattgtct tgtgtctatg cagggctgc    3300
aatttcattt gaattcatct catgattat ttgaatttga gttcaaggta tgtggtttta    3360
tggaaattct tgatttgcta tgcctttatt aatgaggtta tagttaaaaa agggtctttc    3420
ctattgtagc tttcggaaga ataccagaca gttaatgttt ctgtaaaact taattccttc    3480
atatttgagg tcagttactt taaacttggt taattgggaa atccgatagc tggtgaaaat    3540
tttgttata ttccatcctt atttgtacta ggaagaagga agtgatgacg ataaatttga    3600
gcccttctct ctctggtaac cctcagaacc ccttcgatta aataccttaa tagcagtaac    3660
tccttgcttc tcttgtcagt acatctctgt aaatccaacc ataatgtttt gcagctcgaa    3720
acctcgtaag cggagacaaa gaggtggcag aaataacacc aggagactta aagtatgctt    3780
tttaccgttg gattcaccca gtttaactaa tggcacagaa aatggaatca ccctacttaa    3840
tgatggtaaa atcatatctt cttctgtgcg ttccttgtgg cttagaactt catattacag    3900
aagaagatac aatggcctga ttgtttagtt tttgtacttc tcctcgcatt cttcttgcga    3960
gggtattgtt accagaactg atgtacaaaa ttaatggcat gctacaggaa accgtggttt    4020
aggatatccc gaggcaacag arcttgctgg acaatttgag atgaccagca acattccacc    4080
```

```
agccatagcc cactcttctc tggacgctgg tgctaaagtt atattgacaa gcgaagctgt    4140
ggtccctgct actaagacaa gaaagttatc tgctgagcga tcagaggcta gaaggtttgt    4200
tcatcatgac accccgtcat cataattacc attcctgttg ttacaaatgt tcttcctatt    4260
atggataagt gtttatagta ctgccatatt aaccgagaaa atttcttcca gccacctact    4320
tcttcagaaa cgccaattct atcattctca cagagtccag gtgatccaag ttccttcacc    4380
tacttcttag gcattttctt taaattgctc atgatgatat cttatcaaag catacttggt    4440
ttgttctcat ccaaatttgt attttgatct gtatgtatca acgcaaaata gttatgtcca    4500
tgttgtctcc gttttattgc cactaaccaa aaaatgcatg tttctgtgac aagccaatgg    4560
cgcttgagca gtaatgtct gaccgggata gcgaggatga agtcgatgac gatgttgcag    4620
attttgaaga tcgccaggta ttccatgatt tctttctgcg ttcattaaat agacaacaga    4680
aaatggtata tgatgtaact tgctaatggc ttttgaaact taaaaaagct gcagatgctt    4740
gatgactttg tggatgtgaa taagatgaa aagcaattca tgcatctttg gaactcgttt    4800
gtaagaaaac aaaggtaact acttctctta cacatgaaca gacacaaaaa gaccttatgt    4860
cttacattcc atacctgtct aaatgatttt gcttatggaa ctttgagctc aattatgatt    4920
gttgatgttt cagggttata gcagatggtc atatttcttg ggcatgtgaa gcattttcaa    4980
gattttacga gaaagagttg caccgttact catcactctt ctggtaatat aagtacacca    5040
aacatataca gacacataac tacactatca atcttgtttc gttttctgaa aaaaaaataa    5100
aaatttccag gtgttggaga ttgttttga ttaaactatg gaaccatgga cttgtcgact    5160
cagccaccat caacaactgc aataccatcc tcgagaattg ccgtaatagc tcagacacca    5220
ccaccaccaa caacaacaac agtgtggatc gtcccagtga ctcaaacacc aacaacaata    5280
acattgtggr tcatcccaat gacataaaca acaagaacaa tgttgacaac aaggacaata    5340
acagcagaga caaagtaatt aaataggaaa atctccggct tttatgatac cgatttatcg    5400
gattgtaact tattcttctt tcttaaaaaa ttgtttagga gcaaacaaat tttttatatg    5460
ttagtgtatt caactgatta cattttagt taaaaaaaaa aatggattct gcttataact    5520
aaaaactgaa aaaaagaaa agtttcctta attttcttt ttgacttgag aaaaagctcc    5580
tctagtaaat atgagttata tattaatcaa gtacataaca taaaaatagt atatattaag    5640
tgcaaataga ttgaaaacaa atcaagaaga aattaattaa gacagagtga ttaagcttaa    5700
aaccccattt ggacttgttc tttctcaatg aatccctcac aagcagcaag cttcttcgat    5760
tttgctttga caccaccaat cggtgttttc gaatctttca ggtttgtctc gatttcaatc    5820
tagatcggag tcaagtaata aaattgatta acctaagtat tcccgttctc tcgtaagagt    5880
tgggatttag cagtagatcg gaaatcggaa tttacgtttt tgttaaaaga ttgatggttt    5940
aggtaatgga acatagttct ggattcattg cttctagttg attctcgaat tgtttgattt    6000
cgcaatgcac attttttgttt caaggatca cagaatttga tttaaaattt gacaaaattc    6060
catcaatttc tcatattagg gtttatattt cttctagtaa ctcgaacttg ttggaactct    6120
gtatactctg tgctatgtag ataaagtctt aacatttgg tcaactttgt ttgatctcta    6180
aactagtttg ggctctctgt tttaaagttt tgtgctttca ctattacaca ggtctcatac    6240
aagactacag tctcaagaag cataatatcg tcgactctgt tttgagtttc tcaacagtgg    6300
ttgaagctta aggaggttct tatgtgcgtt ttgatatc                            6338
```

<210> SEQ ID NO 4

<211> LENGTH: 1715
<212> TYPE: DNA
<213> ORGANISM: Arabidopsis thaliana

<400> SEQUENCE: 4

```
caagcttctt caattttgct tgctctctct cttacacggc caatcggtgt tttcgcagct      60
ttcaggcctc aatacaagac attctatata agcatattgc agaagaggcg gttctaattg     120
ttgcatggag ttgaacaata tgacgtaggg aaattctaat ttaggggagg cctcagagtt     180
tgcactaact tcataatcag ctctggacgt tgttgattgt atttgaacaa gaatgtgtag     240
gcagaattgt cgcgcgaaat cctcaccgga ggaagtgatt caactgatg agaatctctt      300
gatatattgt aaacctgttc gactatataa catctttcac cttcgctctc taggcaaccc     360
atcgtttctg ccaagatgct tgaactacaa aattggggca agcgcaaaa gaaagtcaag       420
atctactggg atggtagttt tcaactataa ggattgtaat aatacattac aaagaactga     480
agttagggag gattgttctt gtccattttg ctctatgcta tgtggtagct tcaaggggct     540
gcaatttcat ttgaattcat ctcatgattt atttgaattt gagttcaagc ttttggaaga     600
ataccagaca gttaatgttt ctgtaaaact taattccttc atatttgagg aagaaggaag     660
tgatgatgat aaatttgagc ccttctctct ctgctcgaaa cctcgtaagc gtagacaaag     720
aggtggcaga ataacacca ggagacttaa agtatgcttt ttaccgttgg attcacccag       780
tttagctaat ggcacagaaa atggaattgc cctgctgaat gatggaaacc gtggtttagg     840
atatcccgag gcaacagagc ttgctggaca atttgagatg actagcaaca ttccaccagc     900
catagcccac tcttctctgg acgctggtgc taaagttata ttaacaaccg aagctgtggt     960
ccctgctact aagacaagaa agttatctgc tgagcgatca gaggctagaa gccacctact    1020
tcttcagaaa cgccaattct atcattctca cagagtccag ccaatggcgc ttgagcaagt    1080
aatgtctgat cgggatagcg aggatgaagt cgatgacgat gttgcagatt ttgaagatcg    1140
ccagatgctt gatgactttg tggatgtgaa taaagatgaa aagcaattca tgcatctttg    1200
gaactcgttt gtaagaaaac aaagggttat agcagatggt catatctctt gggcatgtga    1260
agtattttca agattttacg agaaagagtt gcactgttac tcatcactct tctggtgttg    1320
gagattgttt tgattaaac tatggaacca tggacttgtc gactcagcca ccatcaacaa     1380
ctgcaatacc atcctcgaga attgccgtaa tacctcagtc actaacaaca acaacaacag    1440
tgtggatcat cccagtgact caaacaccaa caacaataac attgtggatc atccgaatga    1500
cataaaaaac aagaacaatg ttgacaacaa ggacaataac agcagagaca gtaattaaa     1560
taggaaacac tccggtttag atgataccga tctatcggat tgtaacttat tcttctttct    1620
taaaaaaatt gtttaggagc aaacaaagat tttatttgtt agtgtattca actgattaca    1680
tttttagtta aaaaaatgga ttctccttaa taact                               1715
```

<210> SEQ ID NO 5
<211> LENGTH: 440
<212> TYPE: PRT
<213> ORGANISM: Arabidopsis thaliana

<400> SEQUENCE: 5

Met Cys Arg Gln Asn Cys Arg Ala Lys Ser Ser Pro Glu Glu Val Ile
1               5                   10                  15

Ser Thr Asp Glu Asn Leu Leu Ile Tyr Cys Lys Pro Val Arg Leu Tyr
            20                  25                  30

Asn Ile Phe His Leu Arg Ser Leu Gly Asn Pro Ser Phe Leu Pro Arg

```
                35                  40                  45
Cys Leu Asn Tyr Lys Ile Gly Ala Lys Arg Lys Arg Lys Ser Arg Ser
         50                  55                  60

Thr Gly Met Val Val Phe Asn Tyr Lys Asp Cys Asn Asn Thr Leu Gln
 65                  70                  75                  80

Arg Thr Glu Val Arg Glu Asp Cys Ser Cys Pro Phe Cys Ser Met Leu
                 85                  90                  95

Cys Gly Ser Phe Lys Gly Leu Gln Phe His Leu Asn Ser Ser His Asp
                100                 105                 110

Leu Phe Glu Phe Glu Phe Lys Leu Leu Glu Glu Tyr Gln Thr Val Asn
            115                 120                 125

Val Ser Val Lys Leu Asn Ser Phe Ile Phe Glu Glu Glu Gly Ser Asp
        130                 135                 140

Asp Asp Lys Phe Glu Pro Phe Ser Leu Cys Ser Lys Pro Arg Lys Arg
145                 150                 155                 160

Arg Gln Arg Gly Gly Arg Asn Asn Thr Arg Arg Leu Lys Val Cys Phe
                165                 170                 175

Leu Pro Leu Asp Ser Pro Ser Leu Ala Asn Gly Thr Glu Asn Gly Ile
            180                 185                 190

Ala Leu Leu Asn Asp Gly Asn Arg Gly Leu Gly Tyr Pro Glu Ala Thr
        195                 200                 205

Glu Leu Ala Gly Gln Phe Glu Met Thr Ser Asn Ile Pro Pro Ala Ile
    210                 215                 220

Ala His Ser Ser Leu Asp Ala Gly Ala Lys Val Ile Leu Thr Thr Glu
225                 230                 235                 240

Ala Val Val Pro Ala Thr Lys Thr Arg Lys Leu Ser Ala Glu Arg Ser
                245                 250                 255

Glu Ala Arg Ser His Leu Leu Leu Gln Lys Arg Gln Phe Tyr His Ser
            260                 265                 270

His Arg Val Gln Pro Met Ala Leu Glu Gln Val Met Ser Asp Arg Asp
        275                 280                 285

Ser Glu Asp Glu Val Asp Asp Val Ala Asp Phe Glu Asp Arg Gln
    290                 295                 300

Met Leu Asp Asp Phe Val Asp Val Asn Lys Asp Glu Lys Gln Phe Met
305                 310                 315                 320

His Leu Trp Asn Ser Phe Val Arg Lys Gln Arg Val Ile Ala Asp Gly
                325                 330                 335

His Ile Ser Trp Ala Cys Glu Val Phe Ser Arg Phe Tyr Glu Lys Glu
            340                 345                 350

Leu His Cys Tyr Ser Ser Leu Phe Trp Cys Trp Arg Leu Phe Leu Ile
        355                 360                 365

Lys Leu Trp Asn His Gly Leu Val Asp Ser Ala Thr Ile Asn Asn Cys
    370                 375                 380

Asn Thr Ile Leu Glu Asn Cys Arg Asn Thr Ser Val Thr Asn Asn Asn
385                 390                 395                 400

Asn Asn Ser Val Asp His Pro Ser Asp Ser Thr Asn Asn Asn Asn
                405                 410                 415

Ile Val Asp His Pro Asn Asp Ile Lys Asn Lys Asn Asn Val Asp Asn
            420                 425                 430

Lys Asp Asn Asn Ser Arg Asp Lys
        435                 440

<210> SEQ ID NO 6
```

<211> LENGTH: 5895
<212> TYPE: DNA
<213> ORGANISM: Arabidopsis thaliana

<400> SEQUENCE: 6

| | | | | | |
|---|---|---|---|---|---|
| aaagagaaga | gctttgactc | tctcattggt | caaacctgac | tgtatttata | tgcgttattg | 60 |
| tgtggtaaag | tttcgacctt | tgacttgaca | agttgccgtt | aagaagagag | atgcgtagat | 120 |
| cagcgagtgg | ttctagagtt | ttggatcatt | ttccggcgac | ttcaaggtct | ccgcctcgat | 180 |
| ctcagagtgt | tacagcaatg | gaagatgatg | tggagctgct | tttgcctagg | tacgatccga | 240 |
| attctcaagc | ggggaagaga | gagaaatcaa | gattcagatt | ttcagaaaac | gtcatccatt | 300 |
| tgattcctct | cattcttctt | ctctgtgtcg | caatcctctg | gctctcctct | tactcaggta | 360 |
| agccgagaaa | ttgtttcaat | ctctatgaat | ccataattga | tctgtgaaac | ttaattaggg | 420 |
| attttacaaa | gactcatatg | gatatgagga | tcgagatgtc | tctgcaacgt | tagaatcttg | 480 |
| tgttgaatta | tggtttcaat | ttgttcatat | aatactaaat | cggtgatgga | tttggaattt | 540 |
| gtcagcagcg | ttaaggagtt | gagttccaaa | agcaacatgt | tgtcttgtct | ccatgggaac | 600 |
| tcatattcag | ttttgggaaa | ggaaacaatt | cttttaccgc | cggtgatttt | gtgccgcaaa | 660 |
| ccattcgtat | ttgtaatttt | tggttctgta | gacacacaaa | aggatctctc | gttttcatga | 720 |
| aatgtatgtt | taatatttca | gtgatataca | tcacacaact | caagtagaaa | acactgatgg | 780 |
| ttatccatta | atcattctat | tggtcgaaaa | aaagattagt | ttcaacttaa | tgccacctta | 840 |
| ggattatatg | ttcctgtgag | tttcagctag | ccaactcaac | tagagttaaa | caatggaatc | 900 |
| aaaatacata | ttcagtaatt | tattttaaac | tctgactatt | tatgtaaaac | acaaatggaa | 960 |
| atcaaaattg | aaggtcatga | agattctatt | cttagtgtga | aaagtataga | tcaatgattc | 1020 |
| ttaatttctt | catcctccac | gcatagatca | atggtgaata | tggttttaaa | tcctctaata | 1080 |
| ctcactgtac | tgccatggta | gagttaaaaa | acaattttta | gaaatattag | tggattaagg | 1140 |
| cattaagctg | tccaagttgc | ttgtatttt c | ttttcattt t | attaattaaa | aaaaaagttc | 1200 |
| aactatttat | tgactaataa | taatacgtgt | taaatggtta | tcggtttaaa | atatgggcca | 1260 |
| taggcccaga | cttgaagaaa | aacttgaaac | ccaaagtttt | attttt actt | gttttctttc | 1320 |
| tcagtgaata | tctcccaatc | aagcttcttc | aattttgctt | gctctctctc | ttacacggcc | 1380 |
| aatcggtgtt | ttcgcagctt | tcaggtttgt | ctcaatctca | aattaaatcg | gagtcaagta | 1440 |
| ataacaattg | ataaccctaa | ttgtttcaat | tatattgtaa | gatttgaaat | tttgcagtag | 1500 |
| atccggaatc | gtattctagt | tctggaatcg | ttgatctcga | tggaattttt | tttaagattt | 1560 |
| cttcatacac | atttggttca | aaagatcaca | taattttatt | ttaatttgat | aagtatgatg | 1620 |
| attctgctaa | gtggcattgg | ataaagtttt | catttttgca | atacgtctaa | acttgtctat | 1680 |
| gtcttgaatg | aactctctga | gttgcttaaa | aagtcttgtg | ctttctttat | tacacaggcc | 1740 |
| tcaatacaag | acattctata | taagcatatt | gcagaagagg | cggttctaat | tgttgcatgg | 1800 |
| agttgaacaa | tatgacgtag | ggaaattcta | atttagggga | ggcctcagag | tttgcactaa | 1860 |
| cttcataatc | agctctggac | gttgttgatt | gtatttgaac | aagaatgtgt | aggcagaatt | 1920 |
| gtcgcgcgaa | atcctcaccg | gaggaagtga | tttcaactga | tgagaatctc | ttgatatatt | 1980 |
| gtaaacctgt | tcgactatat | aacatctttc | accttcgctc | tctaggcaac | gtatgatttg | 2040 |
| gccttcctct | ctcatcattt | tagcttagta | atctttcatc | tcctgtgtag | atcacccact | 2100 |
| aatagtttga | gttgctaag | ctgattatgg | tctgactcat | ggcgagtgtg | tgcttctttt | 2160 |
| gtctcctaat | gttatttgaa | cttgttgttt | gttgttgcag | ccatcgtttc | tgccaagatg | 2220 |

```
cttgaactac aaaattgggg caaagcgcaa agaaagtat  gcgtttcttc ttgaatgtag    2280
ttgccacagt gatatgttat ttatcttact tctaatatgg aagctgatga actatttatc    2340
tttgttgagt agatatggac ataatgaatg gtttcttctt tgttcatgct atacacttat    2400
attttacaaa attgtgtttt gcttaggtca agatctactg ggatggtagt tttcaactat    2460
aaggattgta ataatacatt acaaagaact gaaggttagt cttttctgt  tcttcgacaa    2520 aattcgatgt caatgtctat gtttctctag atgatttgtt atttactatt ttttctgta     2580 ttgtcacgca gttagggagg attgttcttg tccattttgc tctatgctat gtggtagctt    2640
caaggtgggc aactattaca actgaggttt cttccggggc ctttcatatc taacactgtg    2700
aaatgctact gccgtttaat gctatatact ttcactgttt ggttacatat ttttgtgttt    2760
gttgtttgtc ttcttgctct ttttaaactg ctgagtgtgt gcttatctga gaaaacatgt    2820
tccagttcga gcttacaatc cattgtcttg tgtctatgca ggggctgcaa tttcatttga    2880
attcatctca tgatttattt gaatttgagt tcaaggtatg tggttttatg gaatttcttg    2940
ttttgcctat gccgttagta atgaggttat agttaaaaaa gggtctttcc tattgtagct    3000
tttggaagaa taccagacag ttaatgtttc tgtaaaactt aattccttca tatttgaggt    3060
cagttacttt aaacttggtt aattgggaaa tcctatagct ggtgaaaatt tggtttatat    3120
tccatcctta tttgtactag gaagaaggaa gtgatgatga taaatttgag cccttctctc    3180
tctggtaact ctcagaaccc cttgattaaa taccttaata gcagtaactc cttgcttttc    3240
ttgtcagtac ttctctataa atccaaccac aatgttttgc agctcgaaac ctcgtaagcg    3300
tagacaaaga ggtggcagaa ataacaccag gagacttaaa gtatgctttt taccgttgga    3360
ttcacccagt ttagctaatg gcacagaaaa tggaattgcc ctgctgaatg atggtaaaat    3420
cacatcttct tctgtggtat tcgttgtggc ttagaacttc attttacaga agaagataca    3480
atgtcctgat tgtttagttt ttgtacttct cctcgcattc ttcttgtgag ggtaatgtta    3540
ccagaactga tgtacaaaat taatggcatg ctacaggaaa ccgtggttta ggatatcccg    3600
aggcaacaga gcttgctgga caatttgaga tgactagcaa cattccacca gccatagccc    3660
actcttctct ggacgctggt gctaaagtta tattaacaac cgaagctgtg gtccctgcta    3720
ctaagacaag aaagttatct gctgagcgat cagaggctag aaggtttgtt catcatgaca    3780
ccccgtcatc ataattacca tacctgttgt tacaaatgtt cttcctatta tggataagtg    3840
tttactgtac tgccatatta accgagaaaa tttcttccag ccacctactt cttcagaaac    3900
gccaattcta tcattctcac agagtccagg tgatccaagt tccttcacct acttcttagg    3960 catttcttt  aaattgctca tgatgatatc ttatcaaagc atacttggtt tgttctcatc    4020
taaatttgta ttttgattct gtatgtatca acgcaaaaaa attatgtcca tgttgtctcc    4080
gttttattgc cactaaccaa aaactgcatg tttcttgtga caagccaatg gcgcttgagc    4140
aagtaatgtc tgatcgggat agcgaggatg aagtcgatga cgatgttgca gattttgaag    4200
atcgccaggt attccatgat ttctttctgc gttcattaag taggcaacag aaaatggtat    4260
acgatgtaac ttgctaatgg cttttgaaac ttaaaaaagc tgcagatgct tgatgacttt    4320
gtggatgtga ataagatga  aaagcaattc atgcatcttt ggaactcgtt tgtaagaaaa    4380
caaaggtaac tacttctctt acacttgaac acacacaaaa agaccttatg tcttacattc    4440
catacctgtc taaatgattc tgcttatgga actttgagct caaattatga ttgatgtttg    4500
cagggttata gcagatggtc atatctcttg ggcatgtgaa gtattttcaa gattttacga    4560
```

-continued

| | |
|---|---|
| gaaagagttg cactgttact catcactctt ctggtaatat aagtacacca aacatataca | 4620 |
| gacacataac tacactatca attttgtttc gttttctga aagaaaaata aaaattcca | 4680 |
| ggtgttggag attgttttg attaaactat ggaaccatgg acttgtcgac tcagccacca | 4740 |
| tcaacaactg caataccatc ctcgagaatt gccgtaatac ctcagtcact aacaacaaca | 4800 |
| acaacagtgt ggatcatccc agtgactcaa acaccaacaa caataacatt gtggatcatc | 4860 |
| cgaatgacat aaaaaacaag aacaatgttg acaacaagga caataacagc agagacaagt | 4920 |
| aattaaatag gaaacactcc ggtttagatg ataccgatct atcggattgt aacttattct | 4980 |
| tctttcttaa aaaaattgtt taggagcaaa caaagatttt atttgttagt gtattcaact | 5040 |
| gattacattt ttagttaaaa aaatggattc tccttaataa ctaaagactg aaaaataaga | 5100 |
| taagtttcct taattttct ttttgacttg agaaaaagct cctctagacc tctagtaaat | 5160 |
| aggagttata tattaatcaa gtacataaca taaaaatata tatattaagt gcaaatagat | 5220 |
| tgaaaacaaa tcaagaaatt aattaagaca cagtgattaa gcttaaaacc ccattttgac | 5280 |
| ttgttctttc tcaatgaatc cctcacaagc agcaagcttc ttcgattttg ctttgacacc | 5340 |
| accaatcagt gttttcgaat cttcaggtt tgtctcgatt tcaaactaga tcggagtcaa | 5400 |
| gtgataaaat tgactaacat aattattccc gttctctcgt aagagttggg atttagcagt | 5460 |
| agatcggaaa tcggaattta cgttttgtt aaaagattga tggtttaggt aataaaacat | 5520 |
| agttctggat tcattgcttc tagttgattc tcgaattgtt tgatttcgca atgcacattt | 5580 |
| ttggttcaaa ggatcacata atttgcttta aaatttgaca aaacatacca tcaaattct | 5640 |
| catatttctt caagtaactc gaacttgttg gaaatctata tactctgggc tatgtagata | 5700 |
| aagtcttaac atttggtca acattgtttg ttctctaaac tagtttgggt tctctgtttt | 5760 |
| aaagtttggt gctttcacta ttacacaggt cttatacaag actacagtct ctagaagcat | 5820 |
| aatatcgtcg actctgtttt gagtttccca acagtggttg aagcttaagg aggttcttat | 5880 |
| gtgccttttg aaatc | 5895 |

<210> SEQ ID NO 7
<211> LENGTH: 1737
<212> TYPE: DNA
<213> ORGANISM: Arabidopsis thaliana

<400> SEQUENCE: 7

| | |
|---|---|
| caagcttctt caattttgct tgctctctct cttacacggc caatcggtgt tttcgcagct | 60 |
| ttcaggcctc aatacaagac attctatata agcatattgc agaagaggcg gttctaattg | 120 |
| ttgcatggag ttgaacaata tgacgtaggg aaattctaat ttaggggagg cctcagagtt | 180 |
| tgcactaact tcataatcag ctctggacgt tgttgattgt atttgaacaa gaatgtgtag | 240 |
| gcagaattgt cgcgcgaaat cctcaccgga ggaagtgatt tcaactgatg agaatctctt | 300 |
| gatatattgt aaacctgttc gactatataa catctttcac cttcgctctc taggcaaccc | 360 |
| atcgtttctg ccaagatgct tgaactacaa aattggggca agcgcaaaa gaaagtcaag | 420 |
| atctactggg atggtagttt tcaactataa ggattgtaat aatacattac aaagaactga | 480 |
| agttagggag gattgttctt gtccattttg ctctatgcta tgtggtagct tcaaggtggg | 540 |
| caactattac aactgagggg ctgcaatttc atttgaattc atctcatgat ttatttgaat | 600 |
| ttgagttcaa gcttttggaa gaataccaga cagttaatgt ttctgtaaaa cttaattcct | 660 |
| tcatatttga ggaagaagga agtgatgatg ataaatttga gcccttctct ctctgctcga | 720 |
| aacctcgtaa gcgtagacaa agaggtggca gaaataacac caggagactt aaagtatgct | 780 |

-continued

```
ttttaccgtt ggattcaccc agtttagcta atggcacaga aaatggaatt gccctgctga      840
atgatggaaa ccgtggttta ggatatcccg aggcaacaga gcttgctgga caatttgaga      900
tgactagcaa cattccacca gccatagccc actcttctct ggacgctggt gctaaagtta      960
tattaacaac cgaagctgtg gtccctgcta ctaagacaag aaagttatct gctgagcgat     1020
cagaggctag aagccaccta cttcttcaga acgccaatt ctatcattct cacagagtcc      1080
agccaatggc gcttgagcaa gtaatgtctg atcgggatag cgaggatgaa gtcgatgacg     1140
atgttgcaga ttttgaagat cgccagatgc ttgatgactt tgtggatgtg aataaagatg     1200
aaaagcaatt catgcatctt tggaactcgt tgtaagaaa acaaagggtt atagcagatg      1260
gtcatatctc ttgggcatgt gaagtatttt caagatttta cgagaaagag ttgcactgtt     1320
actcatcact cttctggtgt tggagattgt ttttgattaa actatggaac catggacttg     1380
tcgactcagc caccatcaac aactgcaata ccatcctcga gaattgccgt aatacctcag     1440
tcactaacaa caacaacaac agtgtggatc atcccagtga ctcaaacacc aacaacaata     1500
acattgtgga tcatccgaat gacataaaaa acaagaacaa tgttgacaac aaggacaata     1560
acagcagaga caagtaatta aataggaaac actccggttt agatgatacc gatctatcgg     1620
attgtaactt attcttcttt cttaaaaaaa ttgtttagga gcaaacaaag attttatttg     1680
ttagtgtatt caactgatta cattttttagt taaaaaatg gattctcctt aataact        1737
```

<210> SEQ ID NO 8
<211> LENGTH: 107
<212> TYPE: PRT
<213> ORGANISM: Arabidopsis thaliana

<400> SEQUENCE: 8

```
Met Cys Arg Gln Asn Cys Arg Ala Lys Ser Ser Pro Glu Glu Val Ile
  1               5                  10                  15

Ser Thr Asp Glu Asn Leu Leu Ile Tyr Cys Lys Pro Val Arg Leu Tyr
             20                  25                  30

Asn Ile Phe His Leu Arg Ser Leu Gly Asn Pro Ser Phe Leu Pro Arg
         35                  40                  45

Cys Leu Asn Tyr Lys Ile Gly Ala Lys Arg Lys Arg Lys Ser Arg Ser
     50                  55                  60

Thr Gly Met Val Val Phe Asn Tyr Lys Asp Cys Asn Asn Thr Leu Gln
 65                  70                  75                  80

Arg Thr Glu Val Arg Glu Asp Cys Ser Cys Pro Phe Cys Ser Met Leu
                 85                  90                  95

Cys Gly Ser Phe Lys Val Gly Asn Tyr Tyr Asn
            100                 105
```

<210> SEQ ID NO 9
<211> LENGTH: 463
<212> TYPE: DNA
<213> ORGANISM: Oryza sativa

<400> SEQUENCE: 9

```
acattttcgt accgctcaag atttaagaag cgtaaaaggg tggaaatctc aagtgataaa       60
attaggcatg tacatccaca tattgtggat tcaggatcac ctgaagatgc ccaggcagga      120
tctgaagacg attacgtgca gagggaaaat ggtagttctg tagcacacgc ttctgttgat      180
cctgctaatt cattacacgg tagcaatctt tcagcaccaa cagtgttaca gtttgggaag      240
acaagaaagc tgtctgttga acgagctgat cccagaaatc ggcagctcct acaaaaacgc      300
```

```
cagttctttc attctcacag ggctcaacca atggcattgg gagcagtttt ctcagatcgt    360
gatagtgaag atgaggttga tgatgacatt gctgattttg aagatagaca gatgcttgat    420
gattttgttg atgttaccaa agacgaactt attatgcata tgg                      463
```

<210> SEQ ID NO 10
<211> LENGTH: 154
<212> TYPE: PRT
<213> ORGANISM: Oryza sativa

<400> SEQUENCE: 10

```
Thr Phe Ser Tyr Arg Ser Arg Phe Lys Lys Arg Lys Arg Val Glu Ile
 1               5                  10                  15

Ser Ser Asp Lys Ile Arg His Val His Pro His Ile Val Asp Ser Gly
            20                  25                  30

Ser Pro Glu Asp Ala Gln Ala Gly Ser Glu Asp Asp Tyr Val Gln Arg
        35                  40                  45

Glu Asn Gly Ser Ser Val Ala His Ala Ser Val Asp Pro Ala Asn Ser
    50                  55                  60

Leu His Gly Ser Asn Leu Ser Ala Pro Thr Val Leu Gln Phe Gly Lys
65                  70                  75                  80

Thr Arg Lys Leu Ser Val Glu Arg Ala Asp Pro Arg Asn Arg Gln Leu
                85                  90                  95

Leu Gln Lys Arg Gln Phe Phe His Ser His Arg Ala Gln Pro Met Ala
            100                 105                 110

Leu Gly Ala Val Phe Ser Asp Arg Asp Ser Glu Asp Glu Val Asp Asp
        115                 120                 125

Asp Ile Ala Asp Phe Glu Asp Arg Gln Met Leu Asp Asp Phe Val Asp
    130                 135                 140

Val Thr Lys Asp Glu Leu Ile Met His Met
145                 150
```

<210> SEQ ID NO 11
<211> LENGTH: 325
<212> TYPE: DNA
<213> ORGANISM: Populus tremula x Populus tremuloides

<400> SEQUENCE: 11

```
acatgcatat cctgatgctg aatgtgctca attggtacct gggaataatc ttgcacctcc     60
tgccatgcta caatttgcaa agacaagaaa attatcaatt gaacggtctg acatgagaaa    120
ccgtacactc cttcacaaac gacaatttt tcactcacat agagctcagc caatggcagc    180
tgagcaagtt atgtcagatc gggatagtga ggatgaagtt gacgatgatg ttgcagattt    240
tgaagaccga aggatgcttg atgattttgt agacgtgact aaagatgaga agcaaatgat    300
gcacttgtgg aactcatttg tgagg                                          325
```

<210> SEQ ID NO 12
<211> LENGTH: 108
<212> TYPE: PRT
<213> ORGANISM: Populus tremula x Populus tremuloides

<400> SEQUENCE: 12

```
His Ala Tyr Pro Asp Ala Glu Cys Ala Gln Leu Val Pro Gly Asn Asn
 1               5                  10                  15

Leu Ala Pro Pro Ala Met Leu Gln Phe Ala Lys Thr Arg Lys Leu Ser
            20                  25                  30
```

```
Ile Glu Arg Ser Asp Met Arg Asn Arg Thr Leu Leu His Lys Arg Gln
            35                  40                  45

Phe Phe His Ser His Arg Ala Gln Pro Met Ala Ala Glu Gln Val Met
    50                  55                  60

Ser Asp Arg Asp Ser Glu Asp Val Asp Asp Val Ala Asp Phe
65                  70                  75                  80

Glu Asp Arg Arg Met Leu Asp Asp Phe Val Asp Val Thr Lys Asp Glu
                85                  90                  95

Lys Gln Met Met His Leu Trp Asn Ser Phe Val Arg
            100                 105

<210> SEQ ID NO 13
<211> LENGTH: 558
<212> TYPE: DNA
<213> ORGANISM: Arabidopsis thaliana

<400> SEQUENCE: 13
atggatccga ttaagctgac aacagaagct aaggtccctg ctaagcgatc aaaggctaca    60
agccactact tgcctcttca taaacgccag ttctatcatt cccgaaccgg tcagccattg   120
tcacttgagc aagttatgtc tgaccgagat agcgaaaatg acgtcgacaa aaatgatgat   180
gctgcacatc tcgaagaaag ccagatgctt aatggttcca tggatgagaa tgaaatcgta   240
gcagagagat tcataaaact ttggaactcc tttgttaaac agcaaggat tgttgcagat   300 gctcatattc cttgggcatg tgaagcattc tcaagattac acctgcaaga gctgcgcagt   360
aacttatcac tcgacttgtg ctggagacaa ttcatgatca acaatgggat ttatggactt   420
cttgacagag tcaccatgaa caaatgcaat accatcatct accataatat ctcaactacc   480
aacgatgaca taaacaataa caacacaagg acgactgata tatggatgt tgtcgacgat   540 gacataaaca gagacaag                                                  558

<210> SEQ ID NO 14
<211> LENGTH: 186
<212> TYPE: PRT
<213> ORGANISM: Arabidopsis thaliana

<400> SEQUENCE: 14

Met Asp Pro Ile Lys Leu Thr Thr Glu Ala Lys Val Pro Ala Lys Arg
1               5                  10                  15

Ser Lys Ala Thr Ser His Tyr Leu Pro Leu His Lys Arg Gln Phe Tyr
            20                  25                  30

His Ser Arg Thr Gly Gln Pro Leu Ser Leu Glu Gln Val Met Ser Asp
        35                  40                  45

Arg Asp Ser Glu Asn Asp Val Asp Lys Asn Asp Asp Ala Ala His Leu
    50                  55                  60

Glu Glu Ser Gln Met Leu Asn Gly Ser Met Asp Glu Asn Glu Ile Val
65                  70                  75                  80

Ala Glu Arg Phe Ile Lys Leu Trp Asn Ser Phe Val Lys Gln Gln Arg
                85                  90                  95

Ile Val Ala Asp Ala His Ile Pro Trp Ala Cys Glu Ala Phe Ser Arg
            100                 105                 110

Leu His Leu Gln Glu Leu Arg Ser Asn Leu Ser Leu Asp Leu Cys Trp
        115                 120                 125

Arg Gln Phe Met Ile Lys Gln Trp Asp Tyr Gly Leu Leu Asp Arg Val
    130                 135                 140

Thr Met Asn Lys Cys Asn Thr Ile Ile Tyr His Asn Ile Ser Thr Thr
```

|   |   |   |   |
|---|---|---|---|
| 145 | 150 | 155 | 160 |

Asn Asp Asp Ile Asn Asn Asn Asn Thr Arg Thr Thr Asp Asn Met Asp
                    165                  170                  175

Val Val Asp Asp Asp Ile Asn Arg Asp Lys
        180                  185

<210> SEQ ID NO 15
<211> LENGTH: 4441
<212> TYPE: DNA
<213> ORGANISM: Homo sapiens

<400> SEQUENCE: 15

| | | | | |
|---|---|---|---|---|
| ctctgaggag | acactttttt | tttcctccct | ccttccctcc | tctcctcctc | ccttcccttc | 60 |
| ccctctcctc | ccctctctcc | tccttccccc | ctcggtccgc | cggagcctgc | tggggcgagc | 120 |
| ggttggtatt | gcaggcgctt | gctctccggg | gccgcccggc | gggtagctgg | cgggggagg | 180 |
| aggcaggaac | cgcgatggcg | cctcagaagc | acggcggtgg | gggaggggc | ggctcggggc | 240 |
| ccagcgcggg | gtccggggga | ggcggcttcg | ggggttcggc | ggcggtggcg | gcggcgacgg | 300 |
| cttcgggcgg | caaatccggc | ggcgggagct | gtggaggggg | tggcagttac | tcggcctcct | 360 |
| cctcctcctc | cgcggcggca | gcggcggggg | ctgcggtgtt | accggtgaag | aagccgaaaa | 420 |
| tggagcacgt | ccaggctgac | cacgagcttt | cctccaggc | ctttgagaag | ccaacacaga | 480 |
| tctatagatt | tcttcgaact | cggaatctca | tagcaccaat | atttttgcac | agaactctta | 540 |
| cttacatgtc | tcatcgaaac | tccagaacaa | acatcaaaag | gaaacatttt | aaagttgatg | 600 |
| atatgttatc | aaaagtagag | aaaatgaaag | gagagcaaga | atctcatagc | ttgtcagctc | 660 |
| atttgcagct | tacgtttact | ggtttcttcc | acaaaaatga | taagccatca | ccaaaactcag | 720 |
| aaaatgaaca | aaattctgtt | accctggaag | tcctgcttgt | gaaagtttgc | cacaaaaaaa | 780 |
| gaaaggatgt | aagttgtcca | ataaggcaag | ttcccacagg | taaaaagcag | gtgcctttga | 840 |
| ttcctgacct | caatcaaaca | aaacccggaa | atttcccgtc | ccttgcagtt | tccagtaatg | 900 |
| aatttgaacc | tagtaacagc | catatggtga | agtcttactc | gttgctattt | agagtgactc | 960 |
| gtccaggaag | aagagagttt | aatggaatga | ttaatggaga | aaccaatgaa | atattgatg | 1020 |
| tcaatgaaga | gcttccagcc | agaagaaaac | gaaatcgtga | ggatgggaa | aagacatttg | 1080 |
| ttgcacaaat | gacagtattt | gataaaaaca | ggcgcttaca | gcttttagat | ggggaatatg | 1140 |
| aagtagccat | gcaggaaatg | gaagaatgtc | caataagcaa | gaaaagagca | acatgggaga | 1200 |
| ctattcttga | tgggaagagg | ctgcctccat | tcgaaacatt | ttctcaggga | cctacgttgc | 1260 |
| agttcactct | tcgttggaca | ggagagacca | tgataaaatc | tacggctcct | attgccaaac | 1320 |
| ctcttgccac | tagaaattca | gagagtctcc | atcaggaaaa | caagcctggt | tcagttaaac | 1380 |
| ctactcaaac | tattgctgtt | aaagaatcat | tgactacaga | tctacaaaca | agaaaagaaa | 1440 |
| aggatactcc | aaatgaaaac | cgacaaaaat | taagaatatt | ttatcagttt | ctctataaca | 1500 |
| acaatacaag | gcaacaaact | gaagcaagag | atgacctgca | ttgcccttgg | tgtactctga | 1560 |
| actgccgcaa | actttatagt | ttactcaagc | atcttaaact | ctgccatagc | agatttatct | 1620 |
| tcaactatgt | ttatcatcca | aaaggtgcta | ggatagatgt | ttctatcaat | gagtgttatg | 1680 |
| atggctccta | tgcaggaaat | cctcaggata | ttcatcgcca | acctggattt | gcttttagtc | 1740 |
| gcaacggacc | agttaagaga | acacctatca | cacatattct | tgtgtgcagg | ccaaaacgaa | 1800 |
| caaaagcaag | catgtctgaa | tttcttgaat | ctgaagatgg | ggaagtagaa | cagcaaagaa | 1860 |
| catatagtag | tggccacaat | cgtctgtatt | tccatagtga | tacctgctta | cctctccgtc | 1920 |

-continued

```
cacaagaaat ggaagtagat agtgaagatg aaaaggatcc tgaatggcta agagaaaaaa    1980
ccattacaca aattgaagag ttttctgatg ttaatgaagg agagaaagaa gtgatgaaac    2040
tctggaatct ccatgtcatg aagcatgggt ttattgctga caatcaaatg aatcatgcct    2100
gtatgctgtt tgtagaaaat tatggacaga aaataattaa gaagaattta tgtcgaaact    2160
tcatgcttca tctagtcagc atgcatgact ttaatcttat tagcataatg tcaatagata    2220
aagctgttac caagctccgt gaaatgcagc aaaaattaga aaaggggaa tctgcttccc     2280
ctgcaaacga agaaataact gaagaacaaa atgggacagc aaatggattt agtgaaatta    2340
actcaaaaga gaaagctttg gaaacagata gtgtctcagg ggtttcaaaa cagagcaaaa    2400
aacaaaaact ctgaaaagct ctaaccccat gttatggaca aacactgaaa ttacatttta    2460
gggaattcat cctctaagaa ttatgttttt gtttttaatc atatgttcca aacaggcact    2520
gttagatgaa gtaaatgatt tcaacaagga tatttgtatc agggttctac ttcacttcat    2580
tatgcagcat tacatgtata tcactttat tgatgtcatt aaaacattct gtactttaag    2640
catgaaaagc aatatttcaa gtattttta aactcaacaa atgtcatcaa atatgttgaa     2700
ttgatctaga aattatttca tatataaatc agaatttttt tgcatttatg aacggctgtt    2760
tttctacttt gtaattgtga gacattttct tggggaggga aaattggaat ggttcccttt    2820
tttagaaatt gaagtggtct tcatatgtca actacagaaa aggaaaaaaa tagaaattga    2880
aggatttta tgaaattata ttgcattact atttgcagtc aaactttgat ccttgttttt     2940
gaaatcattt gtcaattcgg aatgaaaaat tataatgtaa ttttacatta cataagttcc    3000
ttttacaatt aaaaaatagc acttcttcat cttatgcctg tttgagaaga tattaaattt    3060
tcacattgtt gacagtgaaa tgctatgttg gtttataaga ttacagacca tttgttttca    3120
tgtggataat tttagtgcat tgctcacccg gtatgttttt ttttttttaac ttgaacattt    3180
tgcttgtttt gtttttcttt ttaattaga taatcacacg gaaaattaag ctgttcatat     3240
ctttaaatta ggattgcaaa ccaaggaaag aacgcatttg agattttaag atgtcactta    3300
taagggggaga agtgttctta aaaagtcaac cagaaaactg ttatgccttt tatttgtttg    3360
caaggatgtc tttgtaatgt gtttcatgaa tagaatatcc aatagagata agctgacttg    3420
aatcattttg agcaatttg ccctgtgtta tatgtgtttc acgcacatat ttgcagttgg     3480
attttctcca acagaaagtg gattcactac tggcacatta acaagcacca ataggttttt    3540
attccaactc cgagcactgt ggttgagtaa catcaccttca attttttatt atccttaaag    3600
atattgcatt ttcatattct ttatttataa aggatcaatg ctgctgtaaa tacaggtatt    3660
tttaatttta aaatttcatt ccaccaccat cagatgcagt tccctatttt gtttaatgaa    3720
gggatatata agctttctaa tggtgtcttc agaaatttat aaaatgtaaa tactgattgg    3780
actggtcttt aagatgtgtt taactgtgag gctatttaac gaatagtgtg gatgtgattt     3840
gtcatccagt attaagttct tagtcattga tttttgtgtt taaaaaaaaa taggaaagag    3900
ggaaactgca gctttcatta cagattcctt gattggtaag ctctccaaat gatgagttct    3960
agtaaactct gattttgcc tctggatagt agatctcgag cgtttatctc gggctttaat     4020
ttgctaaagc tgtgcacata tgtaaaaaaa aaaaaaaaa gattatttta ggggagatgt    4080
aggtgtagaa ttattgctta tgtcattct taagcagtta tgctcttaat gcttaaaaga     4140
aggctagcat tgtttgcaca aaaagttggt gattcccacc ccaaatagta ataaaattac    4200
ttctgttgag taaactttttt atgtcatcgt aaaagctgga aaaatcccctt tgtttctatt   4260
```

-continued

```
tataaaaaaa gtgctttttct atatgtaccc ttgataacag attttgaaga aatcctgtaa    4320
gatgataaag catttgaatg gtacagtaga tgtaaaaaaa attcagttta aaagaacatt    4380
tgtttttaca ttaaatgttt atttgaaatc aaatgatttt gtacataaag ttcaataata    4440
t                                                                    4441
```

<210> SEQ ID NO 16
<211> LENGTH: 803
<212> TYPE: PRT
<213> ORGANISM: Homo sapiens

<400> SEQUENCE: 16

```
Leu Arg Arg His Phe Phe Pro Pro Ser Phe Pro Pro Leu Leu Leu
 1               5                  10                  15

Pro Ser Leu Pro Leu Ser Ser Pro Ser Ser Phe Pro Pro Arg Ser
            20                  25                  30

Ala Gly Ala Cys Trp Gly Glu Arg Leu Val Leu Gln Ala Leu Ala Leu
        35                  40                  45

Arg Gly Arg Pro Ala Gly Ser Trp Arg Gly Glu Glu Ala Gly Thr Ala
    50                  55                  60

Met Ala Pro Gln Lys His Gly Gly Gly Gly Gly Ser Gly Pro
65                  70                  75                  80

Ser Ala Gly Ser Gly Gly Gly Phe Gly Gly Ser Ala Ala Val Ala
                85                  90                  95

Ala Ala Thr Ala Ser Gly Gly Lys Ser Gly Gly Ser Cys Gly Gly
            100                 105                 110

Gly Gly Ser Tyr Ser Ala Ser Ser Ser Ser Ala Ala Ala Ala Ala
        115                 120                 125

Gly Ala Ala Val Leu Pro Val Lys Lys Pro Lys Met Glu His Val Gln
    130                 135                 140

Ala Asp His Glu Leu Phe Leu Gln Ala Phe Glu Lys Pro Thr Gln Ile
145                 150                 155                 160

Tyr Arg Phe Leu Arg Thr Arg Asn Leu Ile Ala Pro Ile Phe Leu His
                165                 170                 175

Arg Thr Leu Thr Tyr Met Ser His Arg Asn Ser Arg Thr Asn Ile Lys
            180                 185                 190

Arg Lys Thr Phe Lys Val Asp Asp Met Leu Ser Lys Val Glu Lys Met
        195                 200                 205

Lys Gly Glu Gln Glu Ser His Ser Leu Ser Ala His Leu Gln Leu Thr
    210                 215                 220

Phe Thr Gly Phe Phe His Lys Asn Asp Lys Pro Ser Pro Asn Ser Glu
225                 230                 235                 240

Asn Glu Gln Asn Ser Val Thr Leu Glu Val Leu Leu Val Lys Val Cys
                245                 250                 255

His Lys Lys Arg Lys Asp Val Ser Cys Pro Ile Arg Gln Val Pro Thr
            260                 265                 270

Gly Lys Lys Gln Val Pro Leu Ile Pro Asp Leu Asn Gln Thr Lys Pro
        275                 280                 285

Gly Asn Phe Pro Ser Leu Ala Val Ser Ser Asn Glu Phe Glu Pro Ser
    290                 295                 300

Asn Ser His Met Val Lys Ser Tyr Ser Leu Leu Phe Arg Val Thr Arg
305                 310                 315                 320

Pro Gly Arg Arg Glu Phe Asn Gly Met Ile Asn Gly Glu Thr Asn Glu
                325                 330                 335
```

```
Asn Ile Asp Val Asn Glu Glu Leu Pro Ala Arg Arg Lys Arg Asn Arg
            340                 345                 350

Glu Asp Gly Glu Lys Thr Phe Val Ala Gln Met Thr Val Phe Asp Lys
            355                 360                 365

Asn Arg Arg Leu Gln Leu Leu Asp Gly Glu Tyr Glu Val Ala Met Gln
            370                 375                 380

Glu Met Glu Glu Cys Pro Ile Ser Lys Lys Arg Ala Thr Trp Glu Thr
385                 390                 395                 400

Ile Leu Asp Gly Lys Arg Leu Pro Pro Phe Glu Thr Phe Ser Gln Gly
            405                 410                 415

Pro Thr Leu Gln Phe Thr Leu Arg Trp Thr Gly Glu Thr Asn Asp Lys
            420                 425                 430

Ser Thr Ala Pro Ile Ala Lys Pro Leu Ala Thr Arg Asn Ser Glu Ser
            435                 440                 445

Leu His Gln Glu Asn Lys Pro Gly Ser Val Lys Pro Thr Gln Thr Ile
            450                 455                 460

Ala Val Lys Glu Ser Leu Thr Thr Asp Leu Gln Thr Arg Lys Glu Lys
465                 470                 475                 480

Asp Thr Pro Asn Glu Asn Arg Gln Lys Leu Arg Ile Phe Tyr Gln Phe
            485                 490                 495

Leu Tyr Asn Asn Asn Thr Arg Gln Gln Thr Glu Ala Arg Asp Asp Leu
            500                 505                 510

His Cys Pro Trp Cys Thr Leu Asn Cys Arg Lys Leu Tyr Ser Leu Leu
            515                 520                 525

Lys His Leu Lys Leu Cys His Ser Arg Phe Ile Phe Asn Tyr Val Tyr
            530                 535                 540

His Pro Lys Gly Ala Arg Ile Asp Val Ser Ile Asn Glu Cys Tyr Asp
545                 550                 555                 560

Gly Ser Tyr Ala Gly Asn Pro Gln Asp Ile His Arg Gln Pro Gly Phe
            565                 570                 575

Ala Phe Ser Arg Asn Gly Pro Val Lys Arg Thr Pro Ile Thr His Ile
            580                 585                 590

Leu Val Cys Arg Pro Lys Arg Thr Lys Ala Ser Met Ser Glu Phe Leu
            595                 600                 605

Glu Ser Glu Asp Gly Glu Val Glu Gln Gln Arg Thr Tyr Ser Ser Gly
            610                 615                 620

His Asn Arg Leu Tyr Phe His Ser Asp Thr Cys Leu Pro Leu Arg Pro
625                 630                 635                 640

Gln Glu Met Glu Val Asp Ser Glu Asp Glu Lys Asp Pro Glu Trp Leu
            645                 650                 655

Arg Glu Lys Thr Ile Thr Gln Ile Glu Glu Phe Ser Asp Val Asn Glu
            660                 665                 670

Gly Glu Lys Glu Val Met Lys Leu Trp Asn Leu His Val Met Lys His
            675                 680                 685

Gly Phe Ile Ala Asp Asn Gln Met Asn His Ala Cys Met Leu Phe Val
            690                 695                 700

Glu Asn Tyr Gly Gln Lys Ile Ile Lys Lys Asn Leu Cys Arg Asn Phe
705                 710                 715                 720

Met Leu His Leu Val Ser Met His Asp Phe Asn Leu Ile Ser Ile Met
            725                 730                 735

Ser Ile Asp Lys Ala Val Thr Lys Leu Arg Glu Met Gln Gln Lys Leu
            740                 745                 750

Glu Lys Gly Glu Ser Ala Ser Pro Ala Asn Glu Glu Ile Thr Glu Glu
```

```
                755                 760                 765
Gln Asn Gly Thr Ala Asn Gly Phe Ser Glu Ile Asn Ser Lys Glu Lys
        770                 775                 780
Ala Leu Glu Thr Asp Ser Val Ser Gly Val Ser Lys Gln Ser Lys Lys
785                 790                 795                 800

Gln Lys Leu

<210> SEQ ID NO 17
<211> LENGTH: 22
<212> TYPE: PRT
<213> ORGANISM: Arabidopsis thaliana

<400> SEQUENCE: 17

Cys Pro Phe Cys Ser Met Leu Cys Gly Ser Phe Lys Gly Leu Gln Phe
1               5                   10                  15

His Leu Asn Ser Ser His
            20

<210> SEQ ID NO 18
<211> LENGTH: 21
<212> TYPE: PRT
<213> ORGANISM: Arabidopsis thaliana

<400> SEQUENCE: 18

Cys Pro Phe Cys Ala Glu Ser Tyr Asp Ile Ile Gly Leu Cys Cys His
1               5                   10                  15

Ile Asp Asp Glu His
            20

<210> SEQ ID NO 19
<211> LENGTH: 20
<212> TYPE: PRT
<213> ORGANISM: Arabidopsis thaliana

<400> SEQUENCE: 19

Cys Pro Val Cys Ser Leu Lys Val Gly Val Asp Ile Val Ala His Ile
1               5                   10                  15

Thr Leu His His
            20

<210> SEQ ID NO 20
<211> LENGTH: 21
<212> TYPE: PRT
<213> ORGANISM: Arabidopsis thaliana

<400> SEQUENCE: 20

Cys Ser Phe Cys Lys Arg Glu Phe Arg Ser Ala Gln Ala Leu Gly Gly
1               5                   10                  15

His Met Asn Val His
            20

<210> SEQ ID NO 21
<211> LENGTH: 21
<212> TYPE: PRT
<213> ORGANISM: Arabidopsis thaliana

<400> SEQUENCE: 21

Cys Pro Phe Cys Ser Asp Tyr Phe Asp Ile Val Ser Leu Cys Cys His
1               5                   10                  15

Ile Asp Glu Asp His
            20
```

<210> SEQ ID NO 22
<211> LENGTH: 21
<212> TYPE: PRT
<213> ORGANISM: Arabidopsis thaliana

<400> SEQUENCE: 22

Cys Pro Phe Cys Ser Asp Asp Tyr Asp Leu Val Glu Leu Cys His His
 1               5                  10                  15

Ile Asp Glu Glu His
            20

<210> SEQ ID NO 23
<211> LENGTH: 22
<212> TYPE: PRT
<213> ORGANISM: Saccharomyces cerevisiae

<400> SEQUENCE: 23

Cys Pro Ile Cys Leu Arg Lys Phe Asp Asn Leu Gln Ala Leu Asn Ala
 1               5                  10                  15

His Leu Asp Val Glu His
            20

<210> SEQ ID NO 24
<211> LENGTH: 21
<212> TYPE: PRT
<213> ORGANISM: Saccharomyces cerevisiae

<400> SEQUENCE: 24

Cys Pro Ile Cys Ser Lys Pro Cys Val Gly Glu Asn Gly Leu Gln Met
 1               5                  10                  15

His Met Ile Ile His
            20

<210> SEQ ID NO 25
<211> LENGTH: 22
<212> TYPE: PRT
<213> ORGANISM: Schizosaccharomyces pombe

<400> SEQUENCE: 25

Cys Pro Tyr Cys Glu Ile Lys Cys Lys Arg Lys Asp Leu Leu Lys Arg
 1               5                  10                  15

His Ile Gln Arg Phe His
            20

<210> SEQ ID NO 26
<211> LENGTH: 22
<212> TYPE: PRT
<213> ORGANISM: Caenorhabditis elegans

<400> SEQUENCE: 26

Cys Asp Val Cys Ala Phe Lys Cys Ser Ser Tyr Gln Thr Leu Glu Ala
 1               5                  10                  15

His Leu Thr Ser Asn His
            20

<210> SEQ ID NO 27
<211> LENGTH: 22
<212> TYPE: PRT
<213> ORGANISM: Caenorhabditis elegans

<400> SEQUENCE: 27

-continued

Cys Pro Val Cys Glu Leu Val Ile Pro Thr Glu Lys Gly Leu Lys Asn
1               5                   10                  15

His Met Asn Gln Lys His
            20

<210> SEQ ID NO 28
<211> LENGTH: 22
<212> TYPE: PRT
<213> ORGANISM: Caenorhabditis elegans

<400> SEQUENCE: 28

Cys Pro Ile Cys Lys Cys Glu Cys Ser Gly Arg Glu Asp Cys Gln Leu
1               5                   10                  15

His Met Tyr Ala Ser His
            20

<210> SEQ ID NO 29
<211> LENGTH: 22
<212> TYPE: PRT
<213> ORGANISM: Drosophila melanogaster

<400> SEQUENCE: 29

Cys Pro Tyr Cys Arg Arg Thr Phe Ser Cys Tyr Tyr Ser Leu Lys Arg
1               5                   10                  15

His Phe Gln Asp Lys His
            20

<210> SEQ ID NO 30
<211> LENGTH: 22
<212> TYPE: PRT
<213> ORGANISM: Drosophila melanogaster

<400> SEQUENCE: 30

Cys Pro Ile Cys Tyr Ala Val Ile Arg Gln Ser Arg Asn Leu Arg Arg
1               5                   10                  15

His Leu Glu Leu Arg His
            20

<210> SEQ ID NO 31
<211> LENGTH: 22
<212> TYPE: PRT
<213> ORGANISM: Drosophila melanogaster

<400> SEQUENCE: 31

Cys Cys Phe Cys Ser Met Cys Phe Glu Ser Val Gln Glu Leu Val Arg
1               5                   10                  15

His Leu Ser Gly His His
            20

<210> SEQ ID NO 32
<211> LENGTH: 22
<212> TYPE: PRT
<213> ORGANISM: Homo sapiens

<400> SEQUENCE: 32

Cys Pro Phe Cys Arg Ala Leu Phe Lys Ala Lys Thr Ala Leu Glu Ala
1               5                   10                  15

His Ile Arg Ser Arg His
            20

<210> SEQ ID NO 33
<211> LENGTH: 22

```
<212> TYPE: PRT
<213> ORGANISM: Homo sapiens

<400> SEQUENCE: 33

Cys Pro Trp Cys Thr Leu Asn Cys Arg Lys Leu Tyr Ser Leu Leu Lys
 1               5                  10                  15

His Leu Lys Leu Cys His
            20

<210> SEQ ID NO 34
<211> LENGTH: 22
<212> TYPE: PRT
<213> ORGANISM: Homo sapiens

<400> SEQUENCE: 34

Cys Glu Val Cys Ala Phe Ala Cys Lys Arg Lys Tyr Glu Leu Gln Lys
 1               5                  10                  15

His Met Ala Ser Gln His
            20

<210> SEQ ID NO 35
<211> LENGTH: 22
<212> TYPE: PRT
<213> ORGANISM: Mus musculus

<400> SEQUENCE: 35

Cys Pro Tyr Cys Pro Pro Asn Gly Arg Val Arg Gly Asp Leu Val Glu
 1               5                  10                  15

His Leu Arg Gln Ala His
            20

<210> SEQ ID NO 36
<211> LENGTH: 21
<212> TYPE: PRT
<213> ORGANISM: Mus musculus

<400> SEQUENCE: 36

Cys Arg Phe Cys Ala Lys Val Phe Gly Ser Asp Ser Ala Leu Gln Ile
 1               5                  10                  15

His Leu Arg Ser His
            20

<210> SEQ ID NO 37
<211> LENGTH: 22
<212> TYPE: PRT
<213> ORGANISM: Rattus norvegicus

<400> SEQUENCE: 37

Cys Asn Tyr Cys Pro Glu Met Phe Ala Asp Ile Asn Ser Leu Gln Glu
 1               5                  10                  15

His Ile Arg Val Ser His
            20

<210> SEQ ID NO 38
<211> LENGTH: 22
<212> TYPE: PRT
<213> ORGANISM: Xiphophorus maculatus

<400> SEQUENCE: 38

Cys Pro His Cys Glu Phe Arg Cys Ala Asp Gln Ser Asn Leu Lys Thr
 1               5                  10                  15

His Ile Lys Ser Lys His
```

```
<210> SEQ ID NO 39
<211> LENGTH: 39
<212> TYPE: DNA
<213> ORGANISM: Arabidopsis thaliana
<220> FEATURE:
<221> NAME/KEY: CDS
<222> LOCATION: (1)..(39)

<400> SEQUENCE: 39 gaa aag caa ttc atg cat ctt tgg aac tcg ttt gta aga        39
Glu Lys Gln Phe Met His Leu Trp Asn Ser Phe Val Arg
  1               5                  10

<210> SEQ ID NO 40
<211> LENGTH: 13
<212> TYPE: PRT
<213> ORGANISM: Arabidopsis thaliana

<400> SEQUENCE: 40

Glu Lys Gln Phe Met His Leu Trp Asn Ser Phe Val Arg
  1               5                  10

<210> SEQ ID NO 41
<211> LENGTH: 39
<212> TYPE: DNA
<213> ORGANISM: Arabidopsis thaliana
<220> FEATURE:
<221> NAME/KEY: CDS
<222> LOCATION: (1)..(24)

<400> SEQUENCE: 41 gaa aag caa ttc atg cat ctt tga aactcgtttg taaga           39
Glu Lys Gln Phe Met His Leu
  1               5

<210> SEQ ID NO 42
<211> LENGTH: 7
<212> TYPE: PRT
<213> ORGANISM: Arabidopsis thaliana

<400> SEQUENCE: 42

Glu Lys Gln Phe Met His Leu
  1               5

<210> SEQ ID NO 43
<211> LENGTH: 33
<212> TYPE: DNA
<213> ORGANISM: Arabidopsis thaliana
<220> FEATURE:
<221> NAME/KEY: CDS
<222> LOCATION: (1)..(33)

<400> SEQUENCE: 43 tgt ggt agc ttc aag ggg ctg caa ttt cat ttg                33
Cys Gly Ser Phe Lys Gly Leu Gln Phe His Leu
  1               5                  10

<210> SEQ ID NO 44
<211> LENGTH: 11
<212> TYPE: PRT
<213> ORGANISM: Arabidopsis thaliana

<400> SEQUENCE: 44

Cys Gly Ser Phe Lys Gly Leu Gln Phe His Leu
  1               5                  10
```

<210> SEQ ID NO 45
<211> LENGTH: 54
<212> TYPE: DNA
<213> ORGANISM: Arabidopsis thaliana
<220> FEATURE:
<221> NAME/KEY: CDS
<222> LOCATION: (1)..(36)

<400> SEQUENCE: 45

```
tgt ggt agc ttc aag gtg ggc aac tat tac aac tga ggggctgcaa           46
Cys Gly Ser Phe Lys Val Gly Asn Tyr Tyr Asn
 1               5                  10 tttcattt                                                              54
```

<210> SEQ ID NO 46
<211> LENGTH: 11
<212> TYPE: PRT
<213> ORGANISM: Arabidopsis thaliana

<400> SEQUENCE: 46

```
Cys Gly Ser Phe Lys Val Gly Asn Tyr Tyr Asn
 1               5                  10
```

<210> SEQ ID NO 47
<211> LENGTH: 1722
<212> TYPE: DNA
<213> ORGANISM: Arabidopsis thaliana

<400> SEQUENCE: 47

```
caagcttctt caattttgct tgctctctct tacacagcca atcggtgttt tcgcagcttt      60
caggcctcaa tccaagacat tctatataag catattgcag aagaggcggt tctaattgtt     120
gcattgagtt tatcgctatg acgtagggaa attctaattt aggggaggcc tcagagtttg     180
cactaacttc ataatcggct cttgacgttg ttgagtgtaa ttgaacaaga atgtgtaggc     240
agaattgtcg cgcgaaatcc tcaccggagg aagtgatttc aactgatgag aatctcttga     300
tatattgtaa acctgttcga ctatataaca tctttcacct tcgctctcta ggcaacccat     360
cgtttcttcc aagatgcttg aactacaaaa ttggagcaaa gcgcaaaaga aagtcaagat     420
ctactgggat ggtagttttc aactataagg attgtaataa cacattacag aaaactgaag     480
ttagggagga ttgttcttgt ccattttgct ctatgctatg tggtagcttc aagggggctgc     540
aatttcattt gaattcatct catgattat ttgaatttga gttcaagctt ttcgaagaat     600
accagacagt taatgtttct gtaaaactta attccttcat atttgaggaa gaggaagtg      660
atgacgataa atttgagccc ttctctctct gctcgaaacc tcgtaagcgg agacaaagag     720
gtggcagaaa taacaccagg agacttaaag tatgcttttt accgttggat tcacccagtt     780
taactaatgg cacagaaaat ggaatcaccc tacttaatga tggaaaccgt ggtttaggat     840
atcccgaggc aacagagctt gctggacaat ttgagatgac cagcaacatt ccaccagcca     900
tagcccactc ttctctggac gctggtgcta aagttatatt gacaagcgaa gctgtggtcc     960
ctgctactaa gacaagaaag ttatctgctg agcgatcaga ggctagaagc cacctacttc    1020
ttcagaaacg ccaattctat cattctcaca gagtccagcc aatggcgctt gagcaagtaa    1080
tgtctgaccg ggatagcgag gatgaagtcg atgacgatgt tgcagatttt gaagatcgcc    1140
agatgcttga tgactttgtg gatgtgaata aagatgaaaa gcaattcatg catctttgaa    1200
actcgtttgt aagaaaacaa agggttatag cagatggtca tatctcttgg gcatgtgaag    1260
```

```
cattttcaag attttacgag aaagagttgc accgttactc atcactcttc tggtgttgga    1320
gattgttttt gattaaacta tggaaccatg gacttgtcga ctcagccacc atcaacaact    1380
gcaataccat cctcgagaat tgccgtaata gctcagacac caccaccacc aacaacaaca    1440
acagtgtgga tcgtcccagt gactcaaaca ccaacaacaa taacattgtg gatcatccca    1500
atgacataaa caacaagaac aatgttgaca acaaggacaa taacagcaga gacaaagtaa    1560
ttaaatagga aaatctccgg cttttatgat accgatttat cggattgtaa cttattcttc    1620
tttcttaaaa aattgtttag gagcaaacaa attttttata tgttagtgta ttcaactgat    1680 tacatttta gttaaaaaaa aaatggatt ctgcttataa ct                         1722

<210> SEQ ID NO 48
<211> LENGTH: 40
<212> TYPE: DNA
<213> ORGANISM: Arabidopsis thaliana

<400> SEQUENCE: 48
gaaaagcaat tcatgcatct ttggaactcg tttgtaagaa                            40

<210> SEQ ID NO 49
<211> LENGTH: 40
<212> TYPE: DNA
<213> ORGANISM: Arabidopsis thaliana

<400> SEQUENCE: 49
gaaaagcaat tcatgcatct ttgaaactcg tttgtaagaa                            40

<210> SEQ ID NO 50
<211> LENGTH: 10
<212> TYPE: DNA
<213> ORGANISM: Artificial Sequence
<220> FEATURE:
<221> NAME/KEY: misc_feature
<222> LOCATION: (4)..(7)
<223> OTHER INFORMATION: n=a or g or c or t
<220> FEATURE:
<223> OTHER INFORMATION: Description of Artificial Sequence: Xmn1 site

<400> SEQUENCE: 50 cttnnnnaag                                                             10

<210> SEQ ID NO 51
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 51
gagaagtagt tacctttgtt ttcttacaga agagt                                 35

<210> SEQ ID NO 52
<211> LENGTH: 40
<212> TYPE: DNA
<213> ORGANISM: Artificial Sequence
<220> FEATURE:
<223> OTHER INFORMATION: Description of Artificial Sequence: PCR product

<400> SEQUENCE: 52
gaaaagcaat tcatgcatct ttggaactct tctgtaagaa                            40

<210> SEQ ID NO 53
<211> LENGTH: 40
```

```
<212> TYPE: DNA
<213> ORGANISM: Artificial Sequence
<220> FEATURE:
<223> OTHER INFORMATION: Description of Artificial Sequence: PCR product

<400> SEQUENCE: 53
gaaaagcaat tcatggatct ttgaaactct tctgtaagaa                           40

<210> SEQ ID NO 54
<211> LENGTH: 367
<212> TYPE: PRT
<213> ORGANISM: Homo sapiens

<400> SEQUENCE: 54
```

| | | | | | | | | | | | | | | |
|---|---|---|---|---|---|---|---|---|---|---|---|---|---|---|
|Ile|Ala|Lys|Pro|Leu|Ala|Thr|Arg|Asn|Ser|Glu|Ser|Leu|His|Gln|Glu|
|1| | | |5| | | | |10| | | | |15|

| | | | | | | | | | | | | | | |
|---|---|---|---|---|---|---|---|---|---|---|---|---|---|---|
|Asn|Lys|Pro|Gly|Ser|Val|Lys|Pro|Thr|Gln|Thr|Ile|Ala|Val|Lys|Glu|
| | | |20| | | | |25| | | | |30| |

| | | | | | | | | | | | | | | |
|---|---|---|---|---|---|---|---|---|---|---|---|---|---|---|
|Ser|Leu|Thr|Thr|Asp|Leu|Gln|Thr|Arg|Lys|Glu|Lys|Asp|Thr|Pro|Asn|
| | |35| | | | |40| | | | |45| | |

| | | | | | | | | | | | | | | |
|---|---|---|---|---|---|---|---|---|---|---|---|---|---|---|
|Glu|Asn|Arg|Gln|Lys|Leu|Arg|Ile|Phe|Tyr|Gln|Phe|Leu|Tyr|Asn|Asn|
| |50| | | | |55| | | | |60| | | |

| | | | | | | | | | | | | | | |
|---|---|---|---|---|---|---|---|---|---|---|---|---|---|---|
|Asn|Thr|Arg|Gln|Gln|Thr|Glu|Ala|Arg|Asp|Asp|Leu|His|Cys|Pro|Trp|
|65| | | | |70| | | | |75| | | | |80|

| | | | | | | | | | | | | | | |
|---|---|---|---|---|---|---|---|---|---|---|---|---|---|---|
|Cys|Thr|Leu|Asn|Cys|Arg|Lys|Leu|Tyr|Ser|Leu|Leu|Lys|His|Leu|Lys|
| | | | |85| | | | |90| | | | |95| |

| | | | | | | | | | | | | | | |
|---|---|---|---|---|---|---|---|---|---|---|---|---|---|---|
|Leu|Cys|His|Ser|Arg|Phe|Ile|Phe|Asn|Tyr|Val|Tyr|His|Pro|Lys|Gly|
| | | | |100| | | | |105| | | | |110| |

| | | | | | | | | | | | | | | |
|---|---|---|---|---|---|---|---|---|---|---|---|---|---|---|
|Ala|Arg|Ile|Asp|Val|Ser|Ile|Asn|Glu|Cys|Tyr|Asp|Gly|Ser|Tyr|Ala|
| | | | |115| | | | |120| | | | |125| |

| | | | | | | | | | | | | | | |
|---|---|---|---|---|---|---|---|---|---|---|---|---|---|---|
|Gly|Asn|Pro|Gln|Asp|Ile|His|Arg|Gln|Pro|Gly|Phe|Ala|Phe|Ser|Arg|
| | |130| | | | |135| | | | |140| | | |

| | | | | | | | | | | | | | | |
|---|---|---|---|---|---|---|---|---|---|---|---|---|---|---|
|Asn|Gly|Pro|Val|Lys|Arg|Thr|Pro|Ile|Thr|His|Ile|Leu|Val|Cys|Arg|
|145| | | | |150| | | | |155| | | | |160|

| | | | | | | | | | | | | | | |
|---|---|---|---|---|---|---|---|---|---|---|---|---|---|---|
|Pro|Lys|Arg|Thr|Lys|Ala|Ser|Met|Ser|Glu|Phe|Leu|Glu|Ser|Glu|Asp|
| | | | |165| | | | |170| | | | |175| |

| | | | | | | | | | | | | | | |
|---|---|---|---|---|---|---|---|---|---|---|---|---|---|---|
|Gly|Glu|Val|Glu|Gln|Gln|Arg|Thr|Tyr|Ser|Ser|Gly|His|Asn|Arg|Leu|
| | | | |180| | | | |185| | | | |190| |

| | | | | | | | | | | | | | | |
|---|---|---|---|---|---|---|---|---|---|---|---|---|---|---|
|Tyr|Phe|His|Ser|Asp|Thr|Cys|Leu|Pro|Leu|Arg|Pro|Gln|Glu|Met|Glu|
| | | | |195| | | | |200| | | | |205| |

| | | | | | | | | | | | | | | |
|---|---|---|---|---|---|---|---|---|---|---|---|---|---|---|
|Val|Asp|Ser|Glu|Asp|Glu|Lys|Asp|Pro|Glu|Trp|Leu|Arg|Glu|Lys|Thr|
| | | |210| | | | |215| | | | |220| | |

| | | | | | | | | | | | | | | |
|---|---|---|---|---|---|---|---|---|---|---|---|---|---|---|
|Ile|Thr|Gln|Ile|Glu|Glu|Phe|Ser|Asp|Val|Asn|Glu|Gly|Glu|Lys|Glu|
|225| | | | |230| | | | |235| | | | |240|

| | | | | | | | | | | | | | | |
|---|---|---|---|---|---|---|---|---|---|---|---|---|---|---|
|Val|Met|Lys|Leu|Trp|Asn|Leu|His|Val|Met|Lys|His|Gly|Phe|Ile|Ala|
| | | | |245| | | | |250| | | | |255| |

| | | | | | | | | | | | | | | |
|---|---|---|---|---|---|---|---|---|---|---|---|---|---|---|
|Asp|Asn|Gln|Met|Asn|His|Ala|Cys|Met|Leu|Phe|Val|Glu|Asn|Tyr|Gly|
| | | |260| | | | |265| | | | |270| | |

| | | | | | | | | | | | | | | |
|---|---|---|---|---|---|---|---|---|---|---|---|---|---|---|
|Gln|Lys|Ile|Ile|Lys|Lys|Asn|Leu|Cys|Arg|Asn|Phe|Met|Leu|His|Leu|
| | |275| | | | |280| | | | |285| | | |

| | | | | | | | | | | | | | | |
|---|---|---|---|---|---|---|---|---|---|---|---|---|---|---|
|Val|Ser|Met|His|Asp|Phe|Asn|Leu|Ile|Ser|Ile|Met|Ser|Ile|Asp|Lys|
| |290| | | | |295| | | | |300| | | | |

| | | | | | | | | | | | | | | |
|---|---|---|---|---|---|---|---|---|---|---|---|---|---|---|
|Ala|Val|Thr|Lys|Leu|Arg|Glu|Met|Gln|Gln|Lys|Leu|Glu|Lys|Gly|Glu|
|305| | | | |310| | | | |315| | | | |320|

| | | | | | | | | | | |
|---|---|---|---|---|---|---|---|---|---|---|
|Ser|Ala|Ser|Pro|Ala|Asn|Glu|Glu|Ile|Thr|Glu|Glu|Gln|Asn|Gly|Thr|
| | | | |325| | | | |330| | | | |335| |

-continued

Ala Asn Gly Phe Ser Glu Ile Asn Ser Lys Glu Lys Ala Leu Glu Thr
                340                 345                 350

Asp Ser Val Ser Gly Val Ser Lys Gln Ser Lys Gln Lys Leu
        355                 360                 365

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Motif

<400> SEQUENCE: 55

Gln Ala Leu Gly Gly
  1               5

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 56
actgttcgtc tccttcatca tg                                              22

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 57
ttgcttgcct gaaaaagta tg                                               22

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 58
tgtcgatatg cgaccagtac c                                               21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 59
caggcttaga cccaattgac c                                               21

<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 60
aggtaggatc cgacatcgtc ttcttattta ccg                                  33

<210> SEQ ID NO 61
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 61
ctcttgaatt caaaactatt cctactctca cac                                    33

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 62
gccaatcggt gttttcgcag ctttc                                             25

<210> SEQ ID NO 63
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 63
aagaataagt tacaatccga taaatcgg                                          28

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 64
cagtggttga agcttaagga gg                                                22

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 65
gcaatgaata aatcataatc ttgg                                              24

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 66
tctactggga tggtagtttt c                                                 21

<210> SEQ ID NO 67
<211> LENGTH: 23
<212> TYPE: DNA
<213> ORGANISM: Artificial Sequence
<220> FEATURE:

<223> OTHER INFORMATION: Description of Artificial Sequence: Primer

<400> SEQUENCE: 67
atatcccgag gcaacagagc ttg          23

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 68
catctttgga actcgtttg          19

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 69
ctcagttgta atagttgccc          20

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 70
aagagtgggc tatggctgg          19

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 71
gcaactcttt ctcgtaaaat cttg          24

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 72
gcctccataa ctgtcatcac atc          23

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 73
tttcattggt catgggatgg          20

```
<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 74
gacttcagag atgggtttat gc                                          22

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 75
tccatatcta gctccttcgc c                                           21

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 76
tgcgttcatt aagtaggcaa cagaaaatgg                                  30

<210> SEQ ID NO 77
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 77
gagaagtagt tacctttgtt ttcttacaga agagt                            35
```